(12) United States Patent
Ram et al.

(10) Patent No.: US 10,274,455 B2
(45) Date of Patent: *Apr. 30, 2019

(54) NANOELECTRONIC SENSOR PIXEL

(71) Applicant: RG SMART PTE. LTD., Singapore (SG)

(72) Inventors: Ayal Ram, Singapore (SG); Amir Lichtenstein, Singapore (SG); Xuan-Thang Vu, Zweibrücken (DE); Jessica Ka-Yan Law, Zweibrücken (DE); Miriam Schwartz, Zweibrücken (DE); Jannick Wilhelm, Zweibrücken (DE); Thanh Chien Nguyen, Zweibrücken (DE)

(73) Assignee: RG SMART PTE. LTD., Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 15/087,809

(22) Filed: Mar. 31, 2016

(65) Prior Publication Data
US 2016/0290957 A1 Oct. 6, 2016

Related U.S. Application Data

(60) Provisional application No. 62/140,990, filed on Mar. 31, 2015.

(51) Int. Cl.
*G01N 27/414* (2006.01)
*A61B 5/1477* (2006.01)
(Continued)

(52) U.S. Cl.
CPC ....... *G01N 27/4145* (2013.01); *A61B 5/1477* (2013.01); *C12Q 1/6825* (2013.01);
(Continued)

(58) Field of Classification Search
CPC .......... G01N 27/4145; G01N 27/4146; G01N 27/4148; G01N 33/54373; A61B 5/1477; C12Q 1/6825
See application file for complete search history.

(56) References Cited

U.S. PATENT DOCUMENTS 5,066,582 A * 11/1991 Tsuruta ............. G01N 33/5438
204/403.1
2016/0290958 A1* 10/2016 Ram ..................... C12Q 1/001

OTHER PUBLICATIONS

Dehzangi, et al. ("Electrical property comparison and charge transmission in p-type double gate and single gate junctionless accumulation transistors fabricated by AFM nanolithography," Nanoscale Research Letters, (2012) 7: 381. https://doi.org/10.1186/1556-276X-7-381.*

(Continued)

*Primary Examiner* — J. Christopher Ball
(74) *Attorney, Agent, or Firm* — Knobbe, Martens, Olson & Bear, LLP

(57) ABSTRACT

An electrical circuit element, defined as "pixel", can include at least one silicon nanowire open for contact with a medium for sensing; a metal electrode open for contact with said medium and used for feeding a high-frequency sinusoidal stimulation in impedance measurements and for sensing properties of said medium; implanted source and drain electrodes connected to said silicon nanowire and leaving the gate area and parts of said electrode open for contact with said medium; electrical metal contacts for connecting said pixel to an electrical circuit; and a reference electrode open for contact with said medium for creating a three-electrode-cell system and providing a constant gate potential in the circuit. Some embodiments provide a microelectronic sensor and wearable-patch sensor based on the array of these pixels. Also, some embodiments provide methods for per- (Continued)

forming DC readout, AC readout and a triple readout combining both DC and AC readouts and temperature sensing.

28 Claims, 48 Drawing Sheets

(51) Int. Cl.
*C12Q 1/6825* (2018.01)
*G01N 33/543* (2006.01)

(52) U.S. Cl.
CPC ..... *G01N 27/4146* (2013.01); *G01N 27/4148* (2013.01); *G01N 33/54373* (2013.01)

(56) References Cited

OTHER PUBLICATIONS

M. L. Zhang, C. Q. Yi, X. Fan, K. Q. Peng, N. B. Wong, M. S. Yang, R. Q. Zhang and S. T. Lee, A surface-enhanced Raman spectroscopy substrate for highly sensitive label-free immunoassay, Appl. Phys. Lett., 92 (2008), 043116.

A. Tarasov, Silicon Nanowire Field-effect Transistors for Sensing Applications, Ph.D. thesis, Universitäat Basel, Basel, (2012).

D. Bavli, M. Tkachev, H. Piwonski, E. Capua, I. d. Albuquerque, D. Bensimon, G. Haran, and R. Naaman, Detection and Quantification through a Lipid Membrane Using the Molecularly Controlled Semiconductor Resistor, Langmuir 28 (2012), 1020-1028.

Y. Cui, Q. Wei, H. Park, and C. M. Lieber, Nanowire nanosensors for highly sensitive and selective detection of biological and chemical species, Science 293 (2001), 1289-1292.

J. Hahm and C. M. Lieber, Direct ultrasensitive electrical detection of DNA and DNA sequence variations using nanowire nanosensors, Nano Letters 4 (2004), 51-54.

F. Patolsky, G. Zheng, O. Hayden, M. Lakadamyali, X. Zhuang, and C. Lieber, Electrical detection of single viruses, Proceedings of the National Academy of Sciences of the United States of America 101 (2004), 14017.

F. Patolsky, G. Zheng, and C. M. Lieber, Nanowire-based biosensors, Analytical Chemistry 78 (2006), 4260-4269.

Z. Jiang, Q. Qing, P. Xie, R. Gao, and C. M. Lieber, Kinked pn junction nanowire probes for high spatial resolution sensing and intracellular recording, Nano Letters 12 (2012), 1711-1716.

R. Elnathan, M. Kwiat, A. Pevzner, Y. Engel, L. Burstein, A. Khatchtourints, A. Lichtenstein, R. Kantaev, and F. Patolsky, Biorecognition layer engineering: overcoming screening limitations of nanowire-based FET devices, Nano Letters 12 (2012), 5245-5254.

G. Zhang, J. Chua, R. Chee, A. Agarwal, S. Wong, K. Buddharaju, and N. Balasubramanian, Highly sensitive measurements of PNA-DNA hybridization using oxide-etched silicon nanowire biosensors, Biosensors and Bioelectronics 23 (2008), 1701-1707.

X. T. Vu, J. F. Eschermann, R. Stockmann, R. Ghosh Moulick, A. Offenhäusser, and S. Ingebrandt, Top-down processed silicon nanowire transistor arrays for biosensing, Phys. Status Solidi A 206(3) (2009), 426-434.

X. T. Vu, R. Stockmann, B. Wolfrum, A. Offenhäusser, and S. Ingebrandt, Fabrication and application of a microfluidic-embedded silicon nanowire biosensor chip, Phys. Status Solidi A 207(4) (2010), 850-857.

C. Ahn, A. Kulkarni, H.-U Kim, C. Shin, Y. Xu, S. Jung, H. Kim, M. Lee, and T. Kim, Light-sensitive silicon nanowire array field effect transistor for glucose detection, Nano 9(8) (2014), 1450099 (6 pages).

\* cited by examiner

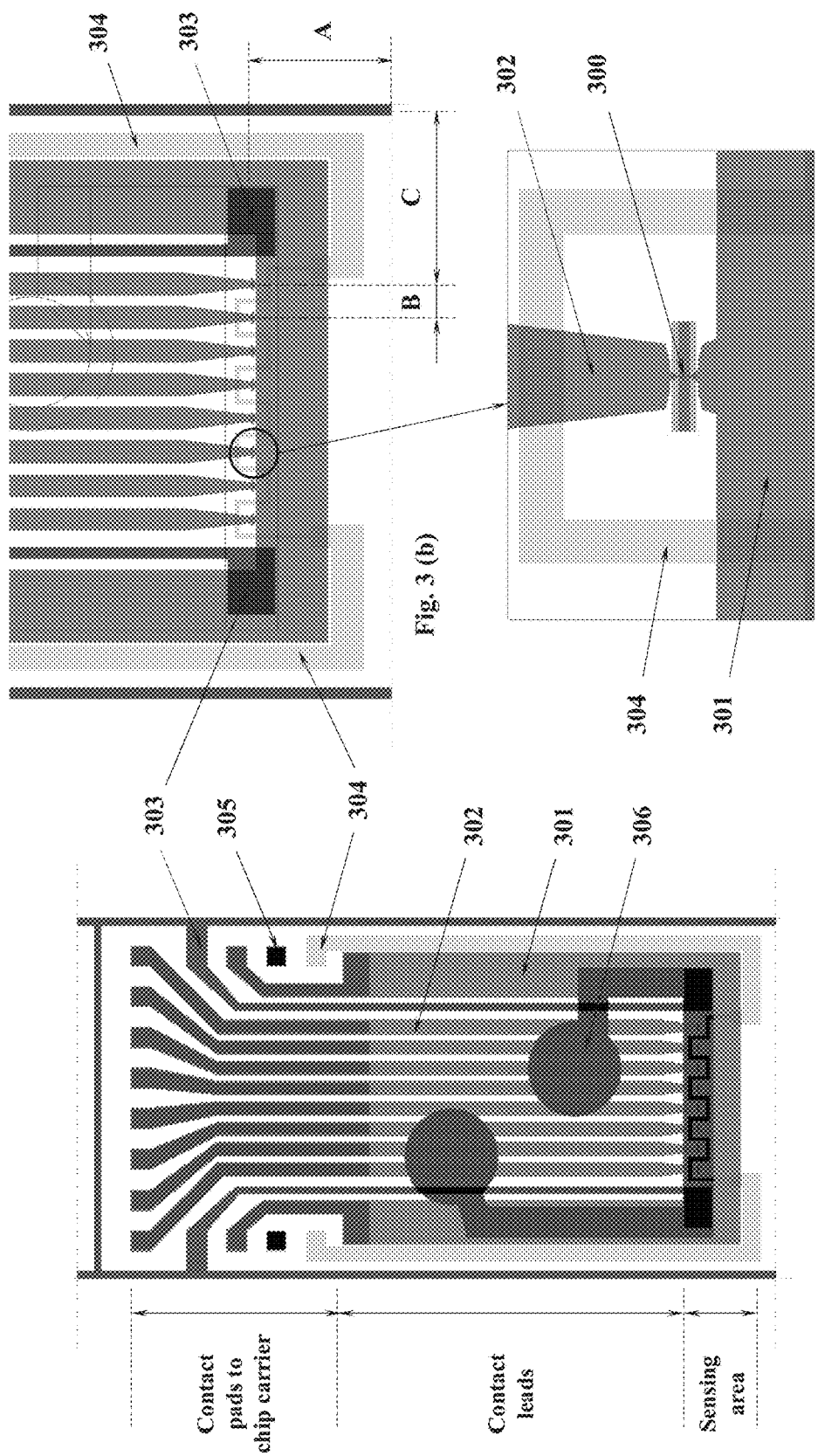

NANOELECTRONIC SENSOR PIXEL

TECHNICAL FIELD

In general, the present application relates to the field of nanoelectronics. In particular, the present application relates to the nanoelectronic sensor pixel based on silicon nanowires and metal counter electrode structures.

BACKGROUND

Nanomaterials possess unique physical properties due to their confinement down to the nanometer scale in at least one dimension. Combination of nanomaterials and biological processes opens up new horizons for modern biotechnological applications, particularly for biosensing. Not only nanomaterials enable miniaturisation of devices, but also ensure their high sensitivity due to the significantly increased surface-to-volume ratio.

As nanomaterials in general, nanowires and their arrays in particular, confined down to the nanometer thickness, show many advantages over conventional wires, such as significantly increased signal-to-noise ratio, increased charge carrier transport and low detection limit. Therefore, the nanowires are now considered a new class of ultrasensitive electrochemical tools and electrochemical sensors.

However, since these sensor devices operate in ultralow current regimes and are in general very sensitive to various influences from side parameters, which generally decreases the stability and reliability of the sensor operation, special designs and array layouts are advised, which enable maximum control of the sensors performance. This includes a gate voltage control from front side via a stable electrochemical reference electrode system and from back side via a back gate contact. In addition a shift to the frequency domain for alternative sensor readout stabilisation aids more reliable performance in biosensor applications.

Silicon nanomaterials are a type of nanomaterials with attractive properties, including excellent semiconducting, mechanical, optical properties, favourable biocompatibility, surface tailorability, and are relatively compatible with conventional silicon technology. A silicon nanowire (hereinbelow, "SiNW") is defined as a "one-dimensional" silicon nanostructure exhibiting a length-to-diameter ratio of 1000 or more. The diameter of a regular SiNW is in order of single-digit nanometers. At this scale, quantum mechanical laws become totally dominant, and SiNWs have many interesting properties that are not seen in larger objects and three-dimensional materials. Since quantum confinement of electrons in SiNWs to one dimension is predicted to be substantial only at diameters below 3 nm, the band structure is strongly modified for these nanowires having diameters of single-digit nanometers. The band gap in SiNWs increases for smaller diameters and a direct band gap can be obtained for sufficiently small diameters. Silicon nanowires have been extensively explored for myriad applications ranging from electronics to biology (M. Zhang et al 2008).

A field-effect transistor (FET) is a semiconductor-based device with relatively low power consumption used for switching or signal amplification in electrical circuits. Widely used transistors are metal oxide semiconductor field-effect transistors (MOSFETs) having two highly doped domains (n- or p-type) separated by a p- or n-type domains, respectively, with p-n or n-p junctions at the interface enabling a tunnelling operation. Common elements for doping of silicon are boron (p-type) or arsenic/phosphoric (n-type).

The doped domains are connected to source (S) and drain (D) ohmic contacts. A metal gate is placed on top of the area between the S and D contacts, separated by a thin, insulating oxide layer. Conductance of the transistor is controlled by an external field, for instance the gate field. By applying a positive or negative gate voltage at the gate, electrons are either attracted or repulsed at the semiconductor-oxide interface. Once the threshold voltage is reached, an inversion layer forms a conducting channel between the n- or p-type regions connected to the S and D contacts. Size of the formed channel depends on both, the external gate field and the selection of the materials. Applying an additional SD bias voltage enhances the charge carrier movement through the channel and narrows the channel at one certain end. Thus, conductance is altered, and electrons become attracted by the drain.

Ion-sensitive FETs (ISFETs) are similar to the common MOSFET, but the metal gate electrode is replaced with an electrolyte solution carrying analyte molecules and containing a reference electrode. The electrolyte solution is defined as a "liquid gate", which controls the current between the S and D contacts. The liquid gate electrode is separated from the channel by the gate insulator and/or an ionic "double layer" barrier, which is sensitive, for example to protons, and therefore, suitable for pH measurements. In general, binding reactions of charged analytes with corresponding ligand groups at the ISFET sensor surface cause a surface charge, which leads to an additional surface potential. This change in surface potential is monitored and can be related to the number of adsorbed analyte molecules. Using different surfaces and surface functionalisation techniques, sensitivity to specific target analyte molecules can be achieved with this sensor. For sensing, it is important to include a reference electrode to control the solution potential and to apply the liquid gate voltage.

Conductance in ISFETs is strongly dependent on the charge density at the oxide-electrolyte interface. ISFETs are sensitive towards any electrical fields in general, and to charged molecules in particular. Depending on the point of zero charge of the surface and the pH of the electrolyte a respective surface charge is building up, the charging of the terminal surface groups behaves like a local gate potential. Therefore, it is possible to detect variations in the pH of the solution, i.e. taking or giving away protons at the functional interface is sensed. For the transfer characteristics of the devices, the source drain current ($I_{SD}$) is measured as a function of the applied gate voltage $V_G$. In a semi-logarithmic scale, the steepest slope of the curve $I_{SD}$ vs $V_G$ is defined as a sub-threshold swing with the threshold voltage $V_T$ at which the current is switched on due to the formation of an inversion layer at the insulator-semiconductor interface. At this point the FET switching can happen at maximum speed. By analysing this slope, which is constant over several orders of magnitude, curve shifts at a fixed current due to attached charged molecules can be determined ($\Delta V_T$).

Because of the possible (de)protonation of the surface oxide, pH measurements are usually applied to probe the device performances for potential application in biosensing. By changing pH, the surface potential is directly affected and influences the $V_T$. As a result, the curve of $I_{SD}$ vs $V_G$ shifts to lower or higher voltage values. Sensitivity of ISFETs is thus determined by the maximum possible shift because of a pH change, and defined by the Nernst limit at 300 K, as explained in detail by Tarasov in his PhD thesis "*Silicon Nanowire Field-effect Transistors for Sensing Applications*" (2012).

As most biomolecules display charges at their outer surface, ISFETs are equally sensitive to biomolecules such as proteins or DNA. Thus, their $I_{SD}$ vs $V_G$ curve shifts parallel to the $V_G$ X-axis when the charge density changes, and can be further analysed the same way as described for the aforementioned pH measurements.

Bavli et al (2012) showed a two-dimensional (planar) FET (used as a molecularly controlled semiconductor resistor), run in liquid environment, for the detection of different analytes on a lipid bilayer functionalized surface with a detection limit in the μg/ml range, which clearly indicates that this FET lacks low detection limits. SiNWs are integrated in field-effect transistors (FETs) to build sensor devices with strong signal amplification at low power consumption, which is advantageous for portable or implantable devices. One-dimensional FETs strongly benefit from an extreme surface area to volume ratio, which allows effective channel gating from even just a few adsorbed analyte molecules. SiNW-based FET sensing was described first by Cui et al in 2001 using vapour-liquid-solid (VLS) grown silicon nanowires (SiNWs) for pH sensing and detecting the binding of streptavidin protein on biotin-labelled wires. To date they demonstrated sensing of DNA/PNA hybridisation (Hahm and Lieber 2004), viruses down to single virus detection events (Patolsky et al 2004), using antibodies as receptors, multiplexed sensing (Patolsky et al 2006) and cell potentials (Jiang et al 2012).

SiNW-based FETs used for biosensing belong to the group of ISFETs and therefore operate in liquid medium. SiNWs compared to ISFETs offer higher surface-to-volume ratios for good sensitivity and small cross-sectional conduction pathways. Thus, they can overcome the detection limits of planar ISFETs. SiNW-based FETs have a conductance of 4-10 times higher than planar standard ISFETs of the same sizes due to their high surface-to-volume ratio and the efficient penetration of the gate field.

In biosensing applications of SiNW FETs, as in ISFETs, liquid also acts as a gate electrode and variations in the surface potential are converted to a conductance change in the channel. Actually, different from planar ISFETs, the one-dimensional SiNWs themselves are conduction channels, which are fully affected by the surface potential. Biological recognition events strongly alter the surface potential of the SiNWs even at low analyte concentrations. Charged biomolecules can locally act as liquid gate leading to resistivity changes, which (resistivity) is very sensitive to the biorecognition event. Due to signal amplification by the FET, the signal can be detected by significant jumps in the voltage at a fixed source drain current. Commonly, single-crystalline nanowires are with p- or n-type doping to create charge carriers that are attracted or repelled by the attaching charged biomolecules.

SiNWs can be combined with existing processing technology for silicon wafers to fabricate chips, which reduces the cost of disposable chips. Many groups developed SiNW arrays in top-down fabrication to measure biorecognition events like protein detection using antibodies (Elnathan et al 2012) or hybridisation (G. Zhang et al 2008). In order to use these devices as biosensors, the silicon dioxide ($SiO_2$) surface of SiNWs should be functionalised with biorecognition elements in a controllable manner.

For all the different applications, interface engineering and chemical functionalisation of the transducer ($SiO_2$) surface are crucial for biosensor development to assure an excellent sensor performance. Requirements are a stable receptor attachment under varying conditions while preserving the functionality of receptors at the same time. Additionally, binding strategies will enhance the receptor orientation towards the target in solution whereas blocking protocols try to avoid unspecific attachment to reduce background signals. The main focus here is on chemical functionalisation of silicon dioxide surfaces of SiNWs and evaluation of the receptor-analyte interactions with the immobilised receptors using optical and electrical sensing methods using the SiNW-based FET.

Real-time, label-free, portable, low-cost, flexible and reliable sensors with lab on chip systems are long-needed biomedical diagnostic devices, and they are still challenging. Further requirements to evaluate novel biosensors are their sensitivity to detect low levels of the analyte, selectivity to avoid false positive signals and a fast response time that allows for rapid diagnosis. In terms of fabrication, the integration into existing technologies and production, the versatility of application and the possibility to produce at low costs are crucial. Reversibility of the biosensor would allow for repeated measurements to improve comparability.

Integration of nanomaterials into biosensor's transducer is one of the possibilities to meet some of the above listed requirements especially in terms of miniaturisation and sensitivity due to their high surface-to-volume ratio and the confinement within the nanometer scale in at least one dimension which leads to changes in the physical properties. SiNW based FETs fulfil many of these requirements. The use of nanomaterials and the possible integration into Si wafer processing technology enables miniaturisation of devices at low costs. The immediate current jump upon physicochemical changes without need for analyte labelling meet the requirements for the modern biosensor of being real-time and label-free.

To improve stability of the existing sensor arrays and ensure reproducibility of the readout, the sensors of some of the disclosed embodiments are fabricated in a parallel batch process on standard Si wafers. To enable a control in bioassays, reference sensor structures such as temperature sensors, pH sensors, and ionic strength sensors are added to the sensor chip. As discussed below, the design of the pixel array in a three-electrode configuration including a reference electrode and a counter electrode enables an additional operation of the nanoelectronic sensor pixel in the frequency domain and helps to stabilise the electronic readout when recording very small DS current changes. Therefore the sensors of some of the disclosed embodiments can be also used for impedance spectroscopy applications. A combination of potentiometric and impedimetric readout enables a more reliable sensing of biomolecules with the potential to sense beyond the Debye screening of electrical charges in an electrolyte solution, which is usually the limiting factor in SiNW sensors having only potentiometric or conductometric readout.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

SUMMARY

In one embodiment, the present application provides an electrical circuit element, defined as "pixel", comprising at least one silicon nanowire open for contact with a medium for sensing; a metal electrode open for contact with said medium and used for feeding a high-frequency sinusoidal stimulation in impedance measurements and for sensing properties of said medium; implanted source and drain electrodes connected to said silicon nanowire and leaving the gate area and parts of said electrode open for contact with said medium; electrical metal contacts for connecting said pixel to an electrical circuit; and a reference electrode open for contact with said medium for creating a three-electrode-cell system and providing a constant gate potential in the circuit. In another embodiment, the present application provides a microelectronic sensor and wearable-patch sensor based on the array of these pixels. In yet another embodiment, the present application also provides methods for performing DC readout, AC readout and a triple readout combining both DC and AC readouts and temperature sensing.

BRIEF DESCRIPTION OF THE DRAWINGS

Disclosed embodiments will be understood and appreciated more fully from the following detailed description taken in conjunction with the appended figures.

DETAILED DESCRIPTION

In some embodiments. the present application provides a sensor pixel incorporating a top-down fabricated silicon-nanowire (SiNW), the pixel array and a nanoelectronic sensor chip based on this array. A huge advantage of the present sensor pixel is that it contains integrated additional electrodes for additional sensing capabilities, which also allow applying a triple readout method based on the combined transducer principle, as will be described in details in the present application.

There are two main methods to fabricate single-crystalline SiNWs: bottom-up and top-down growth of the nanowire. In the bottom-up approach, single-crystalline SiNWs are grown with vapour-liquid-solid growth method (VLS). This approach is technologically much easier, but a scale up for industrial fabrication and mass production is not feasible. Although the bottom-up method produces very thin and sensitive wires in the range of 10 nm, it has a low reproducibility. In fact, bottom-up approach has thus far prevented the commercialisation of such nanowire sensors mainly due its incompatibility with reproducible, high-volume manufacturing. In contrast, various top-down methods entail a high level of non-standard processing complexity and high process variation.

The SiNW arrays of disclosed embodiments are therefore fabricated using a top-down method, which has the advantage of producing more robust transistors. In addition, this approach addresses the problems of placement, integration, and reproducibility encountered with bottom-up materials. The modified top-down method, which was developed by the present inventors and described in Vu et al (2009 and 2010), combines wafer-scale nanoimprint lithography techniques defining nanowires from thin single crystalline silicon layers, reactive ion etching and further etching with tetra methyl ammonium hydroxide. After nanowire array fabrication, source and drain are doped by ion implantation to form electrode contacts, gate oxide is grown to create the gate dielectric layer, metal contacts are defined, and finally everything except the wire regions is passivated for sensor use in liquids.

The advantages of the top-down devices compared to those implementing bottom-up grown nanowires are the precise definition of the nanowire arrays on certain areas and the predetermined number of the nanowires on one device, which significantly increases the reproducibility.

SiNW Arrays and Prototype Devices

Figures 1A, 1B:
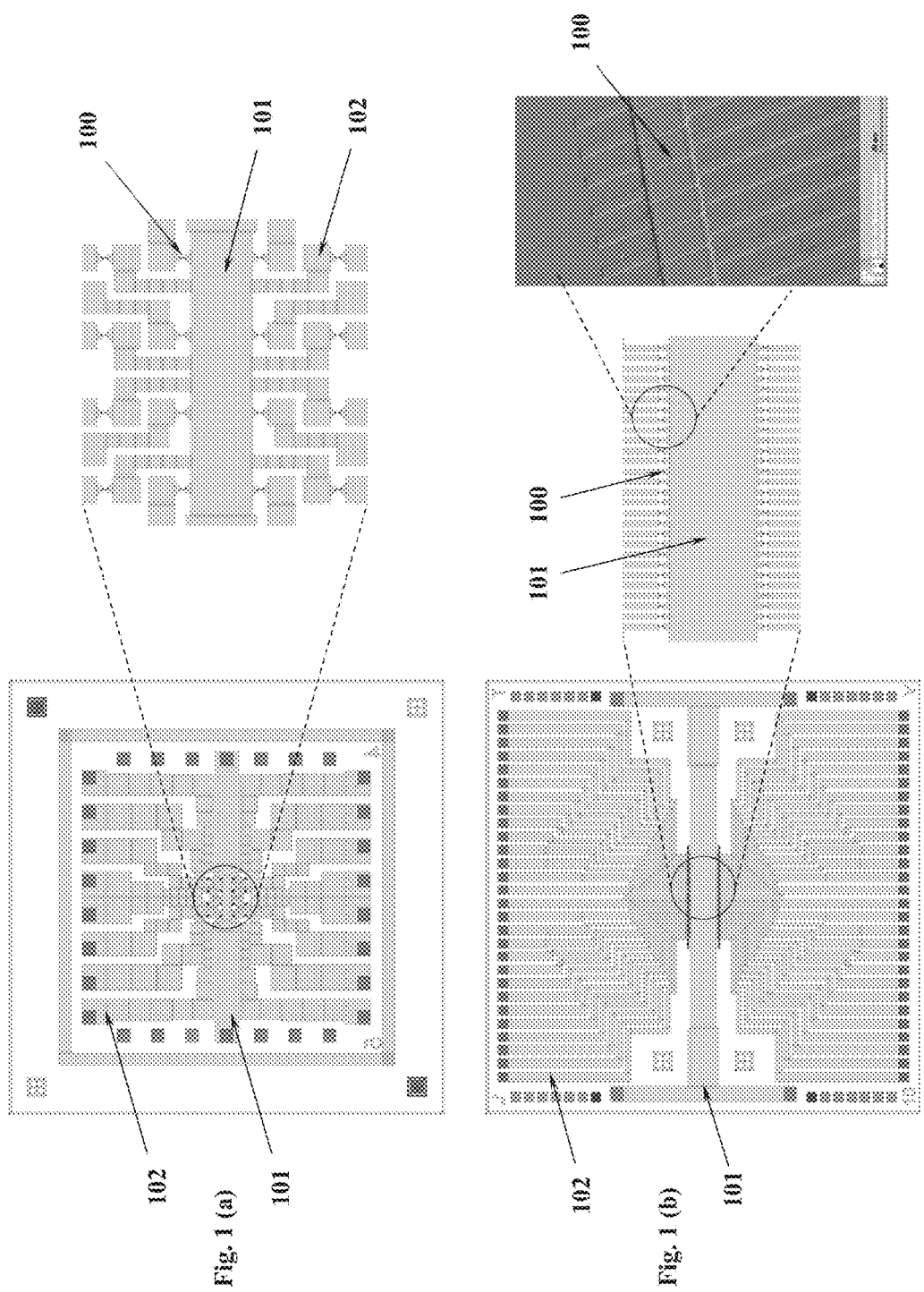
FIG. 1(a) shows an exemplary design of the 4×4 SiNW array.
FIG. 1(b) shows an exemplary design of the 28×2 SiNW array.

FIG. 1 shows examples of 4×4 and 28×2 SiNW arrays recently produced by the top-down fabrication method. Each SiNW corresponds to a single sensing channel. Therefore, the terms "SiNW" and "channel" can be used interchangeably. FIG. 1(a) shows the actual design of the 4×4 array containing single nanowire (100) of 5 µm in length and 400 nm in width, in each channel, with a pitch of 200 µm. There are 16 drain contact leads (102) and one common source contact lead (101).

FIG. 1(b) further shows the second design of the 28×2 array containing 28 single nanowires (100) of 5 µm, 10 µm, 20 µm and 40 µm in length and 200 and 400 nm in width, and having one common source (101) and 56 drain contact leads (102). The pitch between two lines is 500 µm for all the 28×2 arrays type. On a specific chip, the length of the wires (in µm) is indicated at the left bottom corner and the width (in nm) is indicated at the right bottom corner. The SEM image on the right shows the single parallel nanowires (100) between the source and drain of the 28×2 array. An open gate area is formed between the source and drain contacts.

The "open gate area" of the SiNW ISFET is defined as an area between the source and drain contacts of the transistor, which is directly exposed to a conductive medium, such as liquid or gas, capable of conducting electric current. An example of the conductive liquid is an electrolyte saline solution or buffer. In this case, instead of the fixed gate voltage, which is normally applied to a gate electrode, a reference potential is applied to the electrolyte-semiconductor system, via a reference electrode that is contacting the electrolyte. As a result, in the absence of the physical gate, the electrolyte itself becomes an open gate of the transistor.

Figure 2:
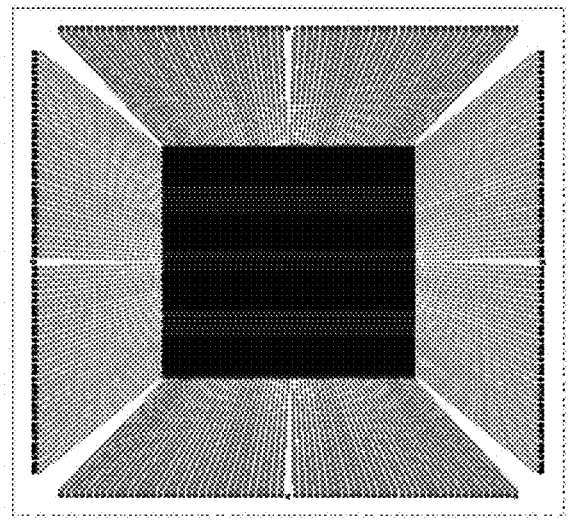
FIG. 2(a) shows a design of the 128×128 SiNW array.
FIG. 2(b) shows the SEM image of the 128×128 SiNW array.
FIG. 2(c) shows the SEM image of a single channel in the 128×128 SiNW array.
FIG. 2(d) schematically shows a single channel of the 128×128 SiNW array.
FIG. 2(e) schematically shows a single SiNW of the 128×128 SiNW array.
Figure 2:
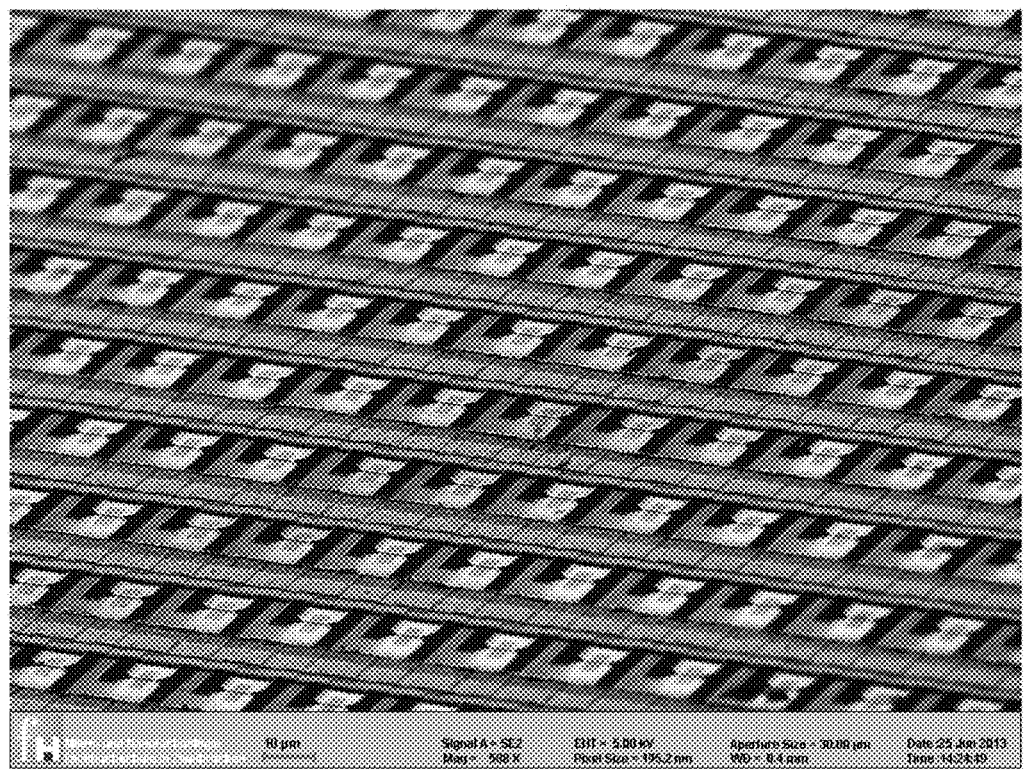
Figure 2:
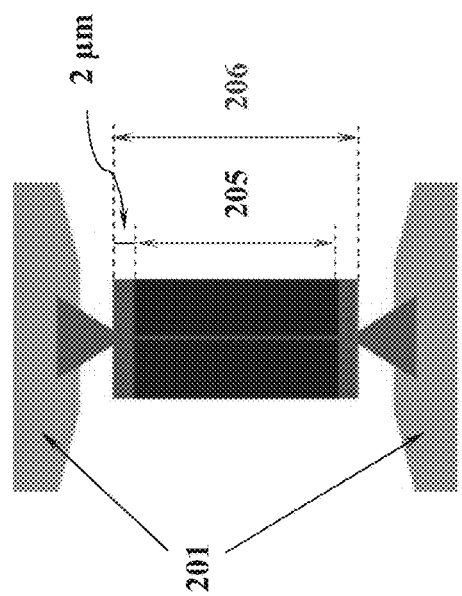
Figure 2:
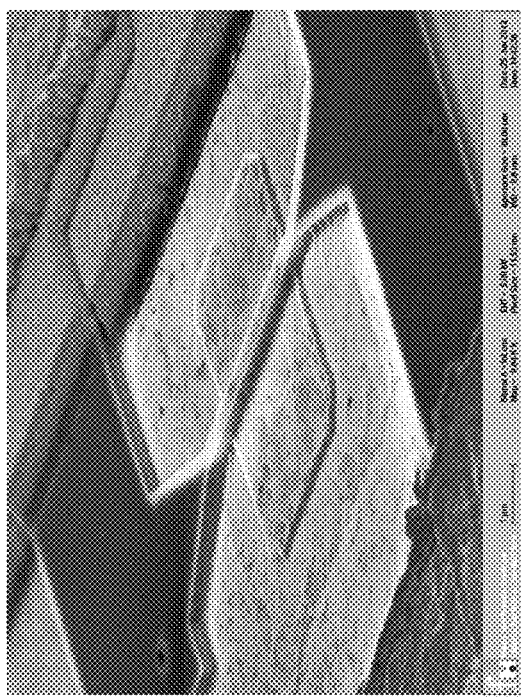
Figure 2:
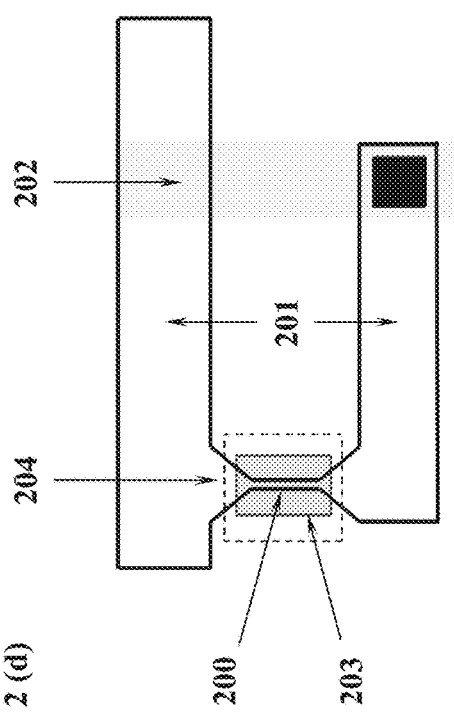

FIG. 2(a) schematically shows the design of a 128×128 array (16384 channels) with a 25-µm pitch. The SEM image of this array is shown in FIG. 2(b), while a single channel in this array is schematically shown in FIG. 2(d) and its SEM image is shown in FIG. 2(c). The SiNW (200) is grown between the implanted source and drain (201) using mask (203) to form self-aligned source and drain regions, and opening (204) for passivation. Metal feed line (202) connects the single channel with the array circuit. FIG. 2(e) schematically shows a single SiNW of this array. The source and drain contacts (201) are highly ion-implanted. The non-implanted area (205) is shown in dark blue. The nanowire is the same lowly doped silicon as the original SOI wafer. The open gate area (206) is 2 µm larger than the non-implanted area from each side of the nanowire.

Figure 3:
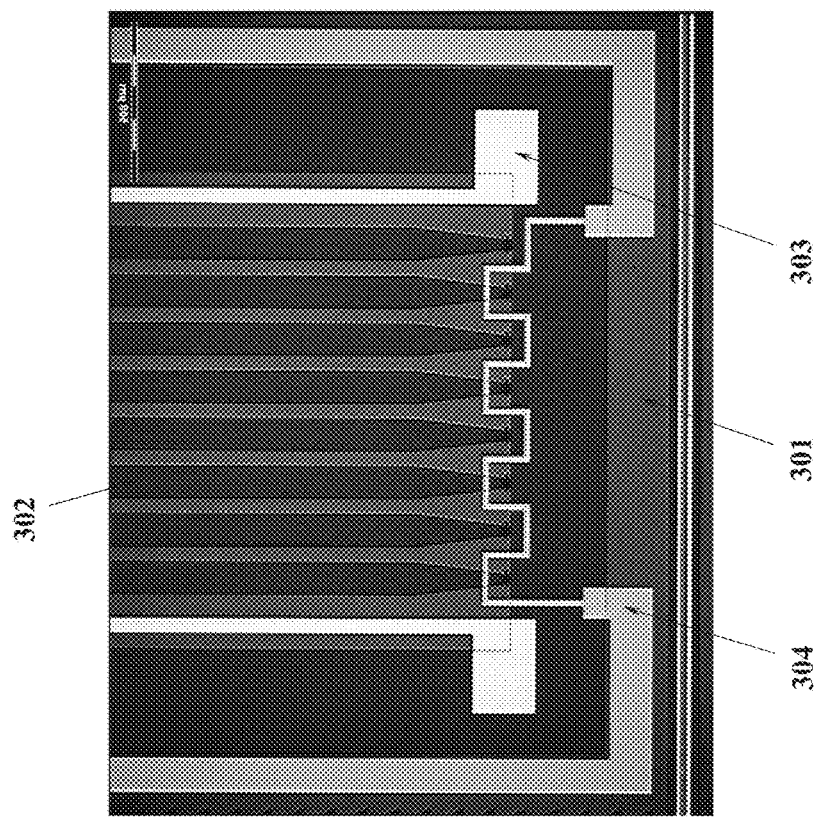
FIGS. 3(a)-(c) schematically show the layout of an 8-channel SiNW ISFET sensor chip with a triple functionality readout embedded on the chip.
FIGS. 3(d)-(e) show the optical microscopy images of an 8-channel SiNW ISFET sensor chip completely fabricated at the inventor's facility.
FIGS. 3(f)-(g) shows the actual 8-channel SiNW ISFET sensor chip of an embodiment.
FIG. 3(h) demonstrates the steps of the sensor integration process.
Figure 3:
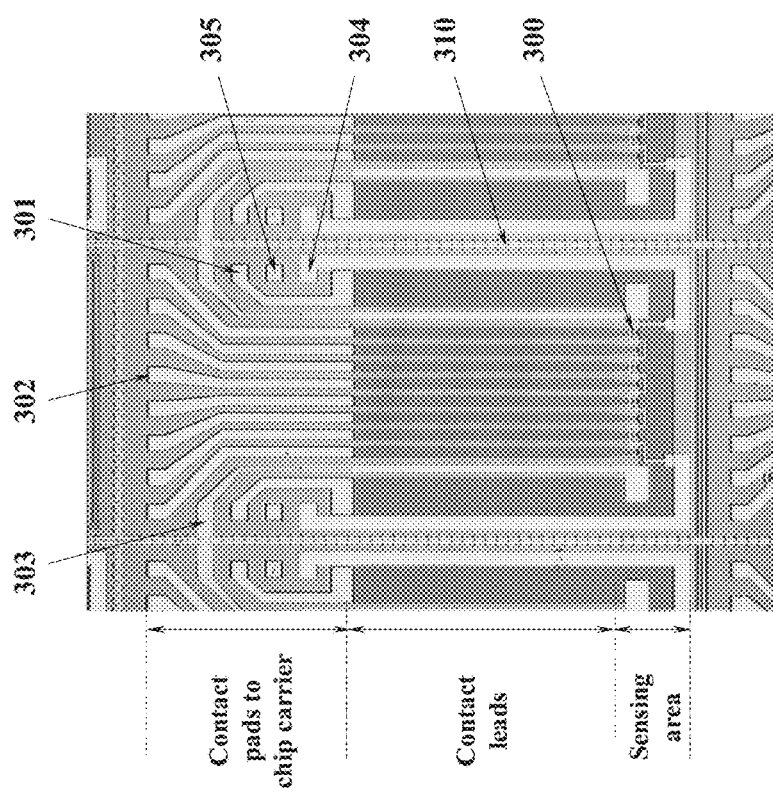
Figure 3:
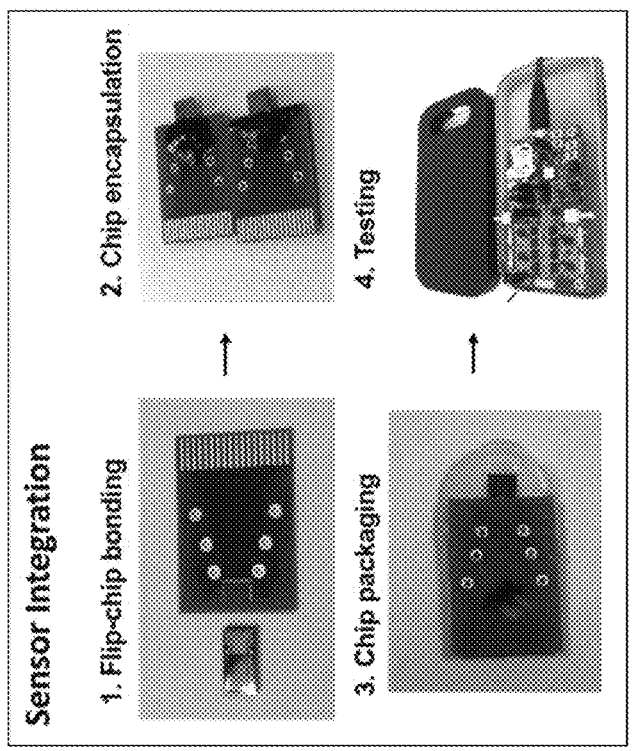
Figure 3:
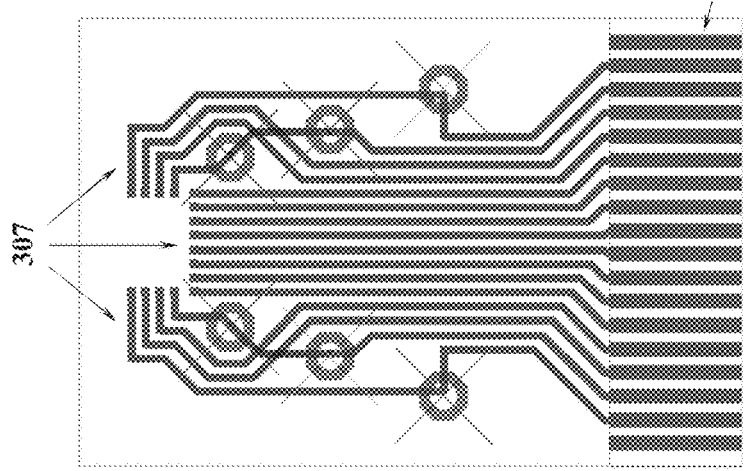
Figure 3:
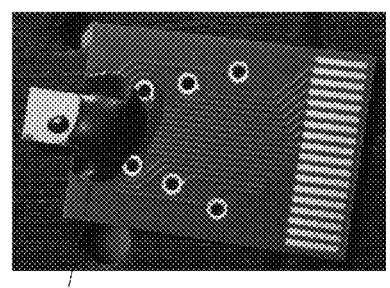

FIGS. 3(a)-(c) show the layout of the 8-channel SiNW ISFET chip with a triple functionality readout embedded on the chip. This chip served as a prototype for the sensor pixel chip of an embodiment. Similar to the above arrays, this sensor chip also consists of contact leads arranged in different arrays. At one end of the chip, silicon nanowires (300) are placed between source (301) and drain (302) contact leads. As an example, distance A from channels to bottom line in this chip is 520 µm±25 µm, while distance C from the first or last channel to an edge of the chip is 750 µm±25 µm, and distance B between the neighbouring channels of this particular chip is 150 µm±2 µm.

Through the common source (301) and eight individual drain contact leads (302), the different SiNWs can be addressed. The chip further contains reference electrodes (303), which are used to apply a stable liquid potential for gate bias. In addition, the chip contains a common metal electrode (304), which can be used as a counter electrode, a temperature sensor microelement or an input for high-frequency AC sinusoidal stimulation in the impedance measurement. Also, there are back gate contacts (305) to connect the back gate of the transistor (i.e. the silicon handle wafer below the buried oxide layer) to the circuit in order to tune the working point of the front gate and keep the potential of the bulk silicon stable during measurements. Further, an optional microfluidic flow cell (306) for analyte delivery to the chip may also be added to the chip.

In one aspect of the disclosure, according to FIGS. 3(a)-(c), the SiNW ISFET sensor chip comprises an array of:
- silicon nanowires (300) connecting a common source electrode contact lead (301) with individual drain electrode contact leads (302) and conducting electrical current between the source and drain electrodes in a circuit;
- reference electrode contact leads (303) placed between said source and drain electrode contact leads, thereby creating a three-electrode-cell system and providing a constant potential in the circuit;
- a metal electrode contact lead (304) for feeding the high-frequency AC stimulation in impedance measurements and for sensing external parameters of said chip; and
- back gate contacts (305) connecting the back gate of the transistor to the circuit for tuning the working point of the front gate and keeping the potential of the bulk silicon stable during measurements.

In another embodiment, the SiNW ISFET chip further comprises a flow cell (306) for analyte delivery to the chip. The chip can be scalable-manufactured on 2-20 inch silicon wafers using the top-down method, as mentioned above. The 4-inch silicon wafer contains, for instance, 500 chips with 300 chips in the centre of the wafer. The fabricated chips have a size of 2.5×5 mm which can be varied dependent on a particular application. The reference electrodes (303) are integrated on the chip in an additional metallization step of the top-down fabrication. There can be one, two or more reference electrode leads (303) printed on the chip. They can be connected together or used separately. The reference electrode leads (303) are printed on the chip as Ag electrode leads and then chlorinated to obtain the Ag/AgCl reference electrodes. It is well known that the Ag/AgCl system can only be regarded as a pseudo-reference system, since it will be very dependent on the chloride concentration. However, in combination with an ionic-strength sensor in the pixel array, this side effect can be avoided.

In a particular embodiment, the metal electrode (304) is a noble metal electrode, such as platinum counter electrode. In another particular embodiment, the metal electrode (304) is a temperature sensor. In yet further embodiment, the metal electrode (304) is used for the high-frequency AC sinusoidal stimulation in the impedance measurement of the sensor. In a specific embodiment, the metal electrode (304) is used as a counter electrode and temperature sensor, simultaneously. This functionality requires a specific switch being installed in the electronic readout module in order to select the operational mode of the metal electrode (304), either as a counter electrode or as a temperature sensor during the measurements. This enables a stable readout and cancels out temperature effects during recordings.

In another embodiment, the microfluidic flow cell (306) comprises a microfluidic chamber having inlet and outlet for a fluid circulating through the chip and delivering the analyte to the SiNWs (300) in a continuous flow. The SiNW ISFET can operate with both back gate and front gate. The back gate electrodes (305) are used to tune the working point of the front gate. They also have a function of keeping the potential of the bulk silicon stable during experiments.

The lowly-doped SiNWs (300) can be of n-type or p-type, or can be configured as tunnelling silicon nanowire devices (drain n-doped and source p-doped or drain p-doped and source n-doped), and the SiNW ISFET can be operated as p-type transistor or n-type transistor depending on the doping and on the applied voltages to the gate. Generally, in contrast to back-gate operation, the electric signals of the front-gate operations were stable and reliable. A subthreshold slope of 90 mV/decade indicated that a high quality front-gate oxide was achieved in the fabrication process, which can enhance the sensitivity of the SiNWs devices.

FIG. 3(d)-(e) show optical microscopy images of 8-channel SiNW ISFET sensor chip described above and used in the preliminary experiments. As seen in these figures, contacts of the reference electrode (303) are connected via cutting lines (310) of the chip for a wafer-scale chlorination of the Ag/AgCl electrode system.

FIGS. 3(f)-(g) demonstrate the actual 8-channel SiNW ISFET sensor chip completely fabricated at the inventor's facility. Contact pads (307) are available for flip-chip bonding of the chip, while contacts (308) are used for connecting the chip to a circuit via a flat flexible connector (FCC). A sensor-integration process, which is shown in FIG. 3(h), comprises the steps of: 1) flip-chip bonding, 2) chip encapsulation, 3) chip packaging, and 4) chip testing. As an example, the 2.5 mm×5 mm chips were cut from the fully-processed silicon wafer and then cleaned with acetone and isopropanol in order to remove the protection resist. Due to the mechanical properties of the SiNW, the cleaning steps needed to avoid strong mechanic treatment like ultrasound or mechanical manipulation.

The electrical contact between the bond pads on the chips and the carriers was formed by printing of a two-component conductive silver glue (309), for example Epo-Tek H20E-PFC, (PolytecGmbH, Waldbronn, Germany), on the contact areas of the carrier using a screen printer, such as SP-002 (Essemtec AG, Aesch, Switzerland). Then the chips were mounted to the back side of the printed circuit board carriers (WI-KA GmbH, Baesweiler, Germany) by flip-chipping using a precise X-Y positioning system, such as Fineplacer 96 (Finetech GmbH & Co. KG, Berlin, Germany). The glue was cured at 150° C. for one hour. Followed by application of a two component under fill epoxy, such as Epo-Tek U300, Polytec, or epoxy resin, such as Epo-Tek 302-3M, Polytec, around the chip. Due to its viscous properties, the epoxy was dragged between the chip and the carrier, thus insulating everything but the bond contacts electrically. The epoxy was then cured at 150° C. for 1 hour. Finally, a small glass ring was glued on the carrier to form an electrolyte reservoir for initial testing of the sensors.

Pixel

Figure 4:
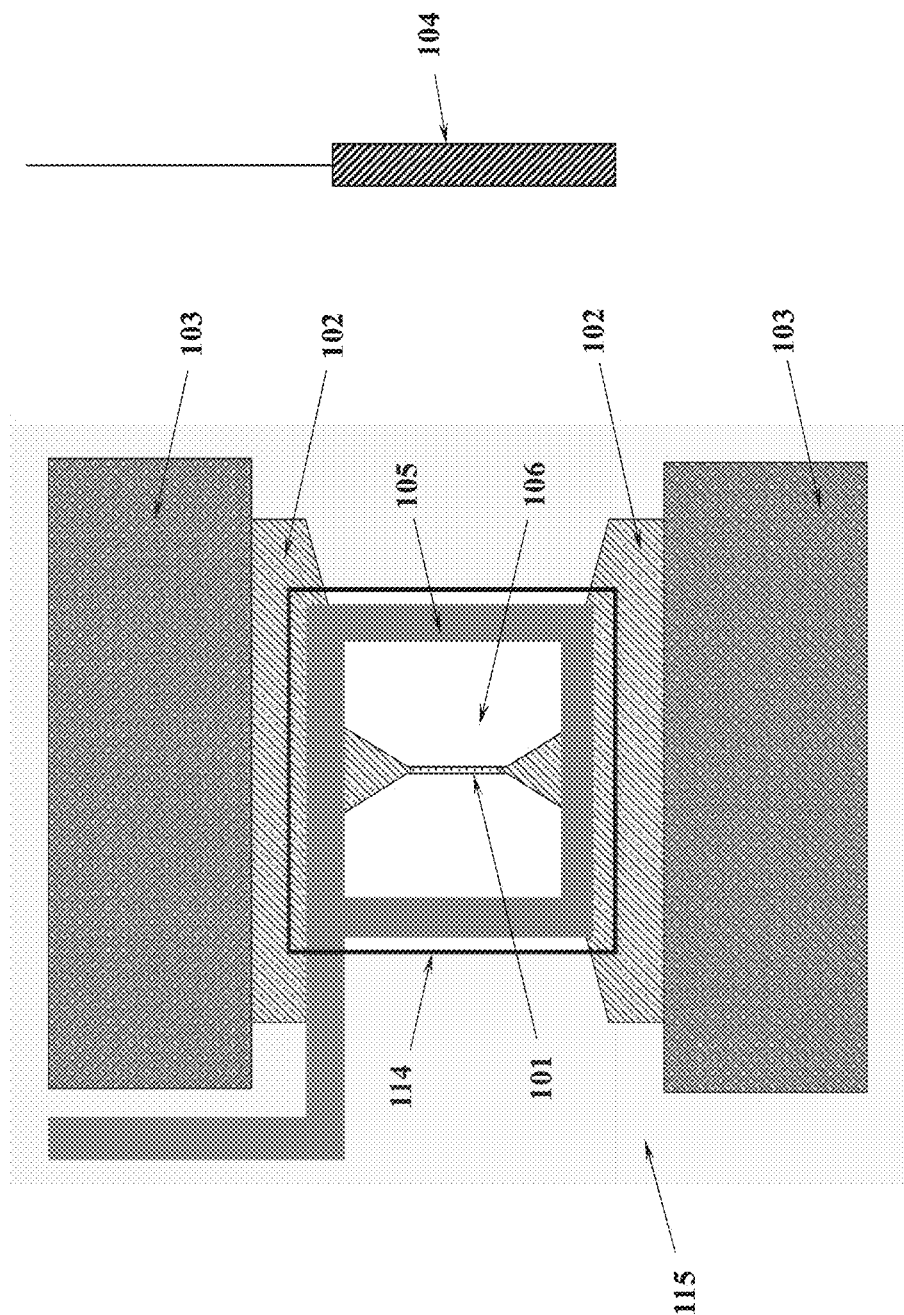
FIG. 4 schematically shows the pixel of an embodiment.

As defined herein, a "pixel", shown in FIG. 4, is an electrical circuit element comprising:
- one or more silicon nanowires (101) open for contact with a medium, such as an ionic liquid or gas, for sensing;
- a metal electrode (105) open for contact with said medium for feeding the high-frequency sinusoidal AC stimulation in impedance measurements and for sensing properties of said medium;

implanted source and drain electrodes (102) connected to said silicon nanowires (101) and leaving the gate area (106) and parts of said electrode (105) open for contact with said medium;

electrical metal contacts (103) for connecting said pixel to an electrical circuit; and a reference electrode (104) open for contact with said medium for creating a three-electrode-cell system and providing a constant potential in the circuit.

In a particular embodiment, the silicon nanowires (101) are lowly-doped, etched from the top silicon layer of prime-quality silicon-on-insulator (SOI) wafers, which allows high carrier mobility, thereby improving performance. The source and drain electrodes (102) are highly doped, in order to reduce feed line resistance, and etched from the same silicon layer of the SOI wafer in the same process step. The contact leads material is highly-doped silicon, a highly-doped polysilicon layer, a metal layer or preferably, a silicide, such as CoSi, PtSi or TiSi.

In a specific embodiment, the metal electrode (105) is a noble metal electrode, such as platinum counter electrode, which can also be used as a temperature sensor. In a further specific embodiment, the metal electrode (105) is used as a counter electrode and temperature sensor simultaneously. In yet further embodiment, the metal electrode (105) is used for the high-frequency AC sinusoidal stimulation for the impedance measurements of the sensor. In a particular embodiment, the reference electrode (104) is an Ag/AgCl reference-cell electrode. The metal electrode (105) is chosen according to an established technology and an assembly line at a particular clean room fabrication facility. The metal electrode (105), as well as the reference electrode (104), is not passivated since they both should be in direct contact with the tested medium. Therefore, there is an opening (114), which is made in the passivation layer (115), for leaving the sensing elements of the pixel open to the medium. As will be shown below, the actual sensor will include many pixels in an array, one common metal electrode and one common reference electrode for all the pixels.

The electrical metal contacts (103) contacting the silicon source and drain connect the pixel to the electrical circuit and allow the electric current to flow in the system. One layer of these contacts is made of aluminium or silicide, such as CoSi, PtSi or TiSi, in order to form a surface alloy with the silicon, thereby providing an electrical ohmic contact to the silicon. The term "ohmic" contact means that it has a straight line in the current-voltage characteristics. These ohmic metal contacts (103) are made of metal or metal stacks, such as Al, Al/Ti/Au or similar. Another layer of these contacts is not contacting silicon and used to promote adhesion to the underlying layers of $SiO_2$ and $Si_3N_4$, which are used for isolation. Cr and Ti are examples of such adhesion promoters. The Cr or Ti layers of the metal stack is, for example, of 5-10 nm thickness, while the second metal layer, such as Au, Pt and Cu, is of 100-400 nm thickness. In order to limit the capacitive coupling of the source and drain contact leads and to avoid leakage current into the signal of the sensor, the source and drain contact leads are further covered by a thick layer of insulators.

Figure 5A:
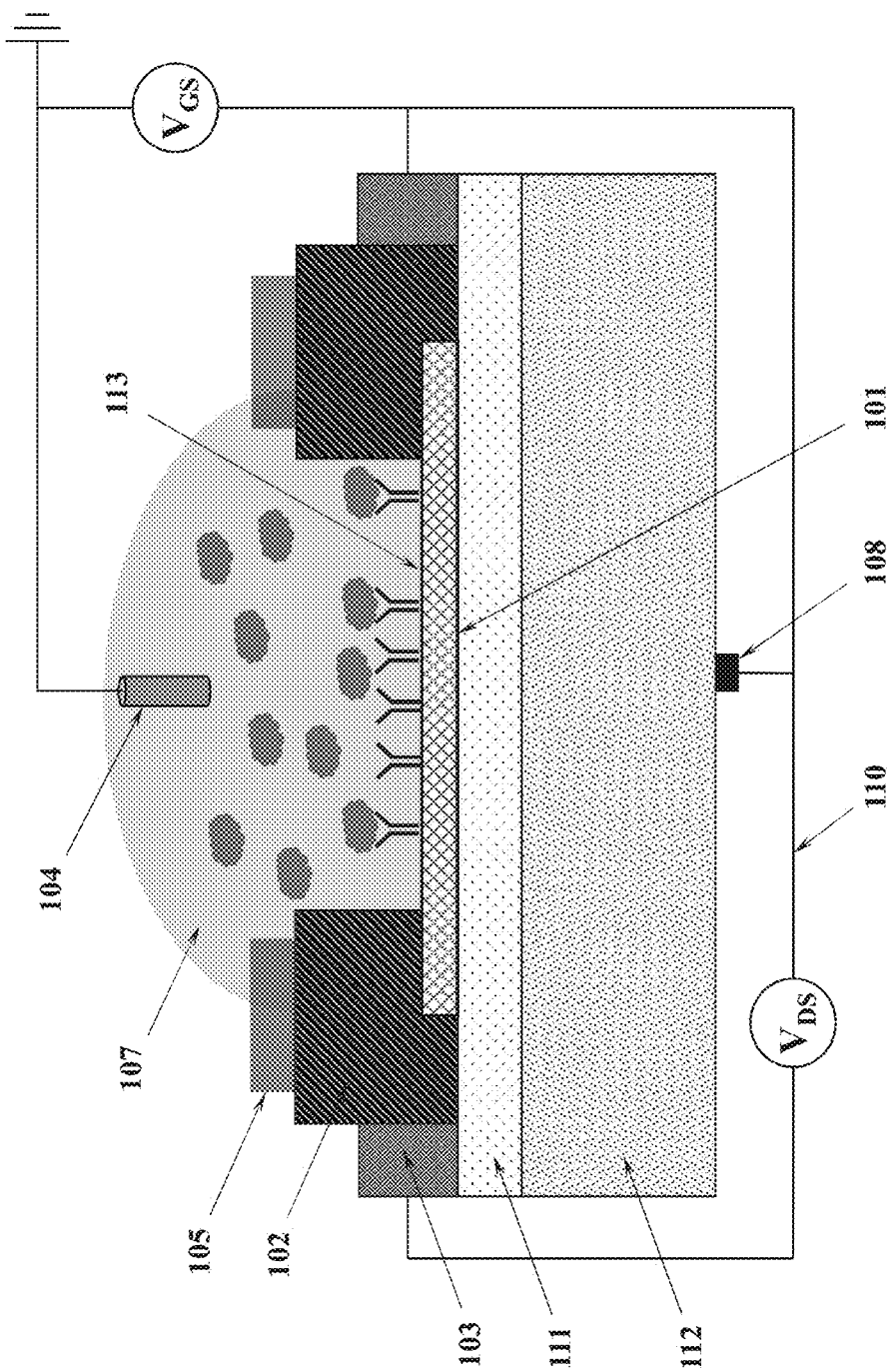
FIG. 5(a) schematically shows the cross-section of the pixel sensing a liquid sample, which contains analyte molecules.

FIG. 5(a) shows the cross-section of the pixel sensing a liquid sample (107), which contains analyte molecules. The pixel is connected to the circuit (110). As noted above, the pixel is manufactured using the modified top-down approach from SOI wafer substrates (112) with about 40-60 nm in thickness of the top silicon layer and a silicon buried oxide (BOX) (111) of approximately 100-400 nm thickness, which acts as an insulator layer. At room temperature and under the assumption that no fixed oxide charges exist, the SiNW (101) is fully depleted of charge carriers in thermal equilibrium. The pixel may further comprise a back gate (108) at the bottom of the handle wafer substrate (112). The back gate is used for tuning the threshold voltage, since the body of the pixel influences that voltage.

The open gate formed by liquid or gas medium (107) effectively controls the charge flow in the SiNW channel. In the gate area (106) (from FIG. 4), the SiNW (101) is coated with a gate oxide (113), which is placed in between the source and drain electrodes (102), and acts as a channel to allow the flow of charge carriers from one electrode to another. This is particularly useful for DC sensing. The gate oxide, also called the gate capacitor or dielectric (113), is a thin layer of oxide or nitride dielectric material, such as $SiO_2$, $Al_2O_3$, $TaO_2$, $HfO_2$, $TiO_2$, $ZrO_2$, TiN, $Si_3N_4$, or similar. It is grown on top of the silicon substrate between source and drain, protecting the surface of the SiNW from an electrolyte solution, acting as a capacitor for the field effect and providing good pH sensitivity. In case of $TaO_2$ or $Al_2O_3$, it is an almost ideal pH sensor.

In case of $SiO_2$, the gate oxide (113) has a preferable thickness of 6-8 nm and isolates the SiNW from an electrolyte. The BOX layer (111) of approximately 100-400 nm thickness separates the SiNW from the handle wafer substrate (112) of about 500 μm thickness. Hence, the concentration of charge carriers in the nanowire can be controlled by an electric potential that can either be applied from the top through the thin oxide layer (113) or from the bottom through the thick BOX layer (111). The first gate is called "front gate" (FG), while the second is called "back gate" (BG). Like in any SOI fully-depleted device with a very thin top silicon layer, both gates are strongly coupled electrostatically. This indicates that the back-gate potential affects the front-gate characteristics and vice versa.

Thus, depending on application purposes, the gate surface of the pixels can be further modified by depositing other materials on the oxide layer, such as $Si_3N_4$, $SiO_2$ or similar listed above, for pH sensors, monolayer of polymer for biomolecular binding, or high-k materials to enhance the electronic coupling with biology systems. The gate area (106) can also be a metal layer contacting a SiNW and being exposed to the tested medium. In a particular embodiment, the surface of the SiNW (101) is coated with a metal, such as Au, Pt or Cu, or by a molecular passivation layer, to become pH-insensitive and serve as a solution conductivity reference element (for pure ionic strength sensing).

The passivation process can be carried out by the method of atomic layer deposition (ALD) of the gate oxides, which are deposited directly on the SiNW surface. These gate oxides are excellent sensing interfaces due to high density of their active surface groups obtained in the surface activation process prior to surface functionalisation. The front gate voltage is applied through a reference electrode immersed in electrolyte solution on top of the gate oxide or by a surface-engineered reference electrode on chip. Thus, the thick passivation layer on the contact leads is necessary for a reliable operation of the sensor in different electrolyte solutions as well as to avoid interfering with the signal at the gate oxide.

For operating the pixel, a front gate voltage ($V_{FG}$) is initially applied by a reference electrode (104), such as Ag/AgCl electrode, which is needed for the front gate contact to keep the electrochemical potential drop over the electrode-electrolyte interface stable (as a result, to keep the electrochemical potential of the solution stable) and the readout signal reliable. The reference electrode (104) actually is set to ground potential in the electronic configuration of an embodiment, and the source and drain potentials are applied at the respective contacts in the circuit.

When a sufficient bias potential is applied to the front gate with respect to the back gate (108), an electric current is immediately induced in the SiNW (101) between the source and drain electrodes (102). The magnitude of the drain current is determined by an effective electrical conductance of the SiNW and the voltage applied between the source and drain electrodes ($V_{DS}$). The conductance of the SiNW between the source and drain is modulated by the current at the gate (reference electrode).

Figure 5:
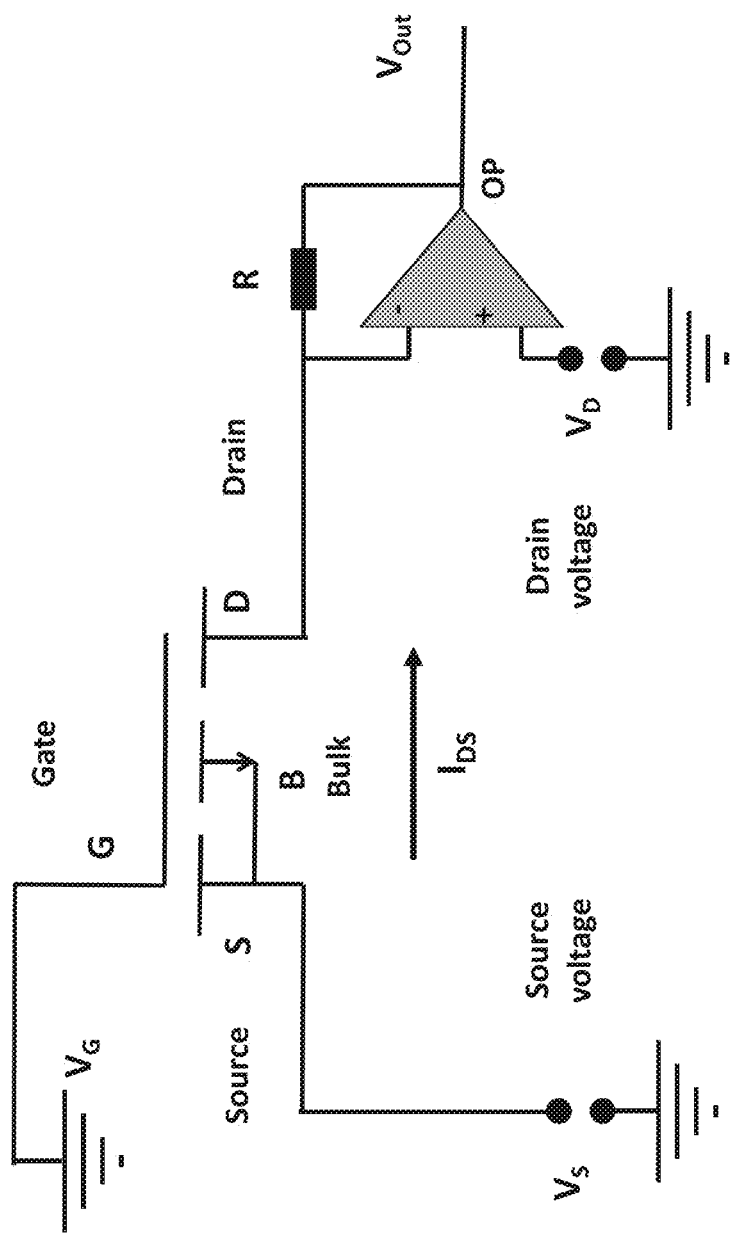
FIG. 5(b) showing an accumulation mode field-effect transistor in a transimpedance amplifier circuit having the electrolyte gate at ground potential.

Reference is now made to FIG. 5(*b*) showing an accumulation mode field-effect transistor in a transimpedance amplifier circuit, wherein the transimpedance amplifier includes an operational amplifier (OP) and a resistor. The transistor is brought into its working point by applying drain-source $V_{DS}$ and gate-source $V_{GS}$ voltage. The transistor is configured such that the gate contact is at ground potential. Therefore the source voltage $V_S$ and the drain voltage $V_D$ are applied. These can be converted by:

$$V_{GS} = -V_S \text{ and } V_{DS} = V_D - V_S$$

Thus, the voltage sources $V_S$ and $V_D$ (while $V_G$ is at ground) are linked together to result in voltage differences $V_{GS}$ and $V_{DS}$, which are usually plotted for the transfer characteristics. In the transistor working point, the drain-source current $I_{DS}$ is flowing through the device. This is converted into a output voltage $V_{out}$ by the operational amplifier (OP), while the amplification factor F is set by the feedback resistor R. The OP is connected at its inverting amplifier input (−).

Transconductance ($g_m$) is an electrical characteristic relating the current through the output of a device to the voltage across the input of a device. It is defined as the ratio between output current to input current. However, it is also frequency-dependent and can be described as follows:

$$g_m(j\omega) = \frac{\partial I_{DS}(j\omega)}{\partial V_{GS}(j\omega)} = \frac{i_{DS}(j\omega)}{v_{GS}(j\omega)},$$

wherein $\omega$ is the angular frequency, j is the imaginary unit, $i_{DS}$ is a small-signal drain-source current and $v_{GS}$ is a small-signal gate-source voltage.

Thus, the total amplification of this first amplifier stage is given by the product of the transistor's transconductance ($g_m$) in the respective working point and the feedback resistor:

$$F = g_m \times R.$$

The SiNWs produced by the top-down process are usually treated as long-channel ISFETs of nano size. The sensing mechanism of these SiNW ISFETs is based on the accumulation of charged molecules near the SiNW surface, which leads to a surface potential shift. The transistor then responds to changes in the surface potential with a threshold voltage shift. While in MOSFETs, the metallic gate is in direct contact with the dielectric over the channel, in the ISFETs, the gate (reference) electrode is a distance away from the dielectric, with an intervening sample fluid. Changes at the dielectric-solution interface alter the surface potential, which acts as an additional gate voltage. The gate voltage $V_{GS}$ is applied using a reference electrode to set the operating point of the device, and the conductance of the channel is measured by applying a drain-to-source voltage $V_{DS}$. Thus, the gate voltage actually modulates the current between the source and the drain.

Pixel Arrays and Sensors

Figure 6:
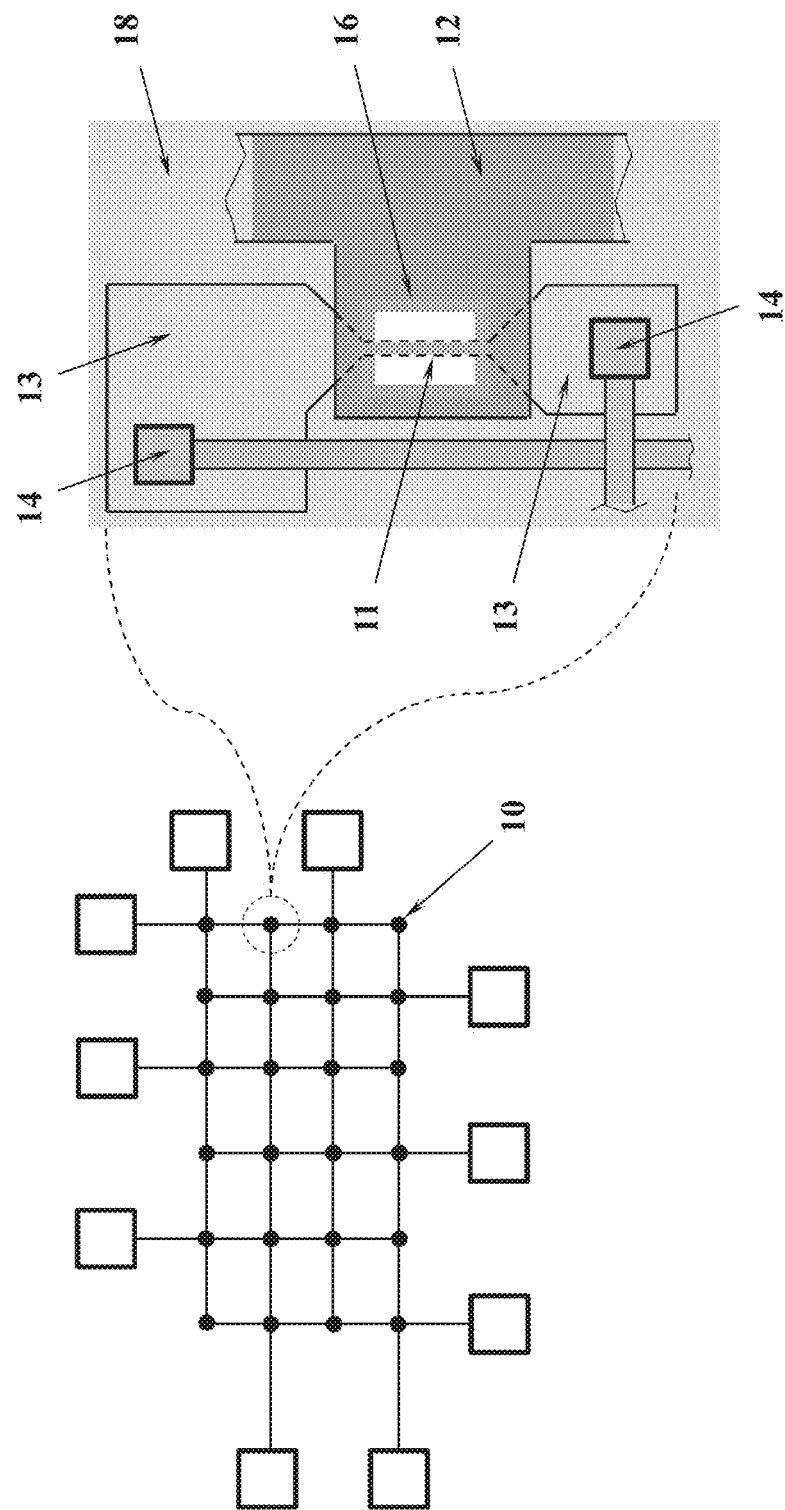
FIG. 6 schematically shows a mixed analogue/digital amplifier circuit comprising an array of the pixels on a sensor chip.

FIG. 6 shows an array of the pixels (10) on a sensor chip. Each pixel comprises one silicon nanowire (11) exposed to liquid or gas medium for sensing, with the implanted source and drain (13) and their contact leads (14) connecting this SiNW to the circuit, and one common metal electrode (12) for feeding the AC sinusoidal stimulation and for conducting sensing or testing operations. A reference electrode (not shown) to set the DC bias voltage $V_G$ in the electrolyte is placed outside. All the pixels in the present array operate synchronously having the same transfer characteristics, as will be shown in the Examples. Therefore, it is essential to set all the gate contacts at a common ground potential (which is the reference electrode potential) in order to operate all the pixels in the array at the same time.

Figure 7:
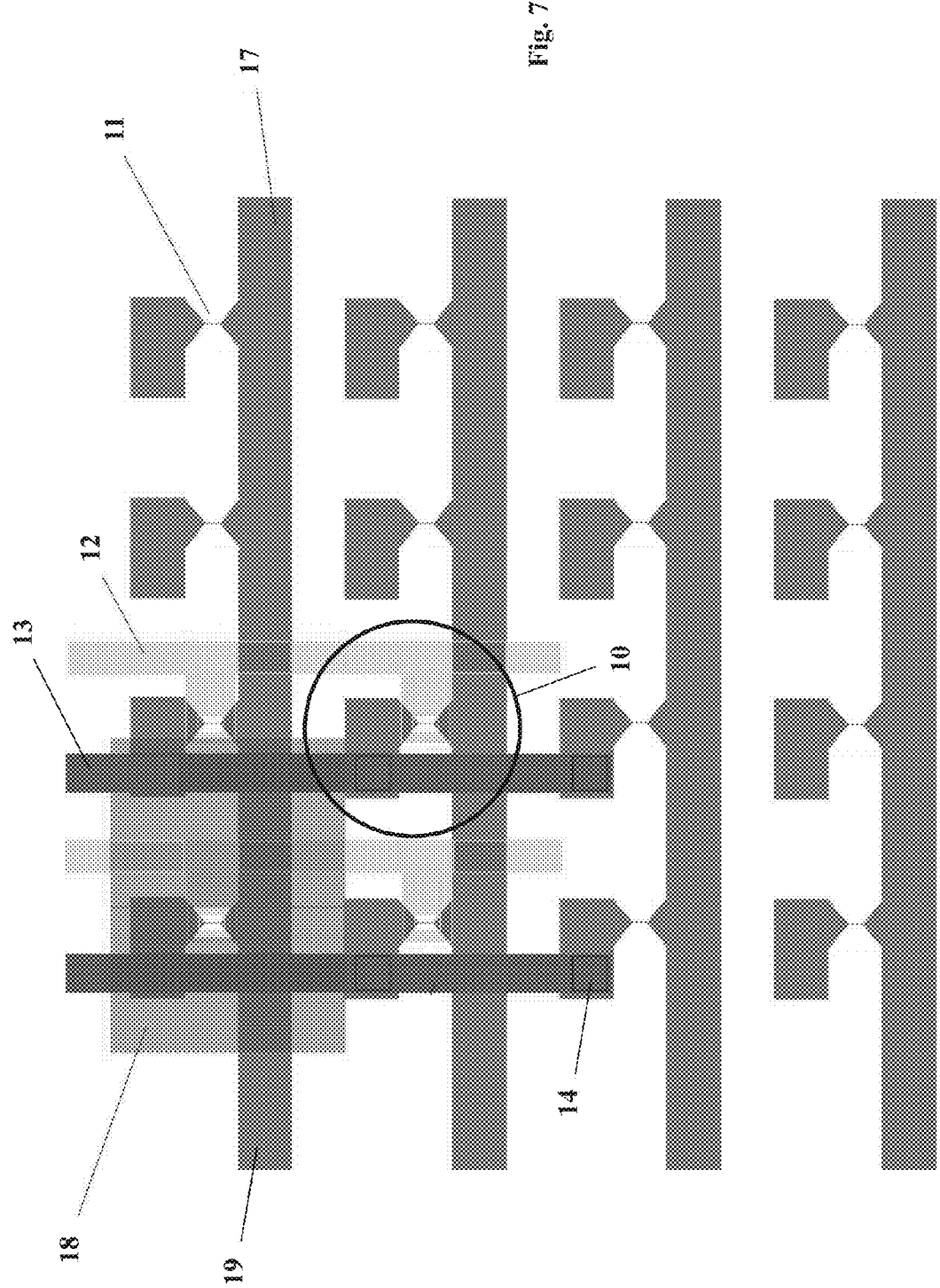
FIG. 7 schematically shows a mask design of the sensor chip including multiple pixels with contact lines of highly-doped silicon and having intrinsically-doped SiNWs.

The array is passivated with a passivation layer (18). However, for each pixel, there is an opening (16) leaving the gate area with the silicon nanowire (11) and part of the common metal electrode (12) exposed to the medium for sensing. The rest of the chip is passivated, as mentioned above. FIG. 7 shows a mask design (complete on the left top of the array) of the sensor chip including multiple pixels (10) grown on highly doped silicon (17) and having intrinsically doped silicon nanowires (11). One common metal electrode (12), such as gold, platinum or copper electrode, feeds the pixels with the high-frequency AC signal. There is a one common source lead (19) connecting the implanted sources of the pixels to the circuit. The drain contact (14) of each individual pixel is connected to the circuit via the drain leads (13). As mentioned above, each pixel is passivated with a passivation layer (18) only leaving the gate area open for sensing. As above, the reference electrode (not shown here) is placed outside of the chip.

The pixel array could be fabricated in a CMOS process with pre-processing and post-processing steps using a complete SOI CMOS process, where the top silicon layer is used as an active CMOS layer. In that case, the only post-processing is needed for the counter electrode, the reference electrode and the passivation layer. Alternatively, the pixel array can be fabricated using a standard CMOS process. In that case, the pre-processing is needed to define the silicon nanowire from an SOI wafer covering it by $Si_3N_4$ and then etching the rest of the surface down to the handle wafer. Then the handle wafer can be used in a standard CMOS process leaving the protected areas untouched. This is then followed by opening and contacting of the SiNW structures and post-processing for the counter electrode, the reference electrode and the passivation layer.

Figure 8:
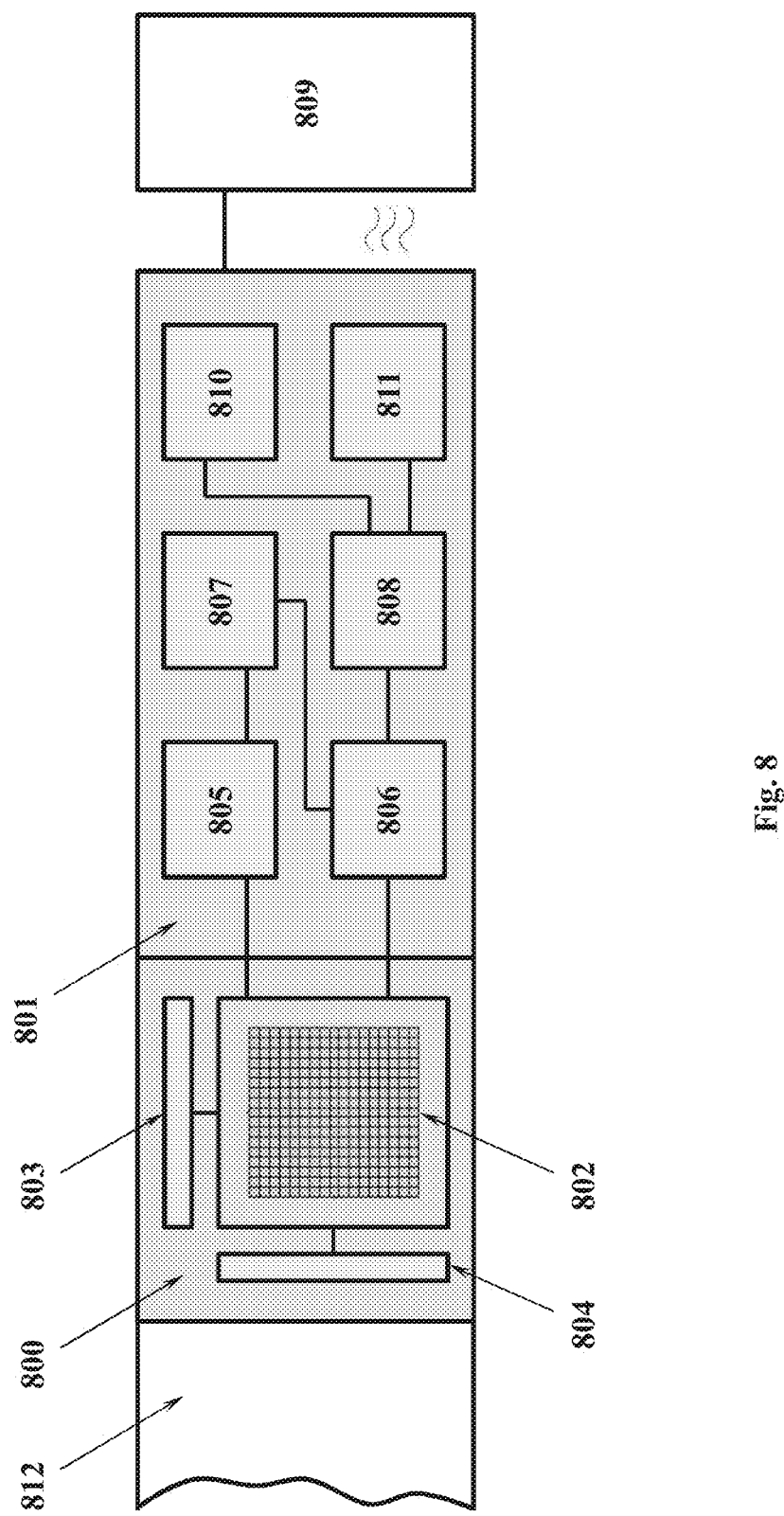
FIG. 8 schematically shows a microelectronic pixel-based sensor of an embodiment.

In another aspect of the present disclosure, FIG. 8 illustrates a nanoelectronic sensor comprising a disposable unit (800) mounted on a chip substrate and a reader unit (801) mounted on a flexible printed circuit board (PCB), wherein
1) the disposable unit (800) comprises:
   a pixel array (802) of an embodiment comprising a plurality of pixels arranged in rows and columns and exposed to medium for sensing,
   a row decoder (803) connected to said pixel array (802) for addressing a plurality of said pixels arranged in rows; and
   a column decoder (804) connected to said pixel array (802) for addressing a plurality of said pixels arranged in columns; and
2) the reader unit (801) comprises:
   a voltage source (805) connected to an electric circuit for supplying electric power to the sensor;

an integrated or CMOS current amplifier (806) connected to said pixel array (802) for amplification of an electric current obtained from the pixels;

an integrated waveform generator (807) for generating frequency of a sinusoidal electric stimulation;

an analogue-to-digital converter (808) with in-built digital input/output connected to said current amplifier (806) for outputting the converted signal to a user interface (809); and a connection module (810) for wired connection of the sensor to said user interface (809); or a wireless connection module (811) for wireless connection of the sensor to said user interface (809).

In a specific embodiment the wired connection module (810) is USB. In another specific embodiment, the wireless connection module (811) is NFC, Bluetooth®, Wi-Fi or GSM. The Bluetooth® or NFC technology provides the wireless communication between the sensor and the user interface (809) for up to 20 meters. In case of Wi-Fi, the connection between them can be established for up to 200 m, while the GSM module allows the worldwide communication.

In a particular embodiment, the sensor further comprises a microfluidic chip or lateral flow strip (812) for supplying an analyte solution to the pixels array. In general, a microfluidic chip is a set of micro-channels etched or molded into a material, such as glass, silicon or polymer. A non-limiting example of such polymer, which is used in many different microfluidic chips, includes polydimethylsiloxane (PDMS). The micro-channels forming the microfluidic chip are connected together in order to achieve the desired features, such as mixing, pumping, sorting and controlling the tested environment.

In a further embodiment, the voltage source (805) is a battery, such as AA-battery. However, the use of the battery is optional. Alternatively, the sensor can be powered, for example, either from the USB module or wirelessly via an RFID (Radio-Frequency Identification) tag.

Figure 9:
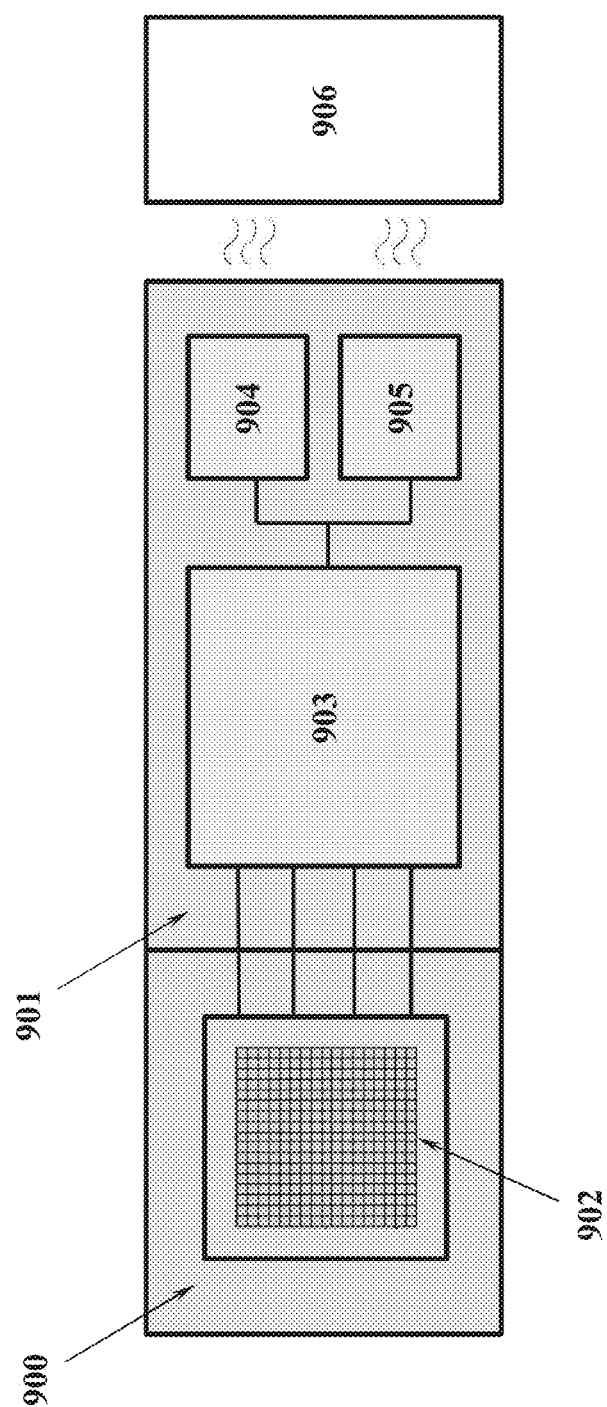
FIG. 9 schematically shows a wearable-patch pixel-based sensor of an embodiment.

In a further aspect of the present disclosure, FIG. 9 illustrates a wearable patch sensor comprising a disposable unit (900) printed on a chip substrate and a reader unit (901) printed on a flexible printed circuit board (PCB), wherein
i. the disposable unit (900) comprises a pixel array (902) of an embodiment comprising a plurality of pixels exposed to medium for sensing; and
ii. the reader unit (901) comprises:
an ASIC (Application-Specific Integrated Circuit) chip (903) customised for a particular use of the sensor;
a battery or power receiver (904) connected to an electric circuit for supplying electric current to the sensor; and
a wireless connection module (905) for wireless connection of the sensor to a user interface (906).

The ASIC chip (903) may include an amplifier for amplification of an electric current obtained from the pixels, an additional voltage source, such as a battery, for powering the sensor, a waveform function generator for generating frequency of a sinusoidal electric stimulation, and decoders.

In another aspect of the disclosure, the pixel's SiNW is functionalised with different molecules (herein, "receptors"), which are capable of binding to a target (analyte) molecule, for sensing. As a result, the sensor of an embodiment can be used for label-free detection of target (analyte) molecules by monitoring changes in the electric current of the transistor caused by variations in the charge density or the impedance at the gate oxide-electrolyte interface.

In general, charges formed in the liquid medium sensed by the ISFETs are originated from the dissolved molecules. Depending on the pH value of the liquid and the molecules' isoelectric point the dissolved molecules exhibit a global charge. However, this charge can be non-uniformly distributed over the molecule. In addition, the molecules have different size and a different 3D structure. Therefore it is very important that:
the sensor's interface is chemically engineered in a very uniform and reproducible manner,
receptors need to be immobilised on the sensor's surface as highly selective receptor layer with a very uniform grafting density,
the sensor should have redundant structure exhibiting multiple sensors cancelling out wrongly functionalised pixels, and
a molecular friendly surface architecture and microenvironment with fixed pH value, fixed ionic strength and temperature needs to be established to avoid denaturation of the molecules on the sensor surface.

The latter is controlled by respective reference sensors for temperature, pH value and ionic strength in the sensor chip design. However, even with the above-mentioned ideal sensor design it can be the case that the potentiometric detection of charges, which lead to changes in surface potential and hence, to a shift of the threshold voltage of ISFETs, cannot be detected, because the relevant charges are located outside of the Debye screening length of the liquid electrolyte.

In most cases, the molecular receptors bound to the transistor surface (the SiNW gate oxide in the present case) are separated from this surface by molecular cross-linkers or proteins of approximately 5-15 nm length. Therefore, the aforementioned charges are screened from the sensing surface by dissolved counter ions. As a result of the screening, the electrostatic potential that arises from charges on the analyte molecule exponentially decreases to zero with increasing the distance from the sensing surface. This screening distance is defined as a "Debye length", and it must be carefully selected when designing the ISFET's receptor layer in order to ensure the optimal sensing. For example, when detecting molecules in blood serum, the typical Debye screening length is 0.78 nm at 36° C. with an electrical permittivity of 74.5 for water. This means that after this length, the Debye screening length is given by:

$$\lambda_D = \sqrt{\frac{\epsilon_r \epsilon_0 k_b T}{2 n_0 z^2 e^2}}$$

where $n_0$ is the bulk concentration of the electrolyte, $\epsilon_r$ is the relative dielectric permittivity of the solvent (in case of water at 36° C. a value of 74.5), $\epsilon_0$ is the permittivity of the vacuum, $k_b$ is the Boltzmann constant, T is the temperature, z is the ion charge, and e is the elementary charge.

The screening length means that an electrical field originating from a point charge is dropped to its 1/e value (29%) in this length. Because of this limitation, charges from larger biomolecules (5-15 nm) cannot be detected in a serum sample. To overcome this problem, the charges should be attracted closer to the sensor surface by using very short length receptors or by operating the sensor in completely desalted buffers for electronic molecular detection.

Thus, the Debye length limitation can be overcome by modification of the receptors and controlling the immobilisation density over the ISFET's sensing surface. Elnathan et al 2012 described this approach in detail and demonstrated the increased sensitivity of their sensor to troponin detection directly from serum for the diagnosis of acute myocardial infarction. However, the present inventors made a step forward and proposed to sense beyond the Debye screening length without modification of the receptors, but operating the pixel-based sensor chip of some embodiments of the present application at high frequencies and using a combined transducer principle, which is one of the aspects of the present application. It will be described below in details. Only by combination of a precise monitoring and control of the main side parameters, temperature, pH and ionic strength with an array of electronically identical pixels of some embodiments of the present application, and a highly reproducible and uniform bioreceptor surface layer, the precise identification of biomolecules can be obtained.

Triple Readout

In a further aspect, the combined transducer principle defined herein as a "triple readout" includes: DC electronic readout of the sensor, AC electronic readout of the sensor and temperature sensing.

The pixel-based sensor of an embodiment is characterised with respect to its electronic properties and to the measurement configuration for molecular sensing applications. As noted above, similar to the SiNW ISFETs, the main features of the pixel-based sensor are determined by the transfer characteristics and the output characteristics at room temperature. The transfer characteristics shows the drain current ($I_{DS}$) of the SiNW as a function of the gate-source voltage at constant drain-source voltages. The output characteristics show $I_{DS}$ as a function of the drain-source voltage at constant gate voltages. The transfer characteristic was carried out by sweeping the gate voltage ($V_{FG}$ and/or $V_{BG}$) forward and backward in the range of applied voltage, while the $V_{DS}$ were kept constant. The output characteristic was measured by sweeping the $V_{DS}$ at a constant gate voltage ($V_{FG}$ and/or $V_{BG}$).

In general, a transfer function (TF) is a mathematical representation to describe inputs and outputs of black box models. In order to describe the frequency response of the pixel sensor, the pixel including a SiNW, a counter electrode and the first amplifier stage as a black box element with a certain frequency response. Since the analogue transistor amplification is exploited in an embodiment, the instant model is described with a term "transistor transfer function" (TTF). The TTF is defined as a mathematical ratio between the input ($V_{stim}$) and the output signal ($V_{out}$) of an electrical, frequency-dependent system. Its frequency response $H(j\omega)$ is defined as follows:

$$H(j\omega) = \frac{V_{out}(j\omega)}{V_{stim}(j\omega)},$$

wherein $\omega$ is the angular frequency and j is the imaginary unit. The TTF can be used to investigate impedance (defined as the ratio between voltage and applied current) or capacitance (defined as the capability of a capacitor to store charges) changes, caused by binding of biomolecules onto the transistor gate surface. This detection of analytes was reported in several publications even though the theory, on which the TTF relies, is still under discussion, because for each particular device and amplifier design, there are many parasitic side parameters that have a drastic effect on the TTF. A universal model is therefore difficult to establish. However, the authors of the present application have already demonstrated that it is possible, for example, to investigate the DNA hybridization, protein binding and to perform cell recordings by measuring this function.

In general, SiNWs are regarded and operated as long-channel ISFETs. Binding of molecules onto their gate surface leads to a capacitance and consequently, an impedance change of the solid-liquid interface of the device. For a better understanding of the TTF of the pixel-based sensor of an embodiment, its simplified equivalent circuit is shown in FIG. 10(a). This is a very crude approximation excluding all above-mentioned parasitic parameters of a reference electrode, electrolyte conductivity, transistor's feed lines, a gate oxide and amplifier characteristics. In the most simplistic approach, the transistor's gate impedance is represented by the capacitance $C_{Bio}$ and the resistance $R_{Bio}$, which are in parallel to each other and in series with the gate oxide capacitance. For a more complete modelling, the capacitance of the common source contact leads in parallel to the capacitance of the drain contact lead needs to be included. By binding of biomolecules to the gate structure only $C_{Bio}$ and the resistance $R_{Bio}$ are affected. Therefore, to describe the main response of the system, only the simplified circuit as shown in FIG. 10(b) is discussed herein.

As shown in FIG. 10(a), the receptor (or capture) molecules are immobilised onto the SiNW surface. They can be described as capacitance $C_{Bio}$ and resistance $R_{Bio}$. Due to binding of complementary target molecules to the capture molecules, the impedance of the system and, hence, the TTF are changed. The theoretical TTF, corresponding to the circuit of FIG. 10(b), is displayed on FIG. 10(c), wherein the left curve is for a bare SiNW surface (without capture or receptor molecules) and the right curve is for the SiNW surface with the immobilised receptor molecules. Two time constants $\tau_1$ and $\tau_2$ can be evaluated from the theoretical transfer function $H(j\omega)$:

$$\tau_1 = R_{Bio}(C_{Bio} + C_{Ox}) = \tau_2 + R_{Bio}C_{Ox}$$

$$\tau_2 = R_{Bio}C_{Bio}$$

wherein $\tau_2$ actually represents the relaxation time of the biomolecular layer.

The nature of the impedance change of the biomolecular layer is having many components. The size, isoelectric point and hence, the pH value of the test solution, the charge, distance, orientation, and packing density of the molecules are influencing this. In addition, the shape of the measured TTF curve depends on other (non-biological) parameters such as the reference electrode resistance $R_{RE}$, the solution resistance $R_{Sol}$, the capacitances of the contact leads and of the gate oxide $C_{Ox}$. The shift between these two curves is the so-called "cut-off frequency" or "band pass behaviour". From this frequency shift, the concentration of the molecules can be calibrated. It is well known, that the shift of the TTF and, therefore, the size of the cut-off frequency are more pronounced in lower concentrated electrolyte solutions. Therefore, the Debye screening of charges is also one component in the TTF approach, but not a dominating component like in the DC recording alone with the sensor of an embodiment.

The DC electronic readout is based on the transfer characteristics and is carried out in a liquid medium. The sensor in a DC readout mode is biased by a certain drain-source voltage while a voltage sweep is done through a reference electrode, and senses the charges at the functionalised sensor's surface. The resulting transfer characteristics reflects the characteristic behaviour of the sensor, as well as its surface condition, and is used to detect target molecules on a functionalised surface. The pixel's electric current changes when the target molecule binds to the sensor's surface and depends on the charge of the target molecules at the surface and consequently on their concentration. Negatively charged molecules leads to a shift of the transfer characteristics to the right and positively charged molecules cause a shift to the left.

Figure 11:
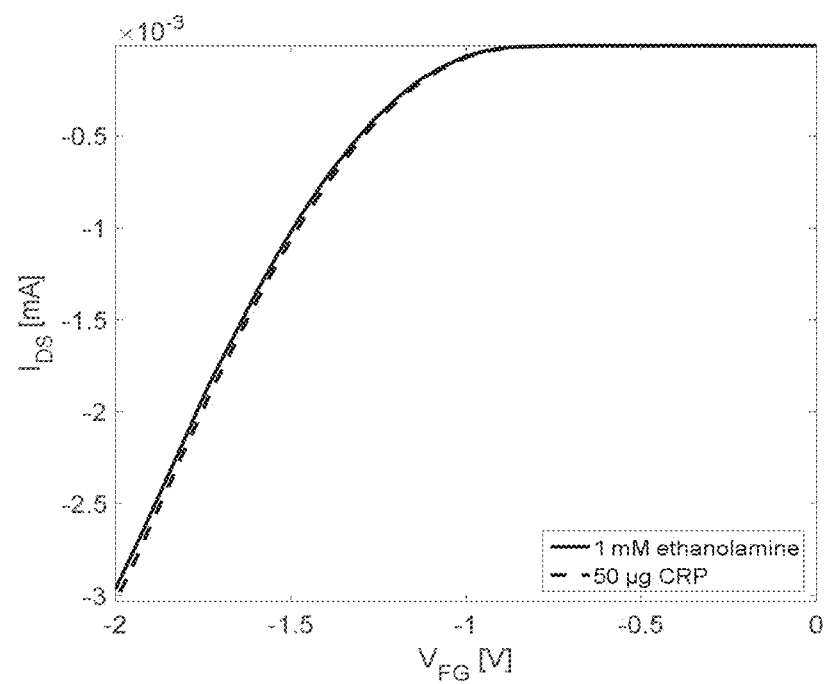
FIG. 11(a) shows the transfer characteristics of the sensor functionalised with receptors in 1 mM ethanolamine (solid line) and the same sensor in the presence of 50 µg CRP (C-reactive protein), which is a target molecule (dotted line).
FIGS. 11(b)-(c) shows the measurement of the shift at the largest slope point corresponding to the highest $g_m$ value.
Figure 11:
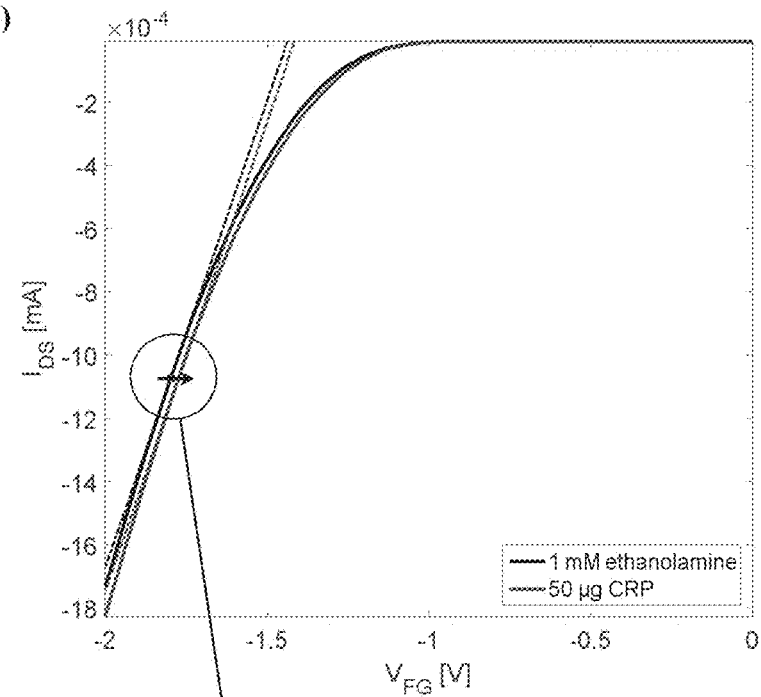
Figure 11:
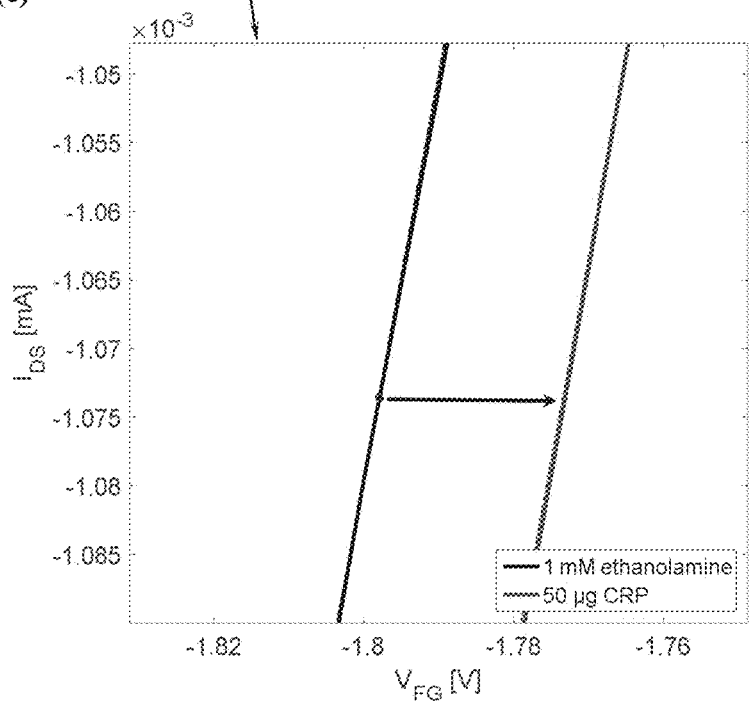

Reference is now made to FIG. 11(a) showing the transfer characteristics of the sensor functionalised with receptors in 1 mM ethanolamine (solid line) and the same sensor in the presence of 50 μg CRP (C-reactive protein), which is a target molecule (dotted line). FIG. 11(b) shows the measurement of the shift at the largest slope point corresponding to the highest transconductance $g_m$ value. The shift at this point is clearly visible in the zoomed-in FIG. 11(c). This particular point on the curve with the largest slope value also corresponds to the maximum sensitivity of the sensor. It is calculated from the maximum of the first derivative $\Delta I_{DS}/\Delta V_{GS}$ of the recorded transfer characteristics without the target molecule. From that value, the voltage shift to the detection curve is calculated. The voltage shift value is very characteristic to a particular target molecule and depends on its concentration.

The above DC readout allows building a correlation plot for different sensor biasing measurements, i.e. measuring the DC characteristics at different drain-source voltages. This plot actually visualises the potential changes on the sensor's surface. Data extracted from this plot can be used as an additional parameter for the multivariable detection analysis of the target molecule.

Figure 12:
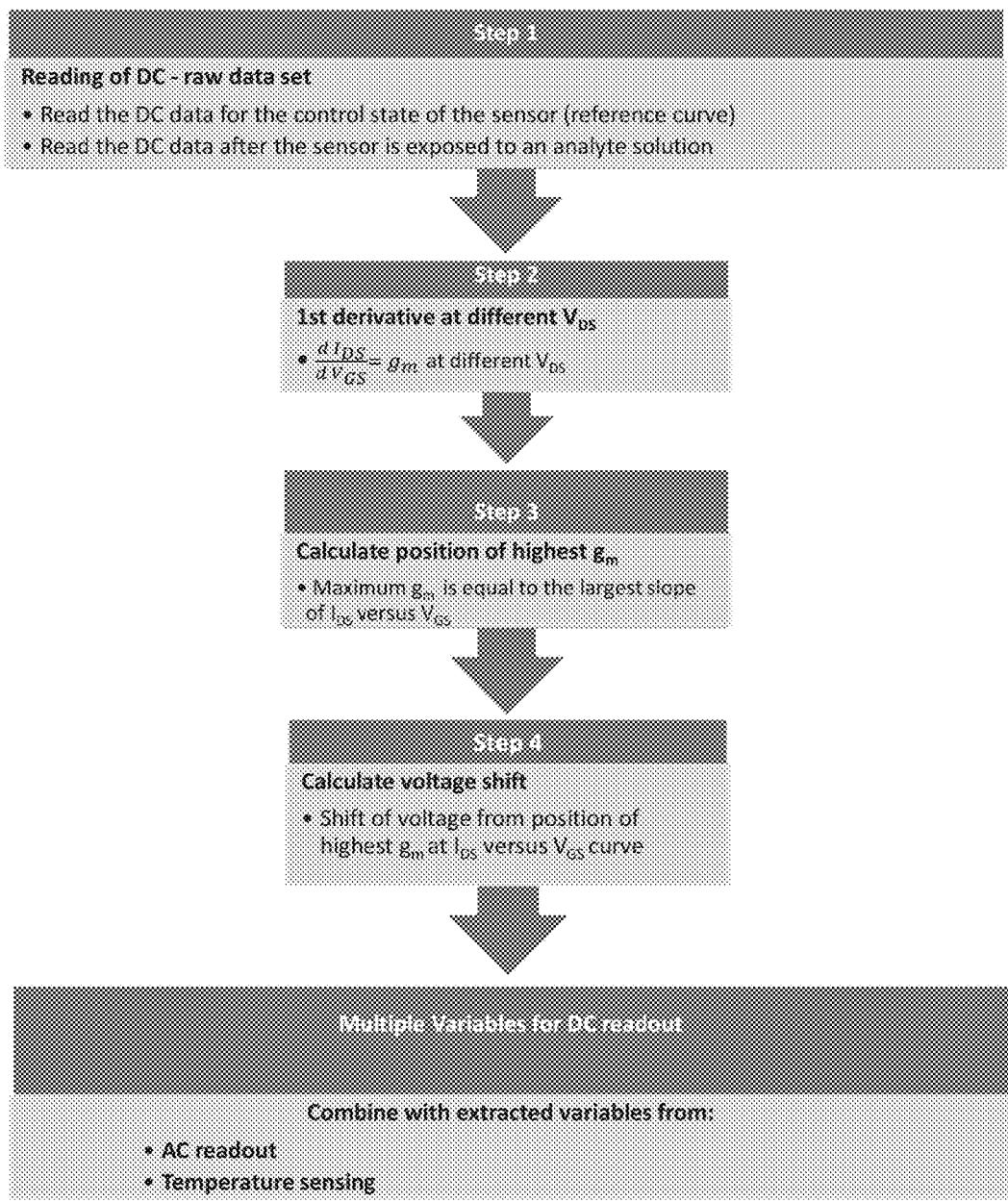
FIG. 12 shows a flow chart for the DC readout method from a sensor of an embodiment.
Figure 13:
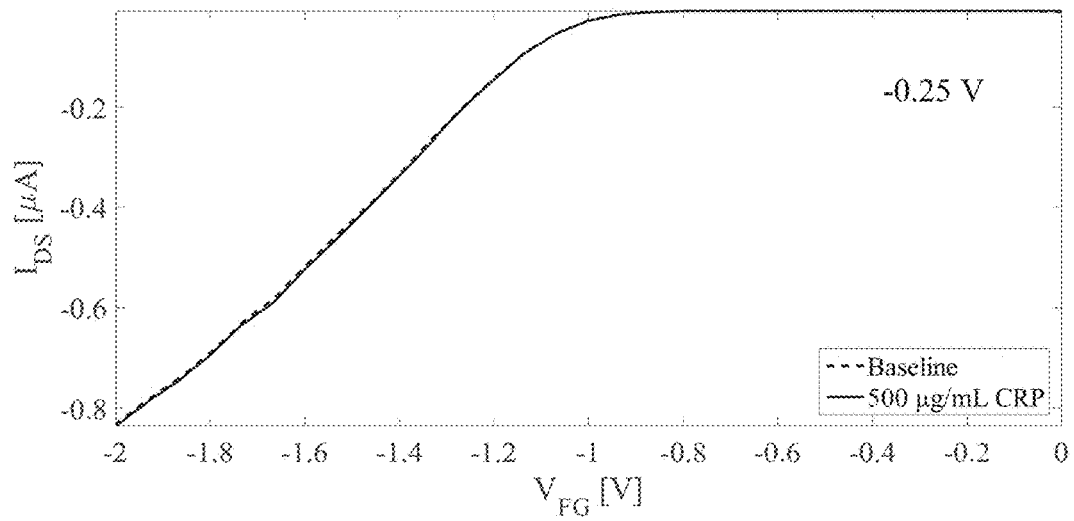
FIGS. 13(a)-(d) show the plots of $I_{DS}$ vs $V_{GS}$ for one channel at $V_{DS}$=0.25 V, 0.5 V, 0.75 V and 1 V, respectively, for the control sensor (baseline) and the sensor exposed to the analyte solution containing 500 µg/mL CRP (C-reactive protein).
Figure 13:
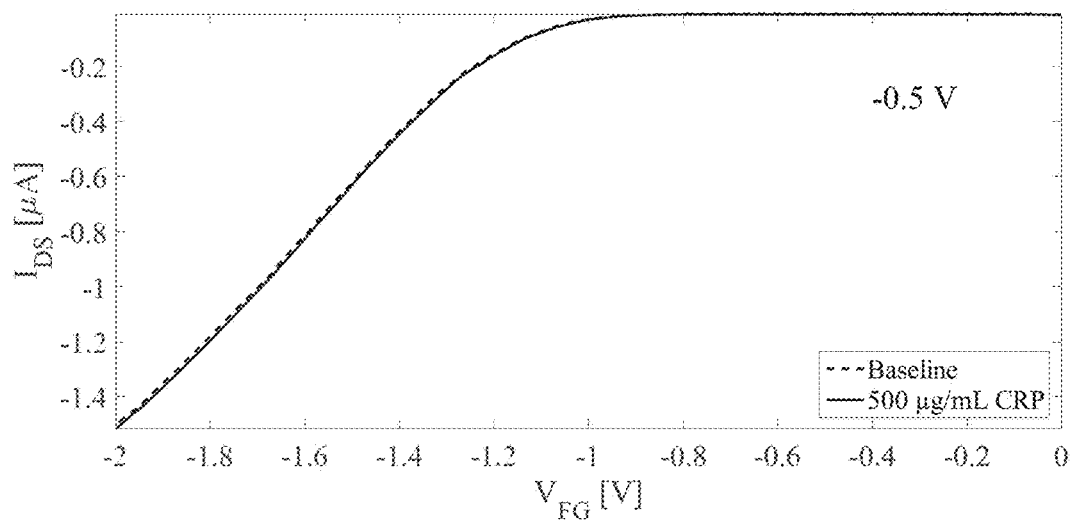
Figure 13:
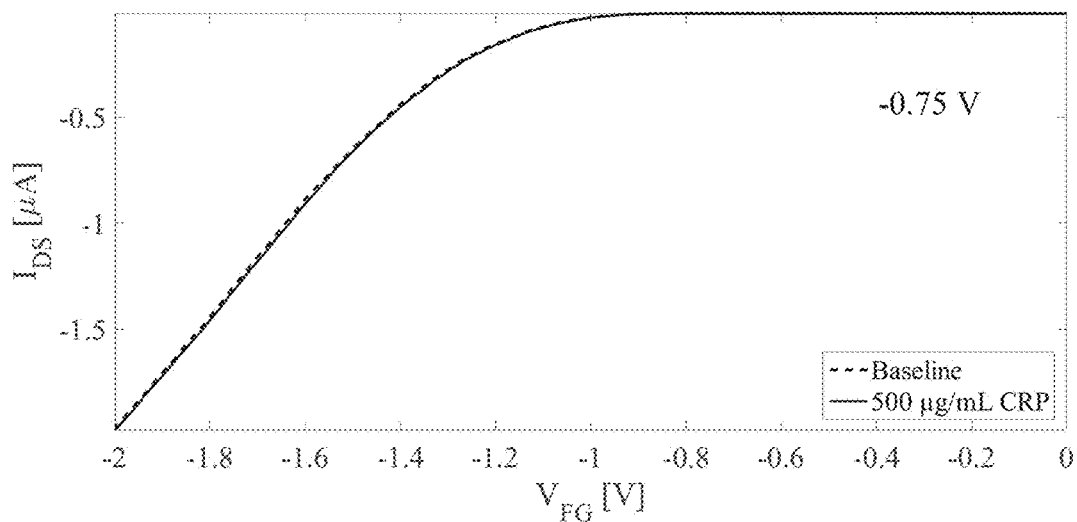
Figure 13:
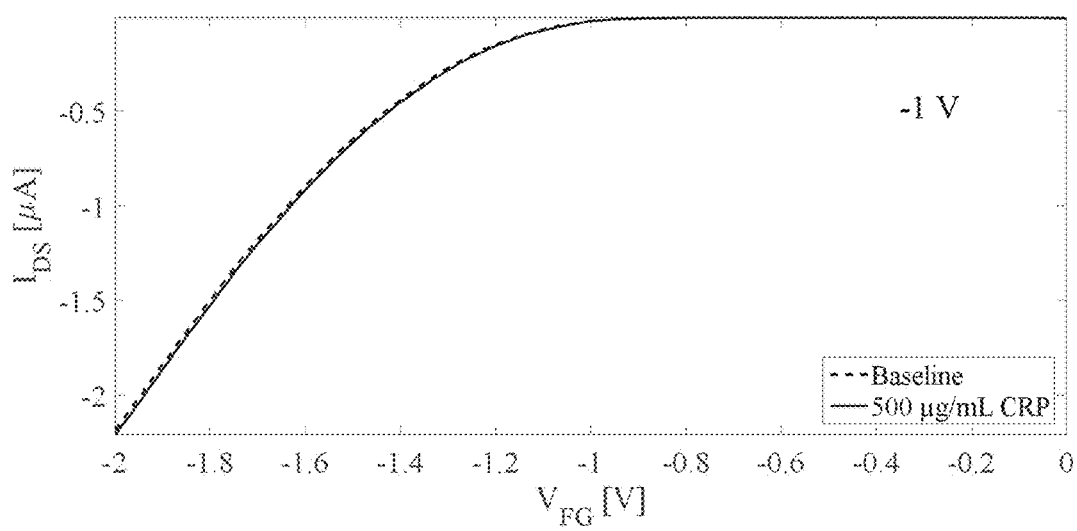

In an embodiment, a method for performing a DC readout with a sensor of an embodiment comprises the following steps, as shown in FIG. 12:
1) i) Reading the raw data of a drain-source current ($I_{DS}$) and a gate-source voltage ($V_{GS}$) from a control sensor (before addition of an analyte solution) and from the sensor exposed to an analyte solution, while a drain-source voltage ($V_{DS}$) is kept constant;
   ii) Sweeping the $V_{DS}$ voltage with a reference electrode of the sensor and repeating the previous step for different $V_{DS}$ voltages to generate the sets of $I_{DS}$-$V_{GS}$ raw data and to plot the corresponding $I_{DS}$ vs $V_{GS}$ curves;
2) Calculating a transconductance ($g_m$) by taking a first derivative of said $I_{DS}$-$V_{GS}$ curves at said different $V_{DS}$ voltages and plotting the calculated $g_m$ vs $V_{GS}$ curves for said $V_{DS}$ voltages;
3) Finding the maximum transconductance point $g_m$ (max) (the peak) in said $g_m$-$V_{GS}$ curves and extracting the $V_{GS}$ voltage corresponding to the $g_m$ (max) in these curves; and
4) Choosing the point on the $I_{DS}$-$V_{GS}$ curves generated in Step 1, said point corresponding to the $V_{GS}$ voltage obtained in Step 3, and taking a difference between this $V_G$ voltage of the control sensor and the sensor exposed to the analyte solution, thereby calculating a voltage shift ($\Delta V$).

In Step 1, the raw data of a drain-source current ($I_{DS}$) and a gate-source voltage ($V_{GS}$) is read from a control sensor (before addition of an analyte solution), while a drain-source voltage ($V_{DS}$) is kept constant. The sweep of $V_{DS}$ is done in steps through a reference electrode, and the $I_{DS}$-$V_{GS}$ set of raw data is collected for each $V_{DS}$. Then the sets of the $I_{DS}$-$V_{GS}$ raw data at the same stepped $V_{DS}$ are recorded of the sensor exposed to the analyte solution, and the graphs of $I_{DS}$ vs $V_{GS}$ at different $V_{DS}$ are plotted for both states of the sensor (before and after addition of the analyte solution).

FIGS. 13(a)-(d) show the plots of $I_{DS}$ vs $V_{GS}$ for one channel at $V_{DS}$=−0.25 V, −0.5 V, −0.75 V and −1 V, respectively, for the control sensor (baseline) and the sensor exposed to the analyte solution containing 500 μg/mL CRP (C-reactive protein).

In Step 2, the transconductance $g_m$ is calculated as a first derivative of the $I_{DS}$-$V_{GS}$ curves at different $V_{DS}$:

$$g_m = \frac{\partial I_{DS}}{\partial V_{GS}}$$

Figure 14:
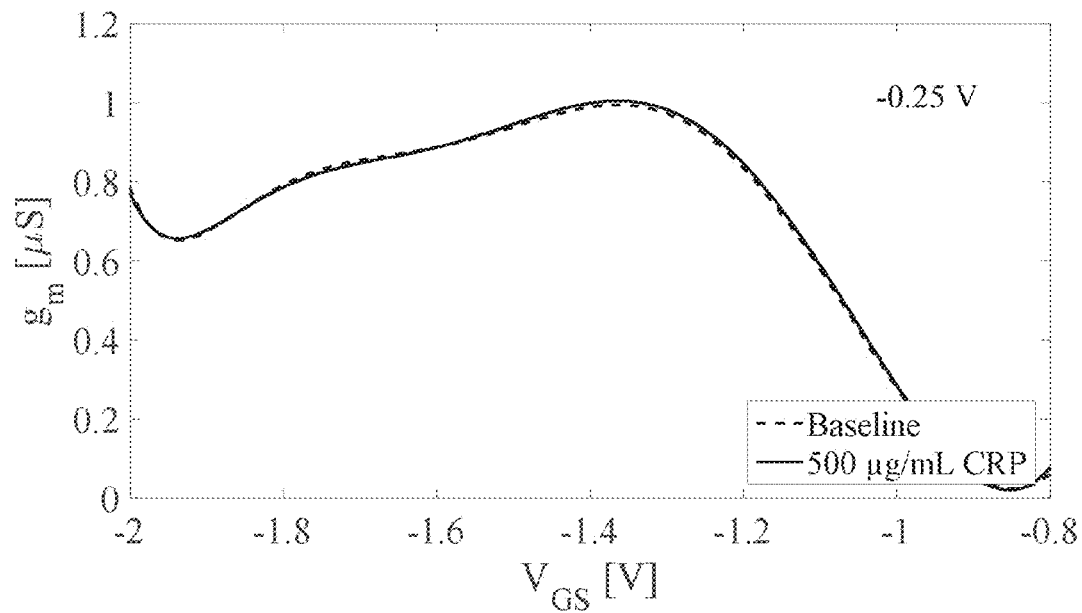
FIGS. 14(a)-(b) show the plots of the calculated $g_m$ vs $V_{GS}$ for two $V_{DS}$=−0.25 V and −1 V, respectively.
Figure 14:
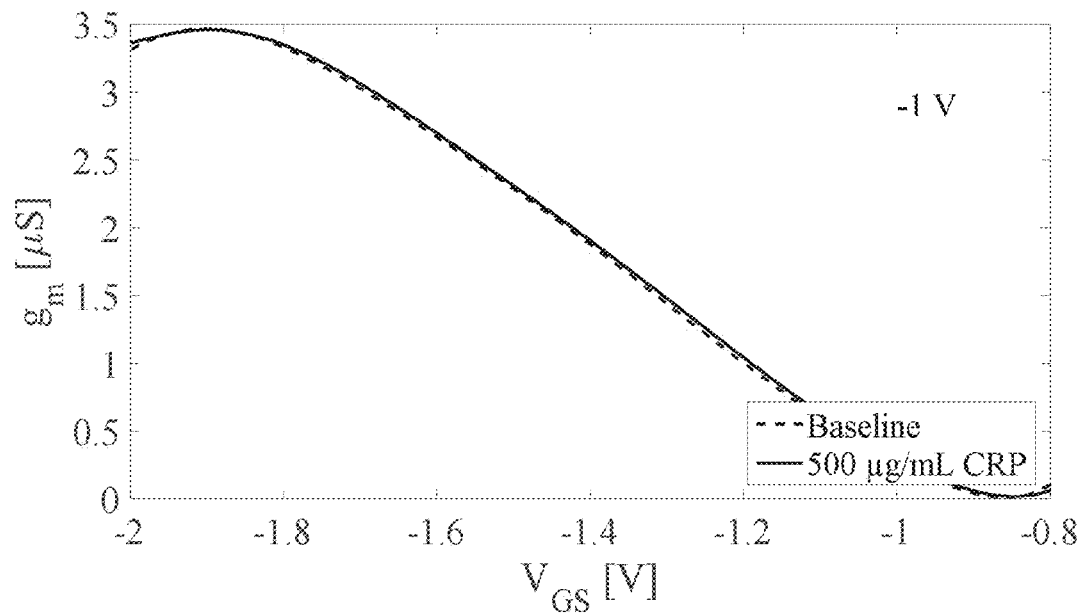
Figure 15:
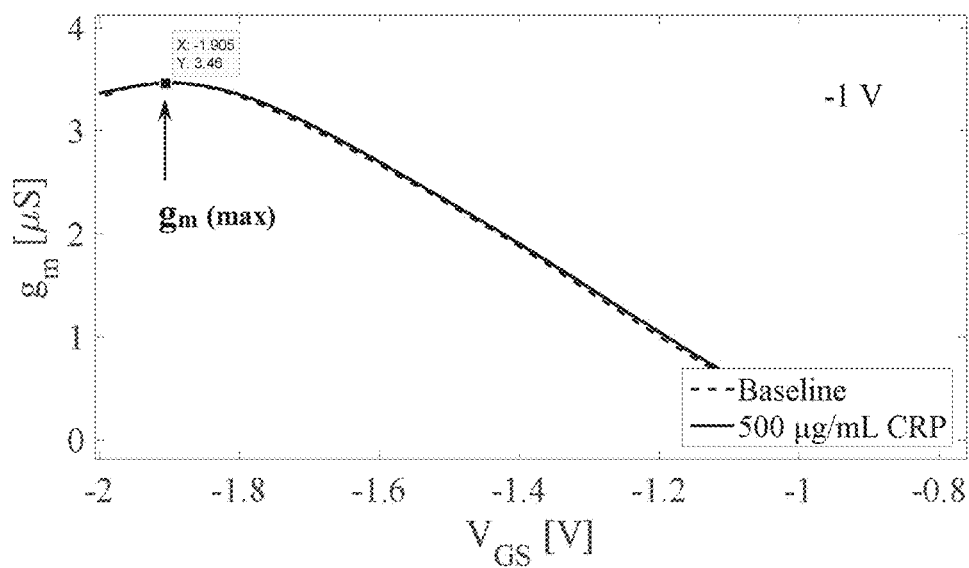
FIG. 15 shows the plot of $g_m$ vs $V_{GS}$ with the peak corresponding to the $g_m$ (max) value.

FIGS. 14(a)-(b) show the plots of the calculated $g_m$ vs $V_{GS}$ for two $V_{DS}$=−0.25 V and −1 V, respectively. Step 3 deals with finding the highest transconductance value $g_m$ (max), which is equal to the largest slope in the $I_{DS}$ vs $V_{GS}$ curve for the particular $V_{DS}$. The $g_m$ (max) value corresponds to the highest sensitivity of the sensor. FIG. 15 shows the plot of $g_m$ vs $V_{GS}$ with the peak corresponding to the $g_m$ (max) value. The $V_{GS}$ at this point, found to be −1.905 V, will be used in the next step to get the voltage shift between the control sensor (baseline) and the sensor exposed to the analyte solution.

Figure 16:
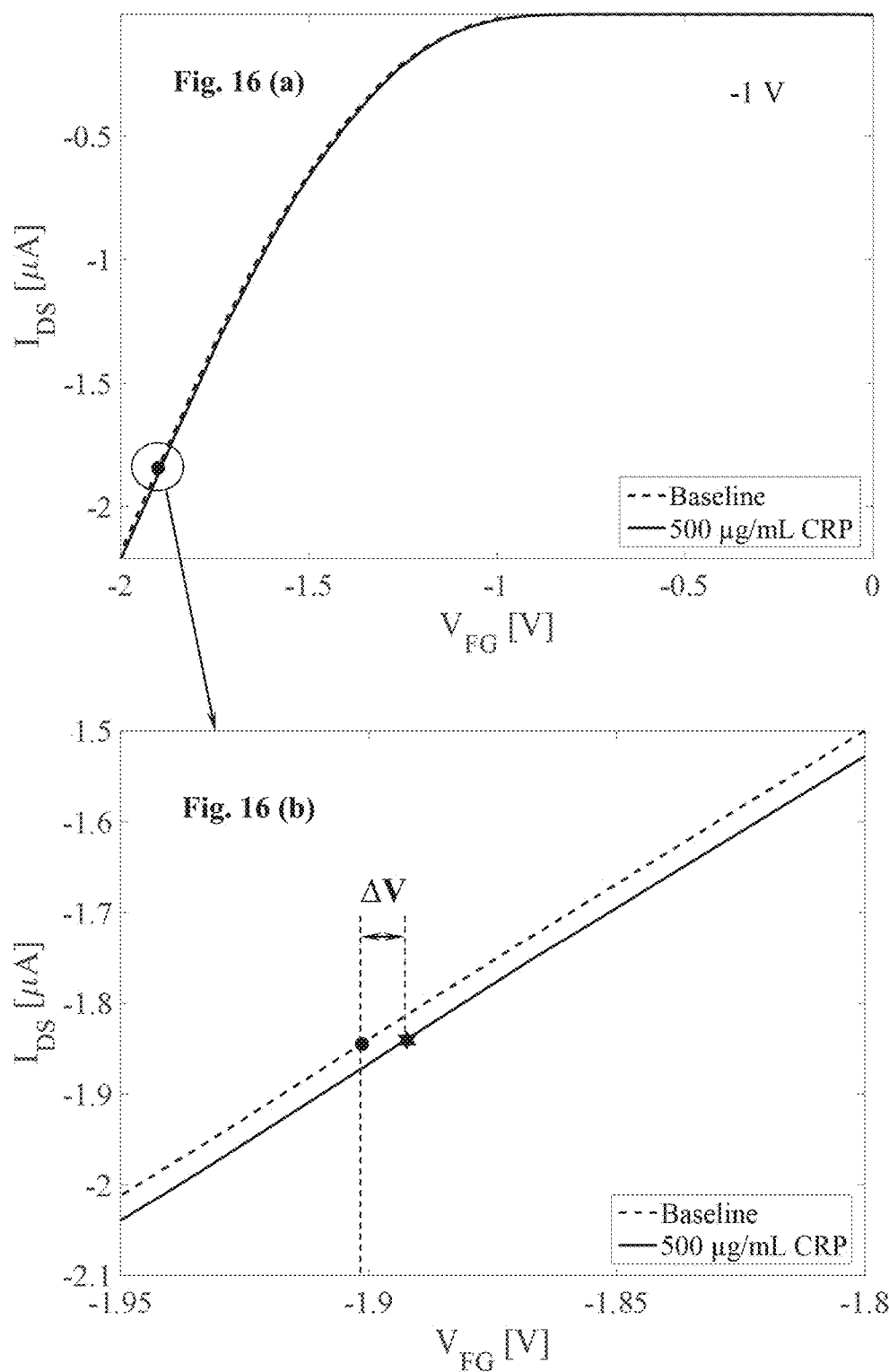
FIG. 16(a) shows the original plot of $I_{DS}$ vs $V_{GS}$ for one channel at $V_{DS}$=−1 V for the control sensor (baseline) and the sensor exposed to the analyte solution containing 500 µg/mL CRP.
FIG. 16(b) shows the zoomed-in area of the $I_{DS}$-$V_{GS}$ plot of FIG. 16(a) corresponding to the highest sensitivity of the sensor.

In Step 4, the algorithm returns to the initially recorded plot of $I_{DS}$ vs $V_{GS}$ for the specific $V_{DS}$ and choose the point on the curve for the $V_{GS}$=−1.905 V found in the previous step, which corresponds to $g_m$ (max) and the highest sensitivity of the sensor. Voltage shift between the control sensor (baseline) and the sensor exposed to the analyte solution is then calculated at this point, which is also a point of the highest slope in the $I_{DS}$-$V_{GS}$ curve. FIG. 16(a) shows the original plot of $I_{DS}$ vs $V_{GS}$ for one channel at $V_{DS}$=−1 V for the control sensor (baseline) and the sensor exposed to the analyte solution containing 500 μg/mL CRP, while FIG. 16(b) zooms in the area of the highest sensitivity of the sensor to demonstrate the voltage shift $\Delta V$.

The DC electronic readout is most sensitive to pH changes and useful for enzymatic tests, electrochemical sensing and affinity-based sensing when charged molecules are involved. This is because the SiNW has an oxide surface, which can be protonated or deprotonated leading to the typical pH sensitivity. As explained in the background section, depending on the point of zero charge of the surface, which is actually the solution pH value at which the surface is neutral, the sensor exhibits a certain surface potential. The gate $SiO_2$ of the SiNW FETs, for example, is covered by a layer of amphoteric hydroxyl groups (Si—OH) in solution and it has the point of zero charge at about 2.2, while $Si_3N_4$ has this point at about 6.5. These —OH groups can be protonated or deprotonated in solution depending on the pH value of the solution. When pH of the liquid medium (electrolyte) is higher than the point of zero charge of the gate material, the SiNW gate dielectric will be deprotonated (or negatively charged) and vice versa. This charge at the surface will in turn shift the threshold voltage of the SiNW and change the drain-source current.

As noted above, the main limitation in the DC readout mode is the Debye screening of charges. Also, the DC readout is not suitable for all kind of the functionalised surfaces and mainly depends on the charge carried by the target molecule. These limitations can be overcome by adding the AC readout using a frequency sweep up to 1 MHz or higher. Opposite to the DC readout, the charges of the target molecules have a negligible influence on the sensing in the AC mode. In addition, the AC readout can detect the presence of the bound molecules. The AC sensing mode has the same basis as the impedance spectroscopy. It shows the change of the sensor's surface capacitance and resistance which contains information about the binding of the target molecule, as well as the 'number' (concentration) of the bound molecules.

Furthermore, the AC readout provides information about capacitance and resistance of the analyte solution, such as buffer, serum or blood, homogeneity of the surface functionalised with receptors and information about the number of the bound molecules. This information allows a quality control and building a calibration curve for detection of the target molecule and its quantification.

Figure 17:
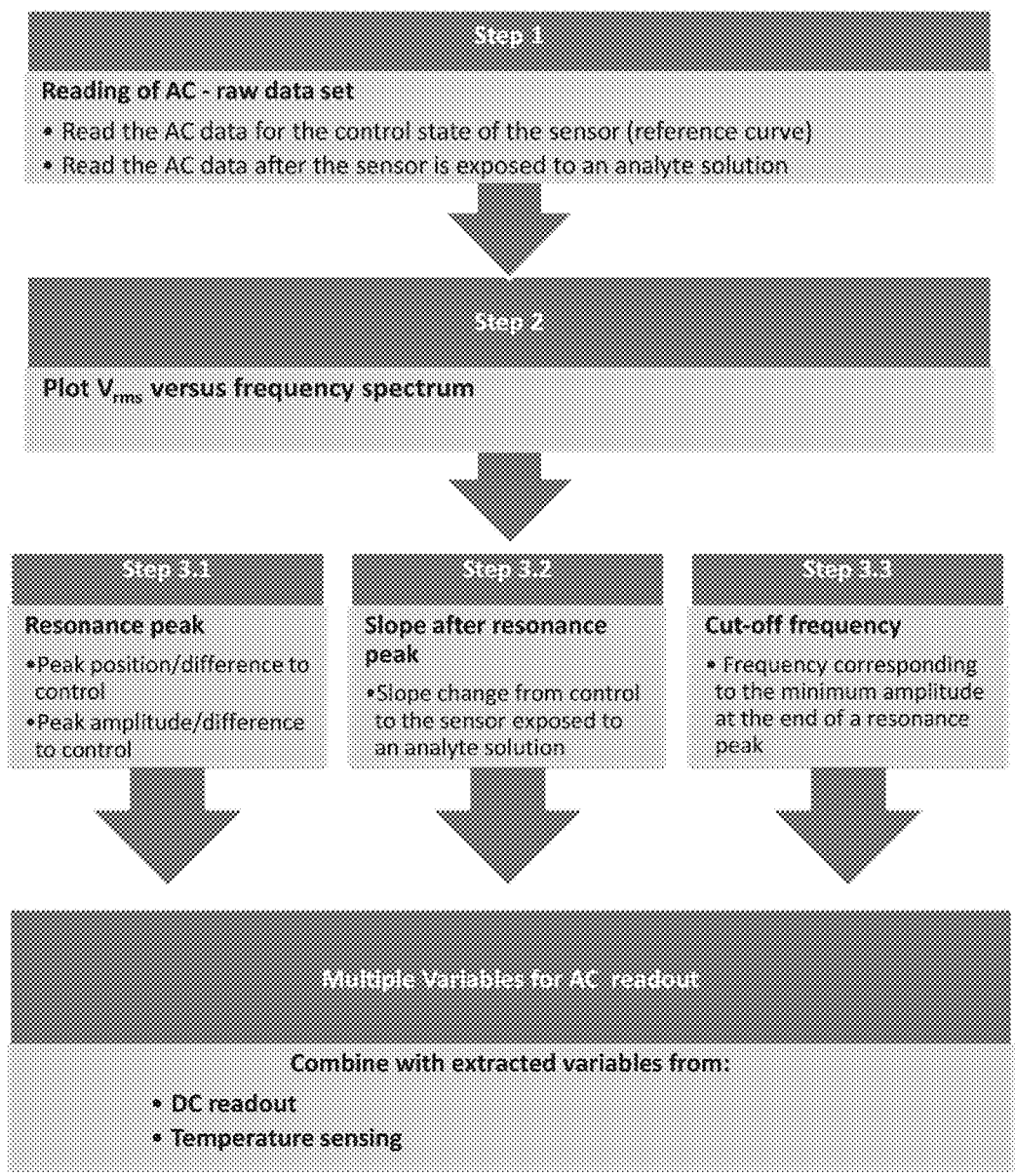
FIG. 17 shows a flow chart for the AC readout method from a sensor of an embodiment.

In an embodiment, a method for performing an AC readout with a sensor of an embodiment comprises the following steps, as shown in FIG. 17:
1) Reading the raw data of a root-mean-square voltage (Vrms) from a lock-in amplifier of a control sensor (before addition of an analyte solution) and the sensor exposed to an analyte solution;
2) Plotting said Vrms data vs a current frequency (w);
3) Calculating the amplitude and frequency difference between the control sensor and the sensor exposed to an analyte solution for a resonance peak in the Vrms-$\omega$ plot obtained in Step 2;
4) Calculating the cut-off slope of the Vrms-$\omega$ plot obtained in Step 2;
5) Calculating the cut-off frequency corresponding to the frequency at the lowest amplitude of the resonance peak by:
i) Processing the first polynomial fit to said cut-off slope obtained in Step 4;
ii) Finding an x-intercept, which is equal to the cut-off frequency, of the fitted curves for the control sensor and for the sensor exposed to the analyte solution; and
6) Taking a difference between the calculated cut-off frequencies of the control sensor and the sensor exposed to the analyte solution, thereby calculating a cut-off frequency shift.

In Step 1, the raw data is read from a lock-in amplifier, which can extract a very small signal with a known carrier wave in the presence of overwhelming noise. Lock-in amplifiers are actually used to detect and measure very small AC signals—all the way down to a few nanovolts. Accurate measurements may be made even when the small signal is obscured by noise sources many thousands of times larger. Lock-in amplifiers use a technique known as phase-sensitive detection to cancel out the component of the signal at a specific reference frequency and phase. Noise signals, at frequencies other than the reference frequency, are rejected and do not affect the measurement. Non-limiting examples of lock-in amplifiers are instruments SR810 and SR830 by SRS®, which are 100 kHz lock-in amplifiers.

Lock-in amplifiers, as a general rule, display the input signal in "Volts rms" (root mean square). This is because the average value of an AC waveform is not the same value as that for a DC waveforms average value, since the AC waveform is constantly changing with time. The equivalent average value for an alternating current system that provides the same power to the load as a DC equivalent circuit is called the "effective value".

There are many ways of explaining rms voltage at different levels of complexity. For the simplest level, say that one can measure the current (or potential difference) at tiny intervals of time, then square each value, add up the squares (which are all positive) and divide by the number of samples to find the average square or mean square. Taking the square root of the obtained value will result in the rms value. In fact, the rms values are the DC equivalent values that provide the same power to the load in the AC mode. Thus, when a lock-in amplifier displays a magnitude of 1 V (rms), the component of the input signal (at the reference frequency) is a sine wave with amplitude of 1 Vrms, or 2.8 Vpp.

In Step 2, Vrms is plotted against frequency spectrum, followed by Step 3.1, in which the resonance peak information is extracted from the plot. The following two parameters, which are extracted from the plot, characterise the resonance peak:
1) Amplitude of the resonance peak, which depends on a sensor's surface charge and number of bound target molecules (target molecule concentration); and
2) Width of the resonance peak, which depends on surface charge and number of bound target molecules (target molecule concentration).

Figure 18:
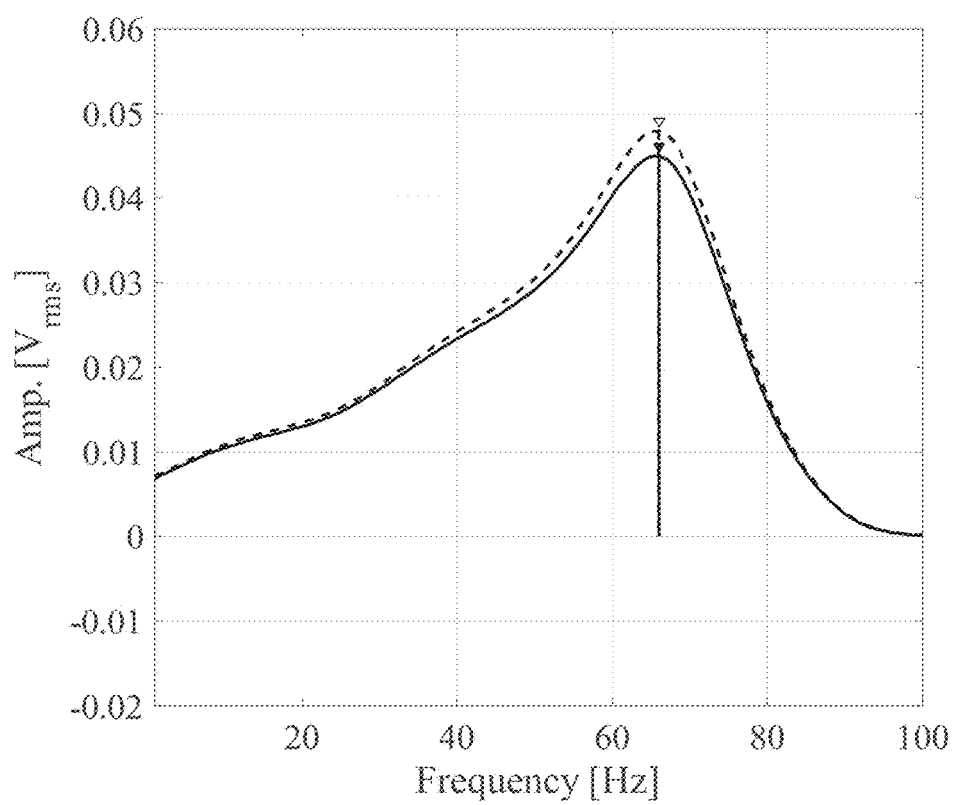
FIG. 18 illustrates the peak finding algorithm for the AC readout mode.
Figure 19:
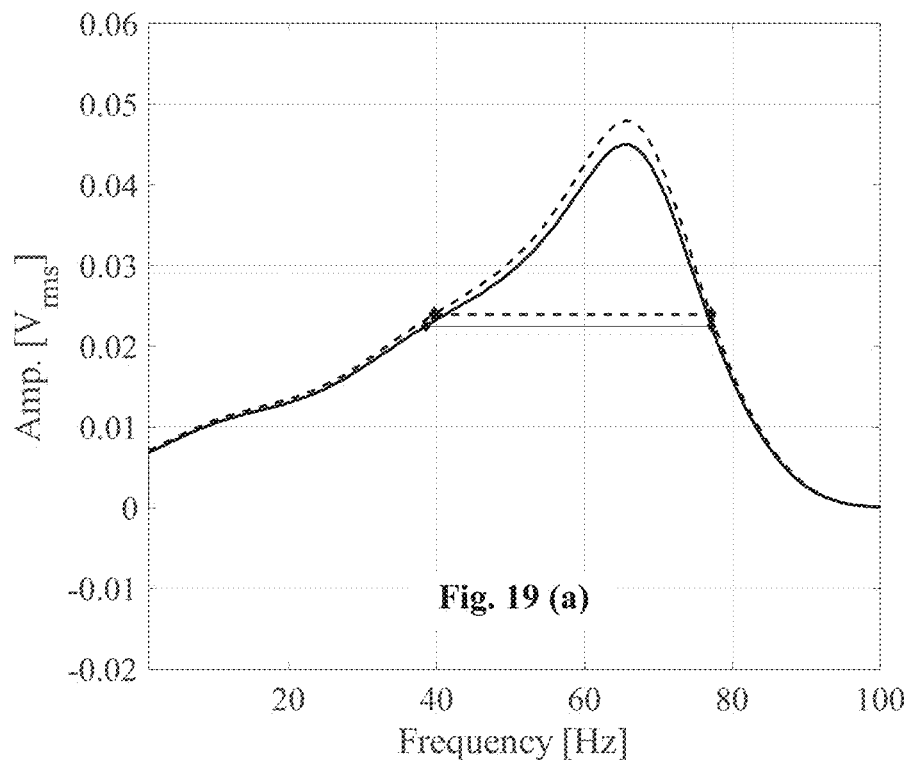
FIGS. 19(a)-(b) demonstrate the calculation of the peak width in the AC readout mode.
Figure 19:
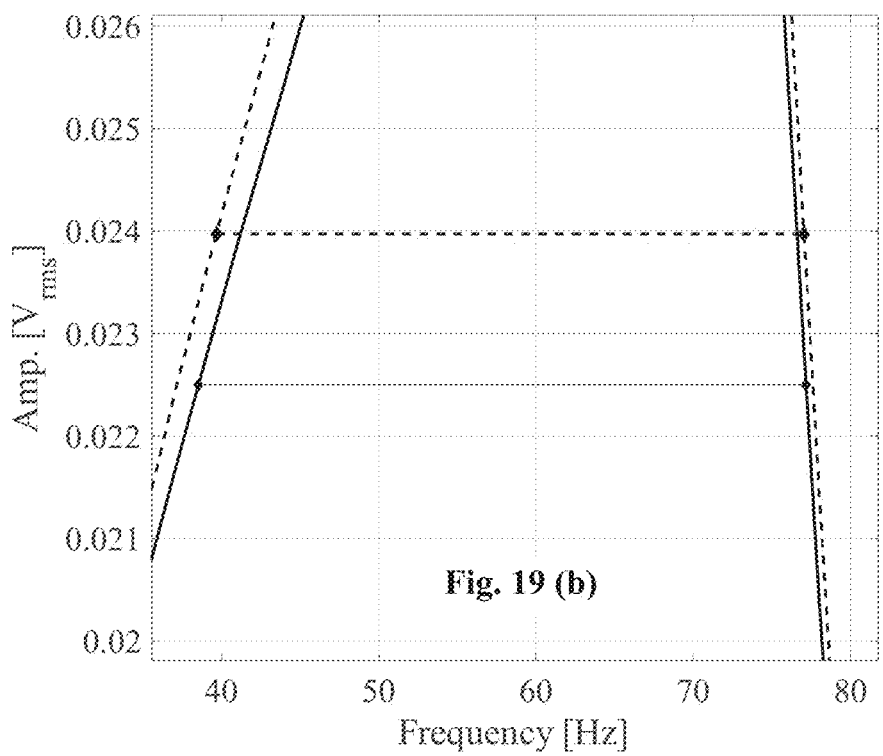

FIG. 18 illustrates the peak finding algorithm, which comprises the steps of calculating the difference of amplitude to baseline (extracting peak amplitude) and calculating the difference of peak position to baseline (extracting peak frequency). FIG. 19($a$) demonstrates the calculation of the peak width, while FIG. 19($b$) zoom-in to the area of the peak width at half of the maximum amplitude. Thus, according to the peak amplitude, the peak width is calculated at half of the maximum amplitude with difference to baseline.

Figure 20:
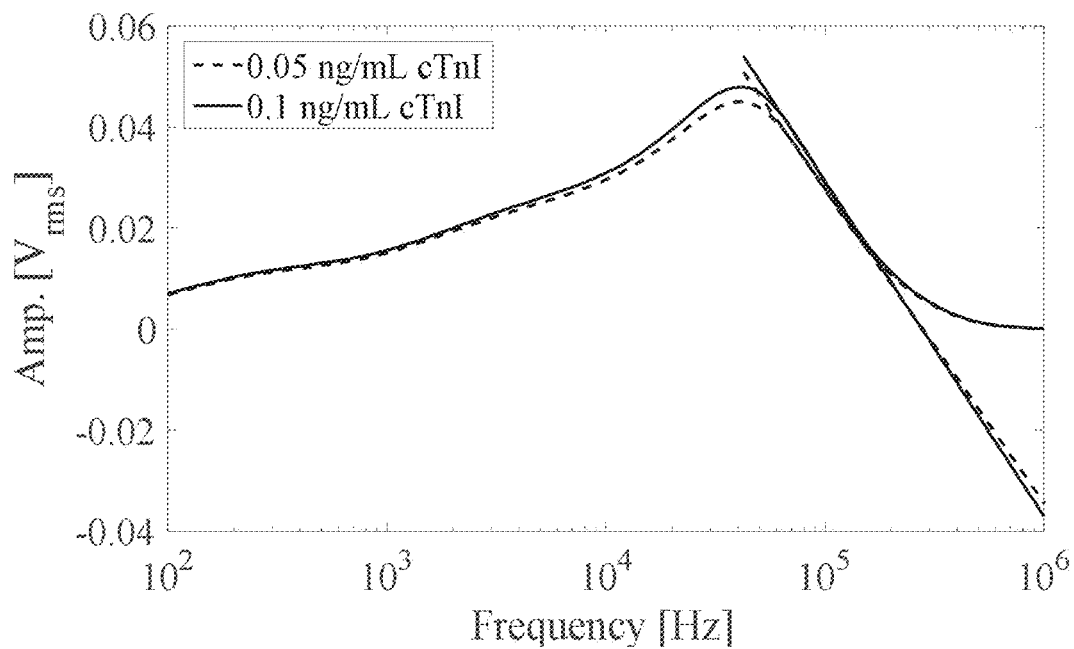
FIGS. 20(a)-(b) demonstrate the calculation of the cut-off slope in the AC readout mode.
Figure 20:
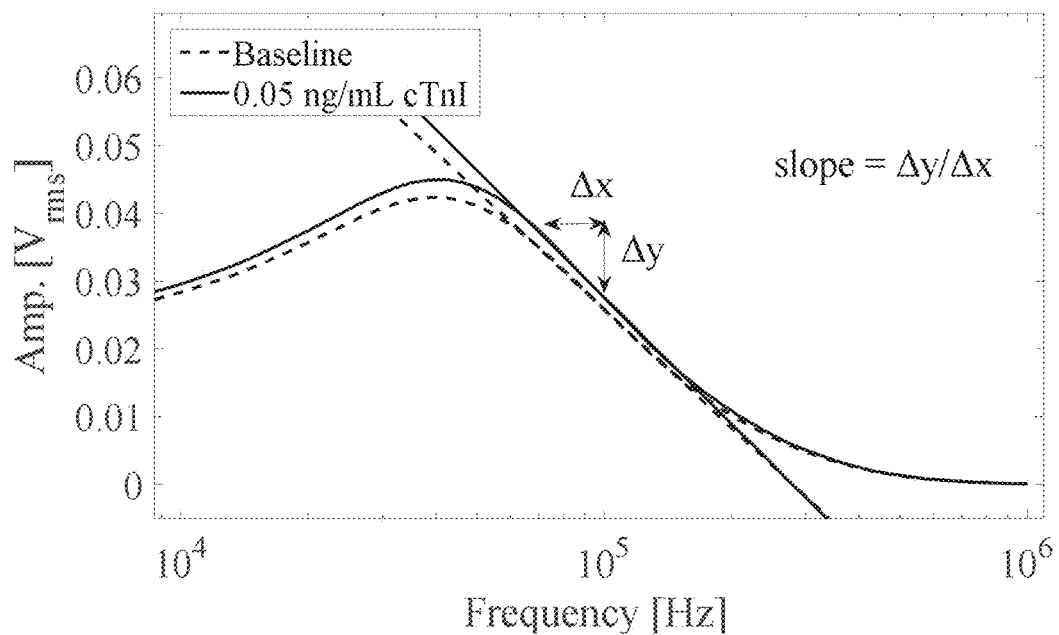
Figure 21:
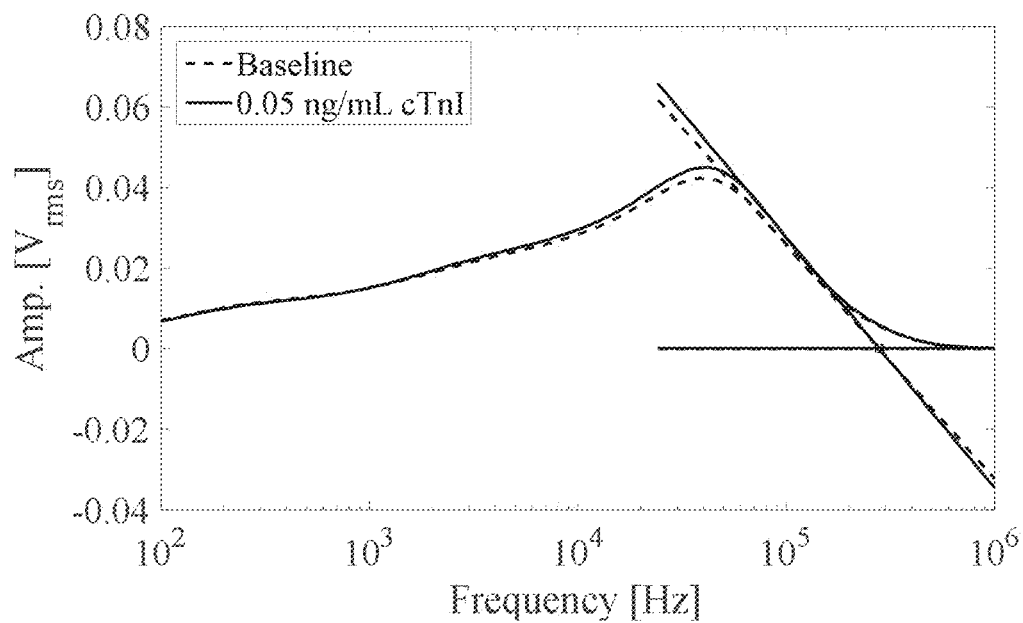
FIGS. 21(a)-(b) demonstrate the calculation of the cut-off frequency in the AC readout mode.
Figure 21:
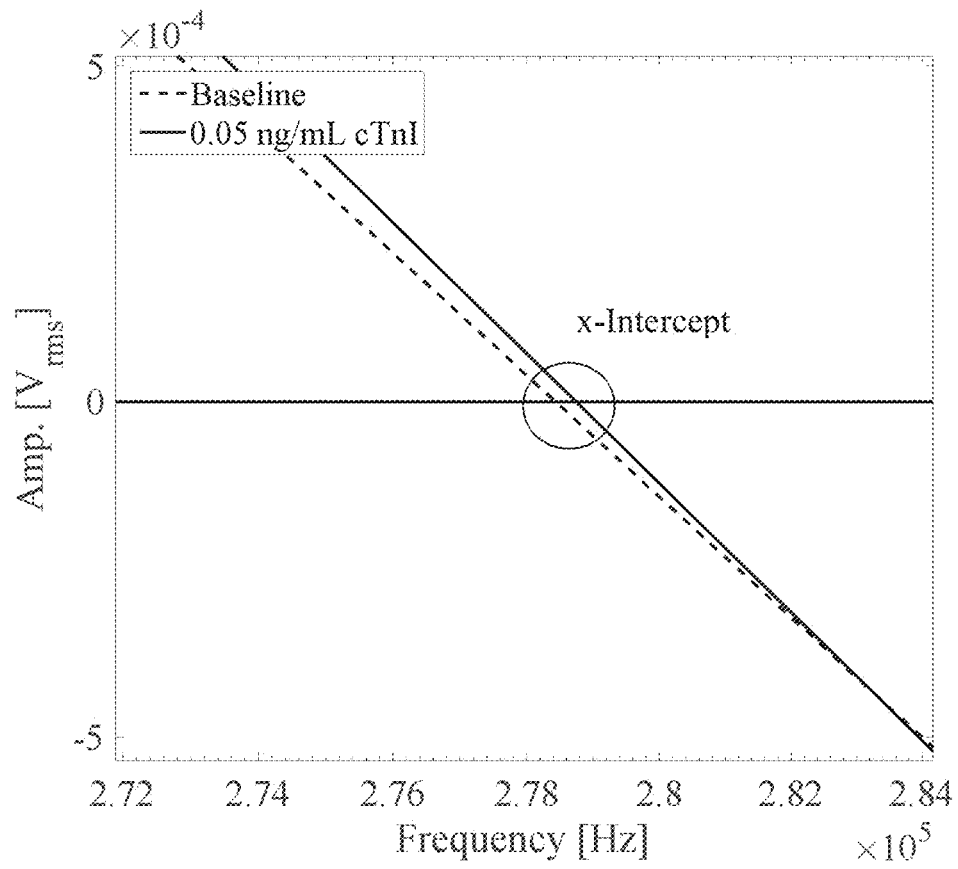

In Step 3.2, from the plot of Vrms vs frequency, the cut-off slope is calculated. As shown in FIGS. 20($a$)-($b$) demonstrating the calculation of the cut-off slope, the cut-off starts after the resonance peak, followed by taking the first polynomial fit to calculate the slope $\Delta y/\Delta x$ with difference to baseline. The calculation of the cut-off frequency in Step 3.3 is demonstrated in FIGS. 21($a$)-($b$). The cut-off frequency corresponds to the frequency at the lowest amplitude of the resonance peak (the end of the resonance peak). It is calculated from the first polynomial fit to the cut-off slope, as shown in FIG. 21($a$), followed by finding intersection of the two fitted curves (x-intercept). The x-intercept, as shown in FIG. 21($b$), is equal to the cut-off frequency. The cut-off frequency shift is calculated as a difference in the cut-off frequency between the control sensor (before adding an analyte solution) and then the sensor exposed to the analyte solution.

Figure 10:
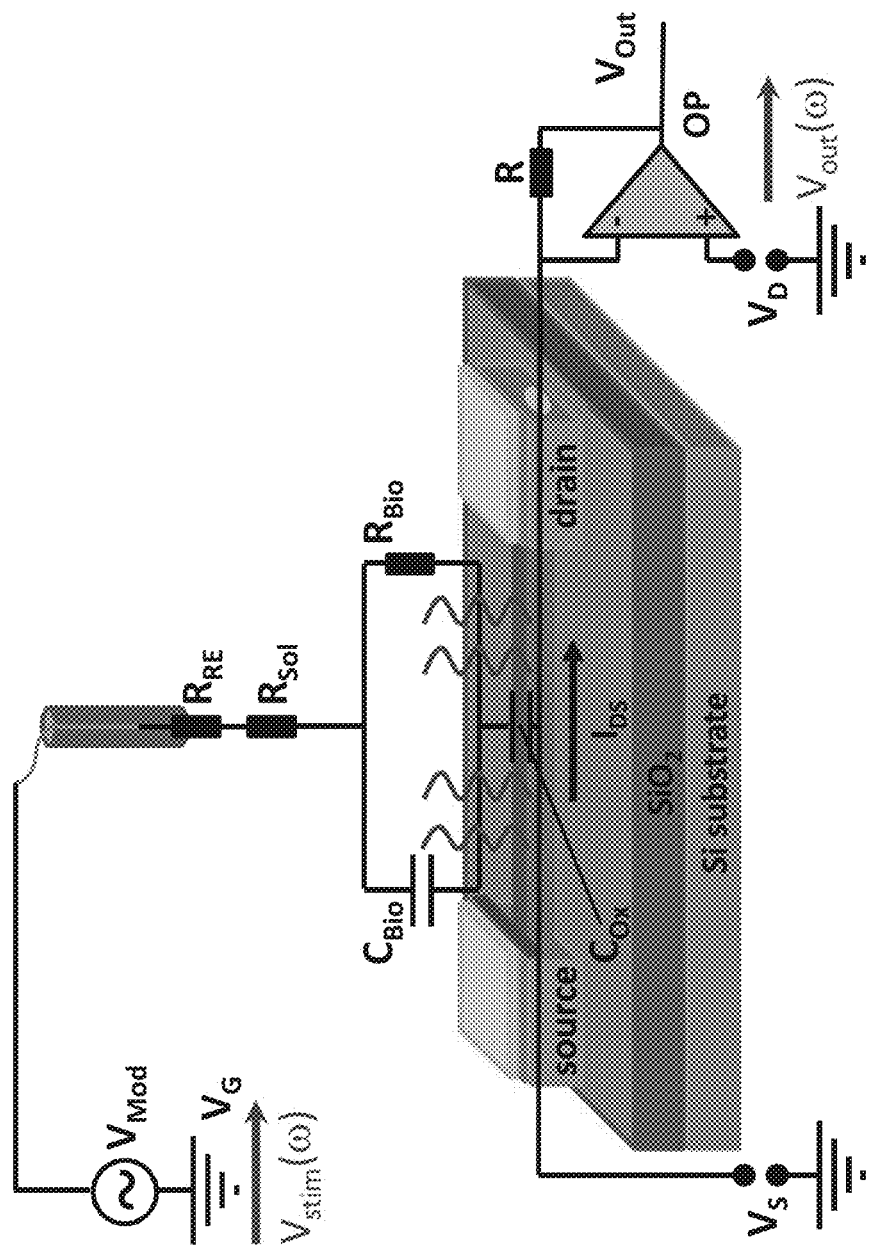
FIG. 10(a) illustrates an equivalent circuit of the pixel-based sensor of an embodiment.
FIG. 10(b) shows a simplified equivalent circuit of the pixel-based sensor of an embodiment.
FIG. 10(c) displays the theoretical transistor-transfer function in the most simplified form.
Figure 10:
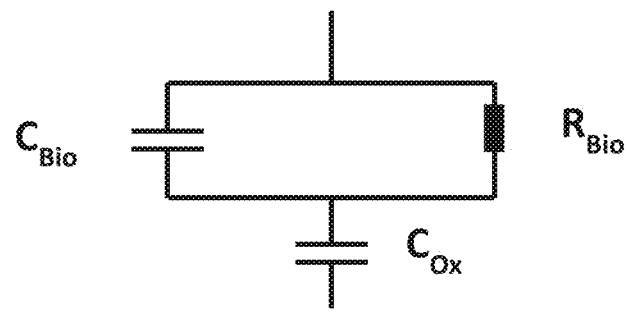
Figure 10:
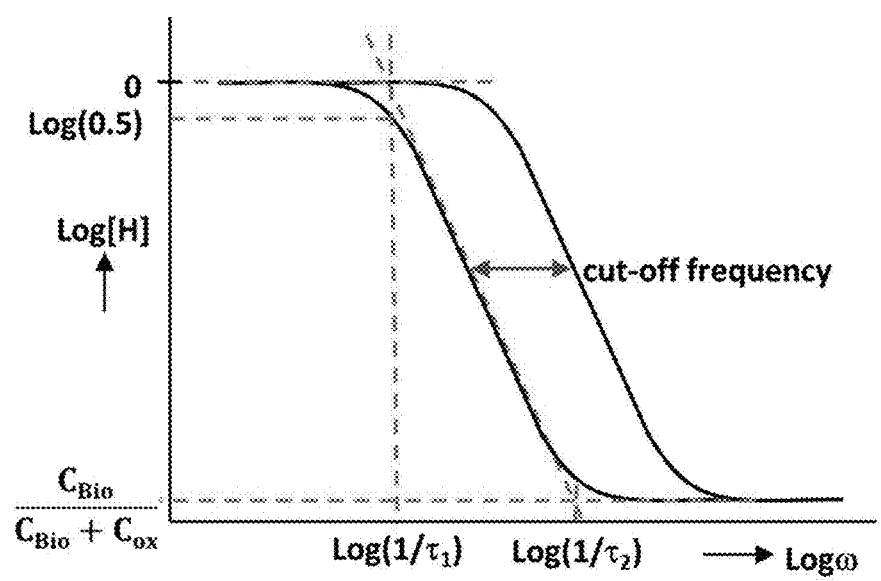

The detection parameter in the AC readout is a resonance peak, its amplitude and position. Like for the DC readout, the change in the recorded current of this peak is compared to the same peak in the spectrum of the control sample, i.e. the sensor with a functionalised surface before adding the analyte solution. Also a shift in the resonance frequency is referred to the control sample. The AC readout makes it possible to calculate the resistance and capacitance of the sensor as well as the cut-off frequency and the transition (resonance) frequency of the sensor, as shown in FIG. 10($c$) and described above.

Combination of both readout methods (DC and AC) allows overcoming their limits when used separately. This means, for example, that the DC-AC combined readout makes it possible to detect molecules that cannot be clearly identified with a single readout mode. For instance, a molecule with a neutral charge at respective pH would not be detectable in the DC mode at all, while in AC mode it would still cause an impedance change at the interface. Also, the combined DC-AC readout allows analysing the quality of the sensor's surface after each step of the surface functionalisation until the sensor is ready for detection of an analyte.

Moreover, calibration curves obtained from combined DC-AC measurements allow bypassing various uncontrollable parameters, such as blood content taken from different patients, thereby making the obtained data less sensitive to these parameters. In addition, this type of a multivariable readout offers the possibility to create fingerprints for the detected molecules to refer the detected signals back to a certain concentration of these molecules. In the experiments shown in the Examples section below, the importance of the multivariable data analysis is demonstrated. For instance, we used only the AC readout for cardiac troponin sensing, while for the three other protein assays shown in the examples (C-reactive protein, interferon-gamma induced protein and tumour necrosis factor related apoptosis inducing ligand), we used the combined DC-AC readout. Thus, the AC electronic readout combined with the DC readout is useful for enzymatic, electrochemical and affinity sensing when both charged and uncharged molecules are involved. When operated at higher frequencies (more than 1 MHz), the Debye screening can be overcome and also larger molecules can be sensed.

Figure 22:
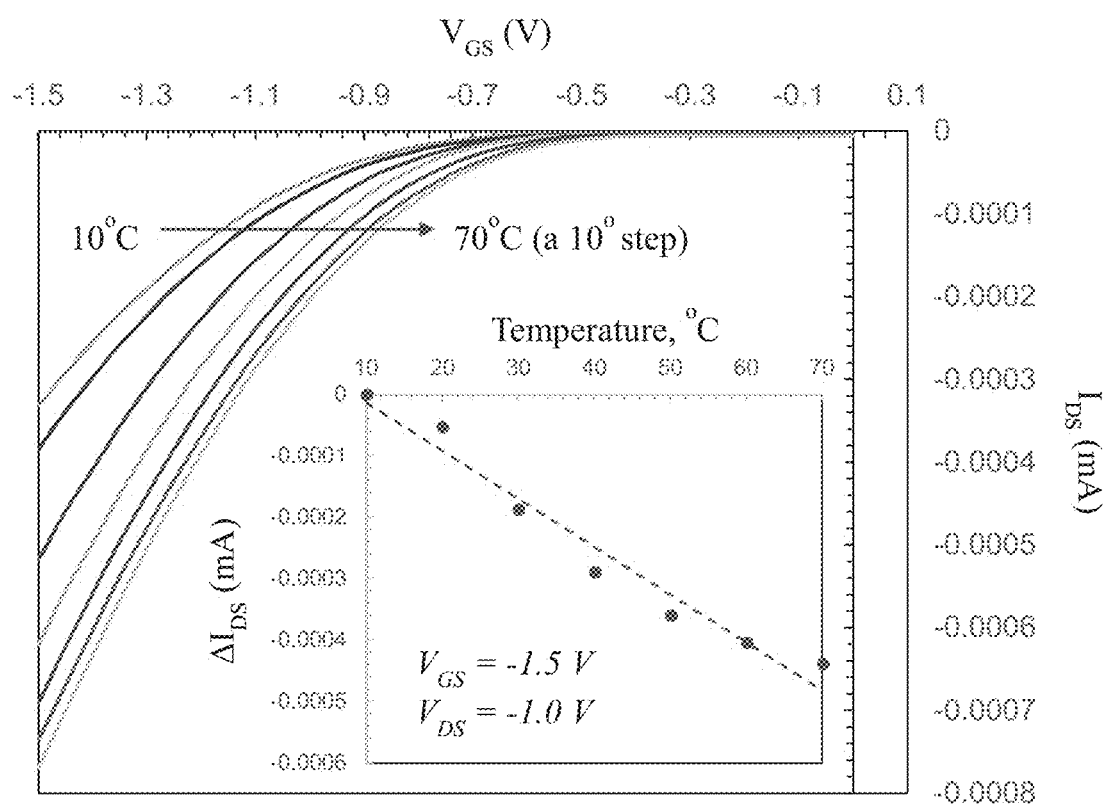
FIG. 22 shows a transfer characteristics for testing a bare silicon nanowire at different temperatures.

The third readout component in the triple readout is a temperature sensing for control of the assay and for reproducible sensing. FIG. 22 shows a transfer characteristics for testing a bare silicon nanowire at different temperatures with $V_{DS}$ kept constant at −1.0 V. It is clear from this figure that the SiNW current is dependent on temperature. Therefore, the temperature sensing is very important and should be included in the readout of the sensor.

In an embodiment, a method for the triple readout with a sensor of an embodiment comprises the combination of the DC and AC readout methods and the temperature sensing, as described above, and then plotting radar plots for a multi-parameter analysis of data received from the sensor of an embodiment, as will be demonstrated in the Examples section.

There are two methods for collecting data:
1) An end-point readout, which means the data is first collected from the control sensor (before adding the analyte solution) and then after the sensor is exposed to an analyte solution followed by a second recording after molecule binding; and
2) A time-dependent readout, which means the sensor is operated in a real-time recording mode (during the analyte binding or reaction with receptors) monitoring the changes in the current and transmitting the recorded data in real time.

EXAMPLES

Example 1: Measurements of the TTF of the Sensor

By performing the AC (alternating current) readout, the transfer function (TTF) of the sensor can be detected. The transfer function characterisation of the sensor was carried out by the experimental readout setup including the sensor of an embodiment and an external reference electrode, both placed into a flow cell. The AC readout setup also included a power supply and an amplifier. The working point was set at the maximum transconductance of the transfer characteristics curves measured directly before the transfer function measurement.

Figure 23:
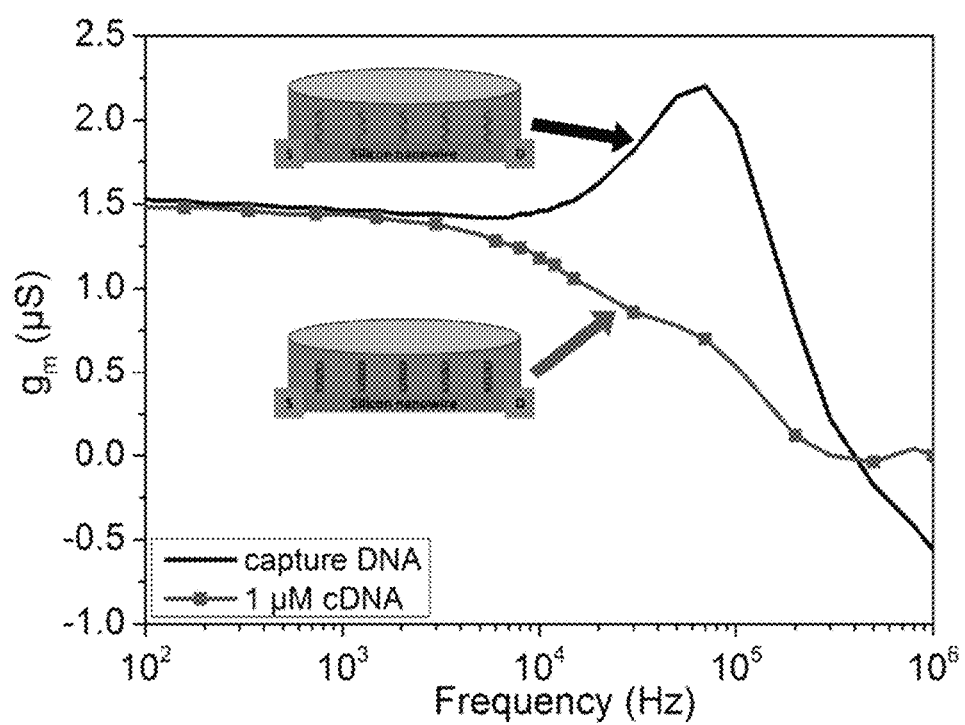
FIG. 23 shows an example of the TTF measurements before and after hybridisation of a DNA attached to the SiNW surface of the sensor.

Reference is now made to FIG. 23 showing an example of the TTF measurements before and after hybridisation of a DNA attached to the SiNW surface. The black line shows the TTF after immobilisation of a negatively-charged single-stranded capture DNA sequence. The red line shows the TTF after hybridisation with a complementary single-stranded target DNA sequence. The impedance of the sensor is changed after the hybridisation process, which is clearly visible by a shift of the TTF to lower transconductance values. Notably, the curve shape is different as in the simplified model in FIG. 10(c). The reason is that the aforementioned non-biological parameters are influencing the TTF shape a lot. However, it is also clear that the hybridization of the DNA molecules is largely influencing the impedance of the biomolecular layer $C_{Bio}$ and $R_{Bio}$.

Example 2: Conductivity Measurements

Figure 24:
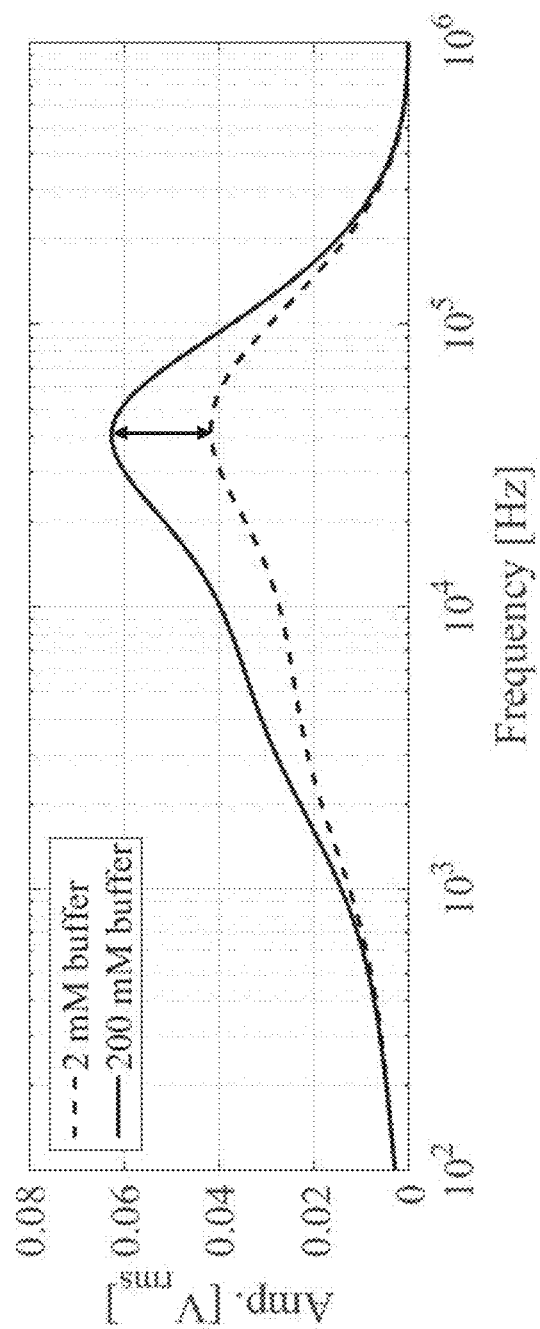
FIG. 24 shows the results of the AC readout measurements in 2 mM and 200 mM phosphate buffer pH 8.0.

Conductivity measurements with the sensor of an embodiment were performed in 2 mM and 200 mM phosphate buffer pH 8.0. The AC readout for both solutions was compared by comparing the obtained signal strength. FIG. 24 shows the results of this experiment. The difference of the AC readout measured in high-concentrated buffer solutions (200 mM; solid line) and in low-concentrated buffer solutions (2 mM; dashed line) is clearly observed and originated from the different conductivities of these solutions. After calibration, a pixel not modified with biomolecules could be used as ionic strength reference channel.

Figure 25:
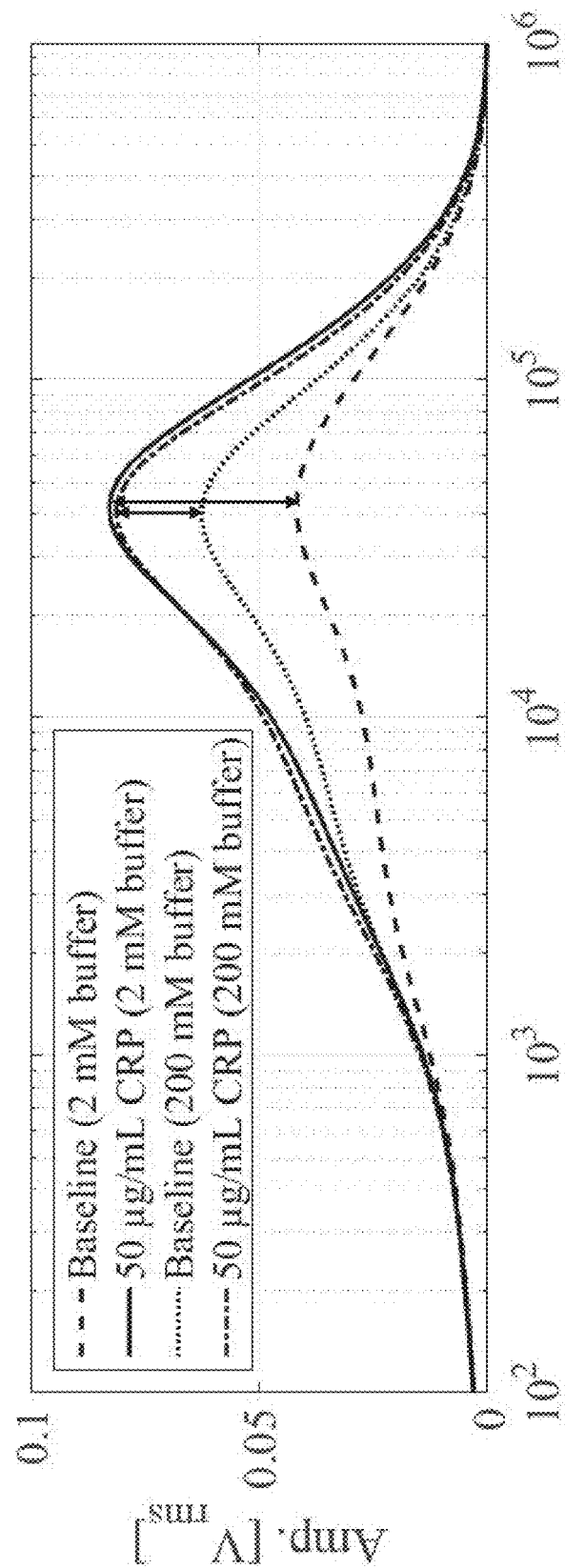
FIG. 25 shows the results of the AC readout measurements for two consecutive experimental steps for the 50 µg/mL CRP solution in 2 mM phosphate buffer and of two consecutive experimental steps for the 50 µg/mL CRP solution in 200 mM phosphate buffer.

In a further experiment, two solutions of the CRP (C-reactive protein) were prepared: 50 µg/mL of the CRP in 2 mM phosphate buffer and 50 µg/mL of the CRP in 200 mM phosphate buffer pH 8.0. The AC readout for two consecutive experimental steps measured in 2 mM phosphate buffer and of two consecutive experimental steps measured in 200 mM phosphate buffer was performed. The results of this experiment are shown in FIG. 25. The signal strength is slightly decreased in high-concentrated buffer solutions compared to low-concentrated buffer solutions. The reason for such opposite trend can be only the Debye screening discussed above, which is partly affecting the total impedance change caused by the molecular binding in the biomolecular layer. It can also be noted that unlike in experiments with only DC recording, the binding of the target molecules in the TTF approach can also be detected in physiological electrolyte concentration of 200 mM. The reason is that the charge of the biomolecules in the TTF approach is just one of many influencing factors of the impedance change at the SiNW surface as noted above.

Example 3: Characterisation of the Sensor

Figure 26:
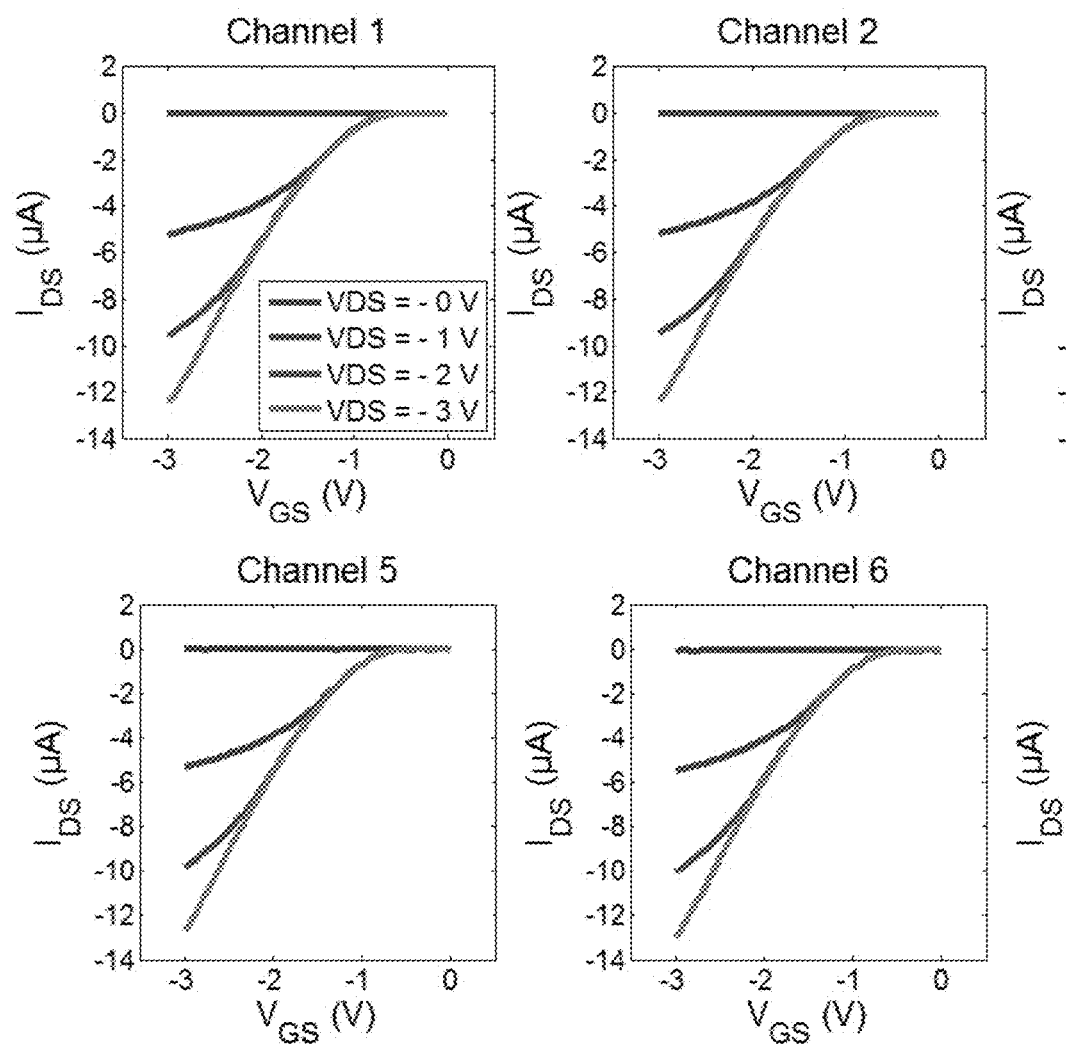
FIGS. 26(a)-(b) shows the plotted transfer function of all 8 channels of the 8-channel sensor chip ($I_{DS}$ vs. $V_{GS}$ at constant $V_{DS}$ as indicated in the plot).
FIG. 26(c) shows the transfer characteristic curves of all 8 channels of the chip plotted in one graph (constant $V_{DS}$ of −3V for all eight channels).
Figure 26:
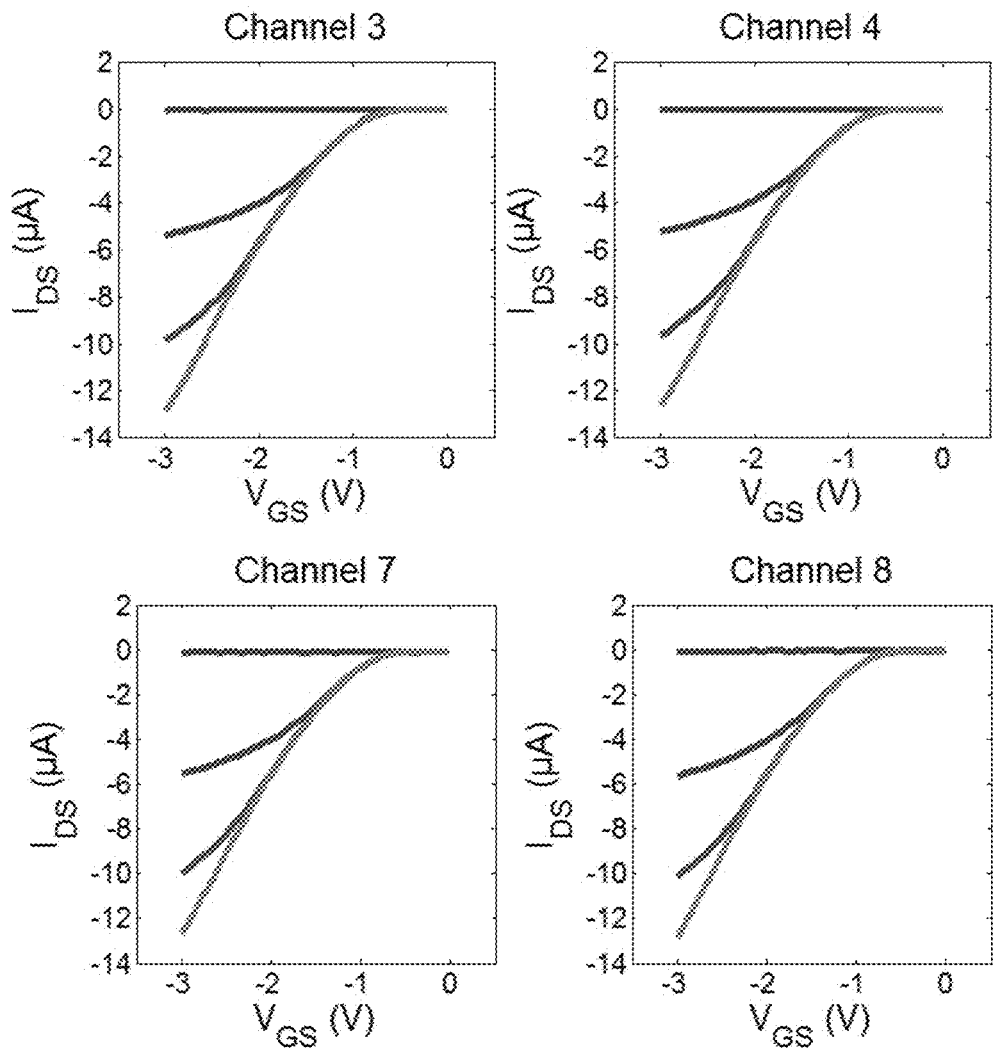

The sensor of an embodiment, which was encapsulated via the flip-chip process shown in FIG. 3(h), is characterised electronically. In FIG. 26(a)-(b), the transfer function of all 8 channels out of one chip are plotted ($I_{DS}$ vs. $V_{GS}$ at constant $V_{DS}$ as indicated in the plot). The sensor behaves like an ideal long-channel FET device with $I_{DS}$ currents in the µA range.

Due to the top-down batch processing of the sensor, there is a large reproducibility. This is shown in FIG. 26(c), where the transfer characteristic curves of all 8 channels of the chip are plotted in one graph (constant $V_{DS}$ of −3V for all 8 SiNWs). When a working point of this device of $V_{DS}=-3V$, and $V_{GS}=-3V$ is chosen, the electronic error is found below 2.5% (12.7+/−0.3 µA which corresponds to an error of less than 2.5%). Thus, the channel-to-channel reproducibility is very high in this sensor. Moreover, in an industry-upscale, this error will be clearly further reduced.

Example 4: Multiple Parameter Data Analysis

Multiple parameters obtained from the combined AC-DC readout described above can be plotted in one graph in order to identify target molecules, calculate their concentration or monitor various changes occurring in the medium, to which the sensor is exposed. Non-limiting examples of such plots are: voltage shift versus amplitude difference, voltage shift versus cut-off frequency shift, $g_m$ shift versus amplitude difference and $g_m$ shift versus cut-off frequency shift. In order to visually represent the data, multiple-axis radar plots can be used. In fact, the radar plots allow identifying the target molecule binding concentration using several parameters, thereby making possible to program a neuronal network, which would recognise certain structure and create a library. In addition, the radar plots can increase accuracy and decrease errors caused by a single parameter measurement. For example, the radar plots can provide more information about the surface activity, charges and layer thickness, etc. Also, the radar plots can determine isoelectric points of some target molecules, when no meaningful DC signal detection is possible.

Figure 27:
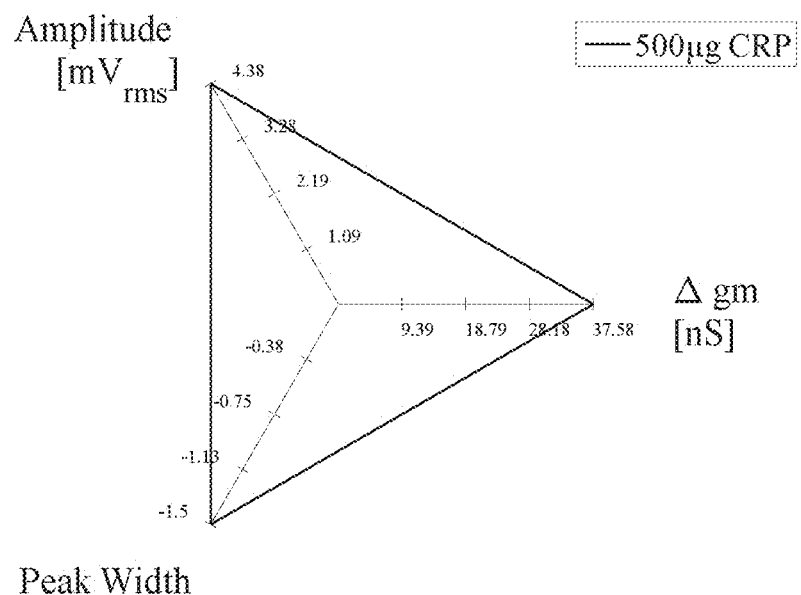
FIG. 27 shows a three-axis radar plot for the CRP detection in solution.
Figure 27:
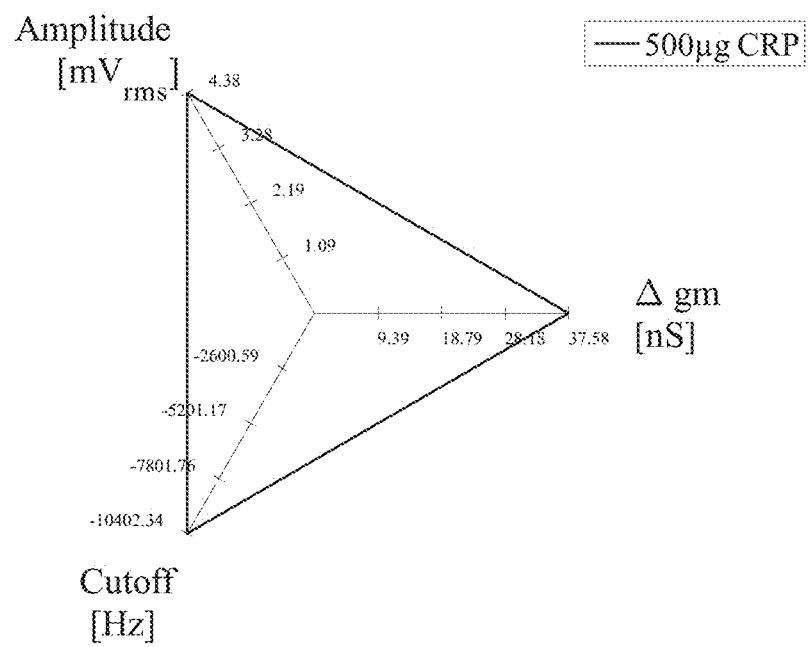
Figure 28:
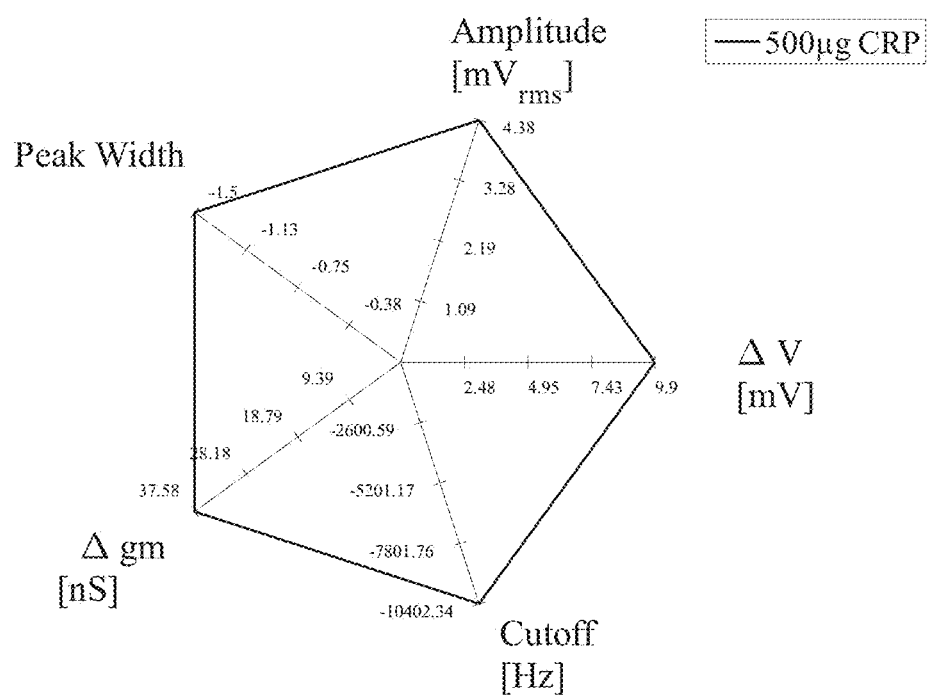
FIG. 28 shows a five-axis radar plot for the CRP detection in solution.

FIG. 27 shows a three-axis radar plot with one DC parameter and two AC parameters for CRP detection in solution. The plotted parameters are characteristic for the CRP in solution. In FIG. 27(a), the parameters are $g_m$ obtained from the DC readout and the peak width and amplitude obtained from the AC readout, while in FIG. 27(b), the parameters are $g_m$ obtained from the DC readout and the amplitude and cut-off frequency obtained from the AC readout. All the parameters obtained from the DC and AC readouts can be mixed and matched in different radar plots. FIG. 28 shows a five-axis radar plot for the CRP detection in solution.

Example 5: Radar Plots for Concentration Determination

Figure 29:
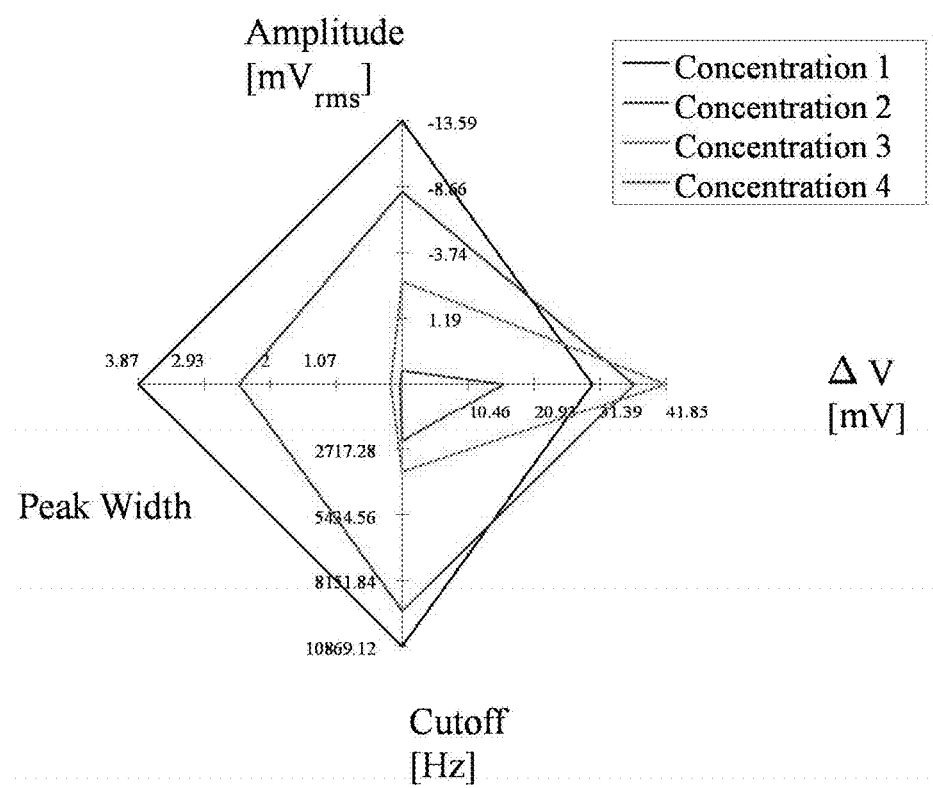
FIG. 29 shows the four-axis radar plot with an amplitude and width of the resonance peak, voltage shift ΔV, and cut-off frequency obtained in the CRP detection

Radar plots with several parameters can be used to determine concentration of an analyte in solution. In addition, using these plots make it possible to cancel out parameters that show false positive results and therefore, are not suitable for detection. FIG. 29 shows the four-axis radar plot with an amplitude and width of the resonance peak, voltage shift ΔV, and cut-off frequency obtained in the CRP detection. Change from concentration 1 to 3 is consistent for all four measured parameters, while concentration 4 is detectable only with three AC parameters (amplitude, peak width and cut-off frequency), but not in a DC mode (voltage shift).

Figure 30:
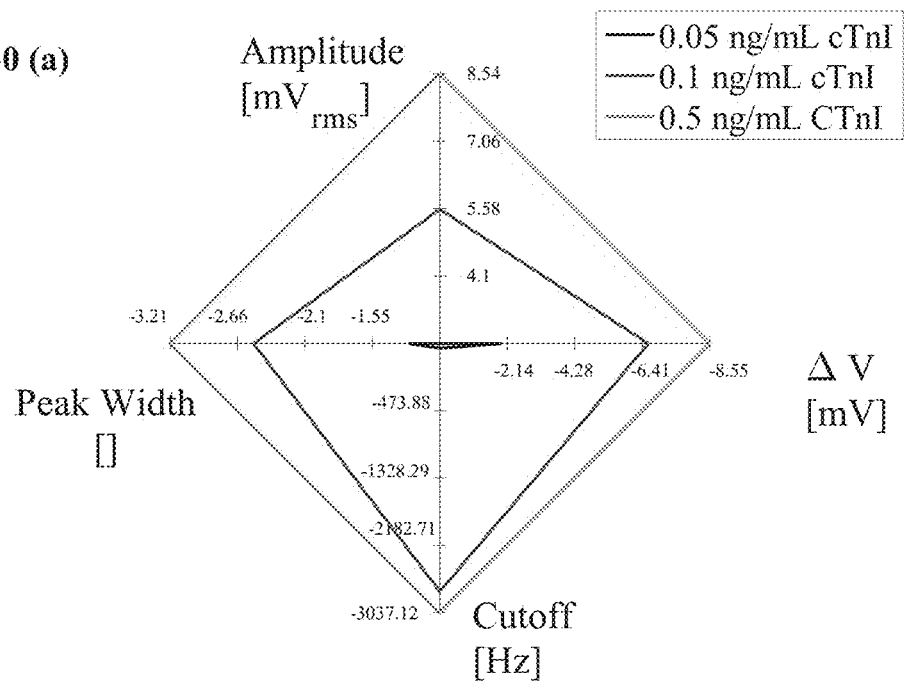
FIG. 30(a) shows the 4-axis radar plot for determination of the troponin concentration in 2 mM phosphate buffer.
FIG. 30(b) shows the 4-axis radar plot for determination of the troponin concentration in 200 mM phosphate buffer.
Figure 30:
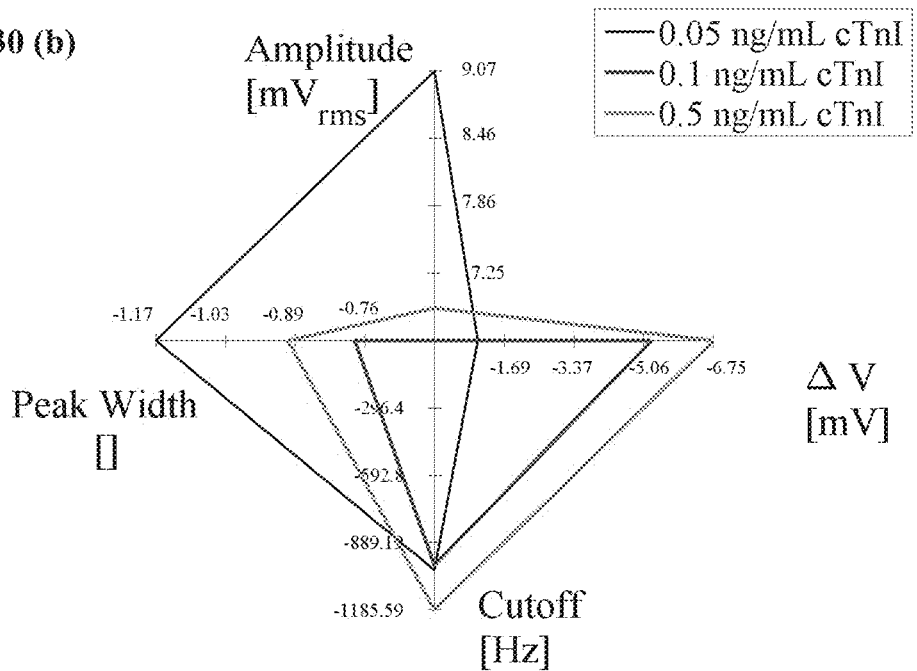

FIG. 30(a) shows the 4-axis radar plot for determination of the troponin concentration in 2 mM buffer, while FIG. 30(b) shows the same radar plot for troponin dissolved in 200 mM buffer. These plots demonstrate some ionic effect of the buffer. In a weakly concentrated buffer, increasing the concentration of troponin is consistently detected by all four parameters, but once the ionic strength of the buffer increases, all three AC parameters unexpectedly fall out leaving only the voltage shift usable in the concentration measurements. Please note that these plots are shown only to exemplify the method for the concentration-dependent measurements using the sensor of an embodiment with a multiparameter data analysis. Further embodiments of this method are currently under development by the present inventors.

In conclusion, radar plots show that the change in the concentration of an analyte can be detected by different parameters in the AC and DC readout mode. Single parameters can be cancelled out if they show instability at a certain assay, thereby increasing accuracy of the assay and avoiding false positive detection.

Example 7: Troponin Affinity Binding Assay

The troponin complex is a heteromeric protein playing an important role in the regulation of skeletal and cardiac muscle contraction. It is released into the blood stream upon heart muscle damage. The marker consists of 3 subunits: Troponin T (TnT), Troponin I (TnI), and Troponin C (TnC). Amongst all, TnI is only expressed in myocardium. The markers are detectable in patient's blood 3-6 hours after onset chest pain and even 10 days after heart attack. The assay demonstrated below is focused on detection of only cTnI (human cardiac troponin I) (normal concentration range is less than 0.15 ng/ml, isoelectric point pI is in the range 5.4-9.87).

The sensor chip of an embodiment was cleaned and activated with Piranha solution and then silanised with 3-(glycidyloxypropyl)trimethoxysilane (GPTES). The GPTES epoxy ring was opened at pH 8.5-9.0, followed by the covalent binding of the terminal amino group of a cTnI aptamer at 37° C. overnight. This resulted in a shift of the transfer characteristics to higher $V_{FG}$ values, since the cTnI aptamer has a negatively charged backbone. In the next step, the sensor's surface was treated with 1 mM ethanolamine for 30 min at room temperature to avoid unspecific binding of the cTnI protein to the surface and cancel out false positive results. The control measurements were carried out with 2 mM and 200 mM phosphate buffer pH 8. The cTnI analyte in 2 mM phosphate buffer was incubated for 60 min and bound to the sensor's surface through the cTnI aptamer, followed by the measurements in 2 mM and 200 mM phosphate buffer pH 8.

Figure 31:
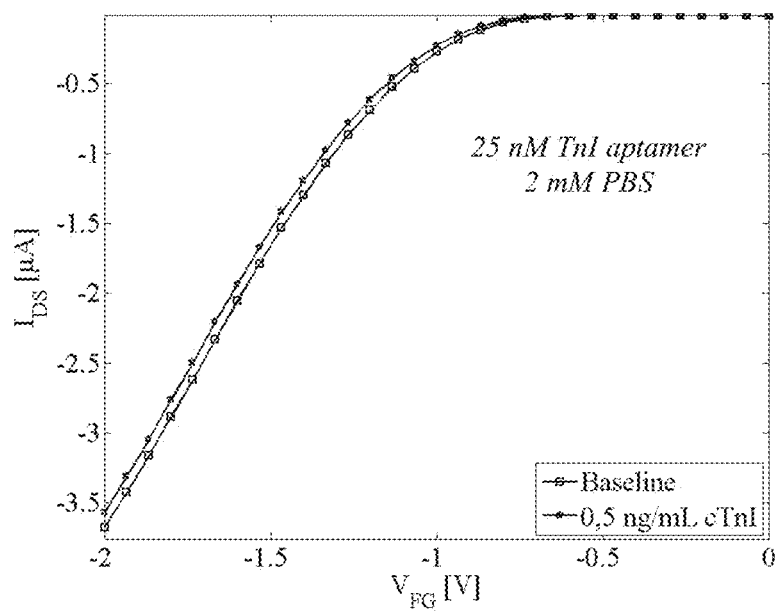
FIG. 31 shows the DC readout in detection of 0.5 ng/mL cTnI in (a) 2 mM phosphate buffer and (b) in 200 mM phosphate buffer.
Figure 31:
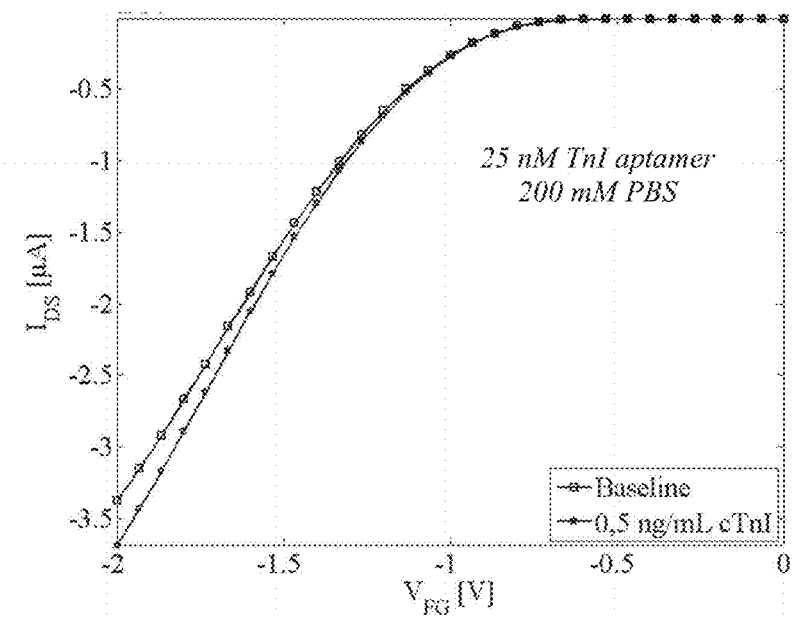

FIG. 31 shows the DC readout in detection of 0.5 ng/mL cTnI in (a) 2 mM phosphate buffer, shift to lower $V_{FG}$ value, and (b) in 200 mM phosphate buffer, shift to higher $V_{FG}$ value, thereby rendering the voltage shift parameter inconsistent in troponin measurements.

Figure 32:
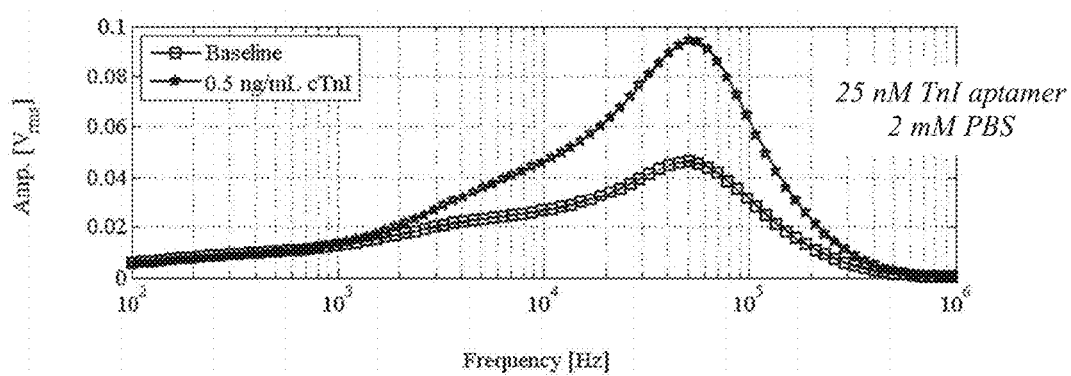
FIG. 32 shows the AC readout of 0.5 ng/mL cTnI in (a) 2 mM phosphate buffer and (b) 200 mM phosphate buffer.
Figure 32:
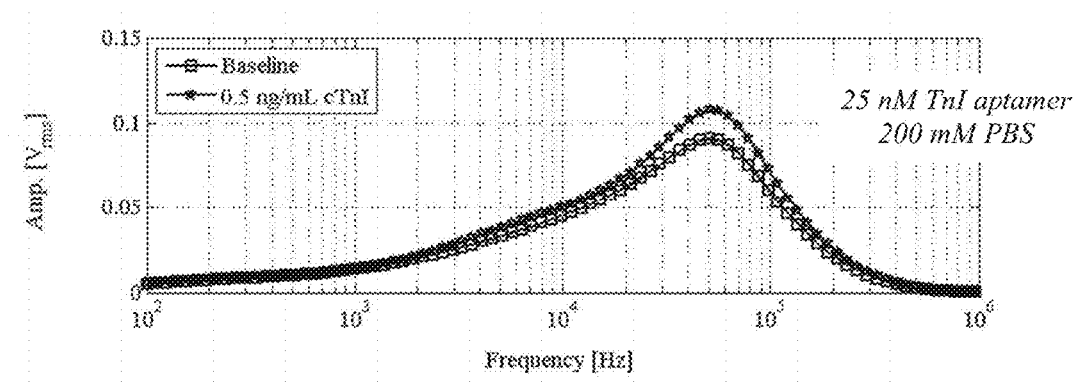
Figure 33:
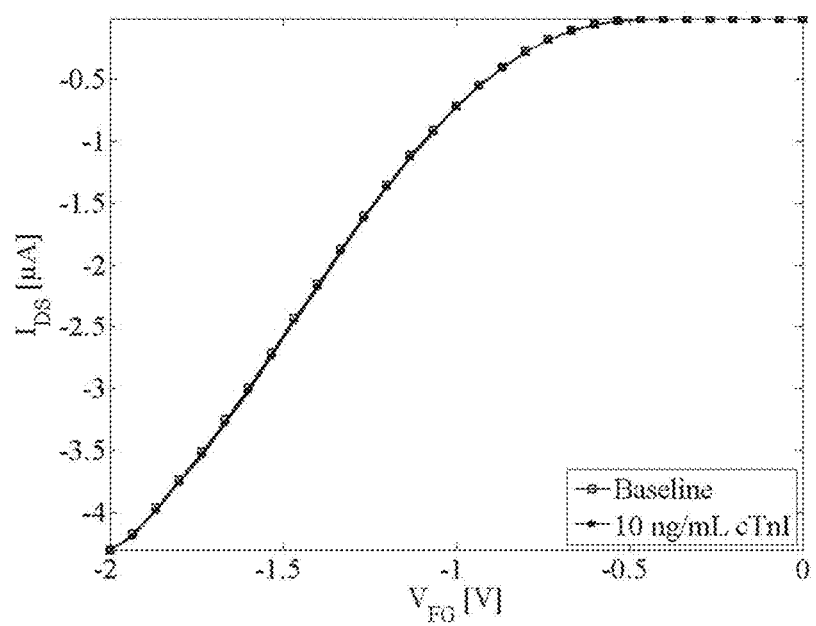
FIG. 33 shows a control experiment in detection of cTnI with no aptamer immobilised on the surface of the sensor.
Figure 34:
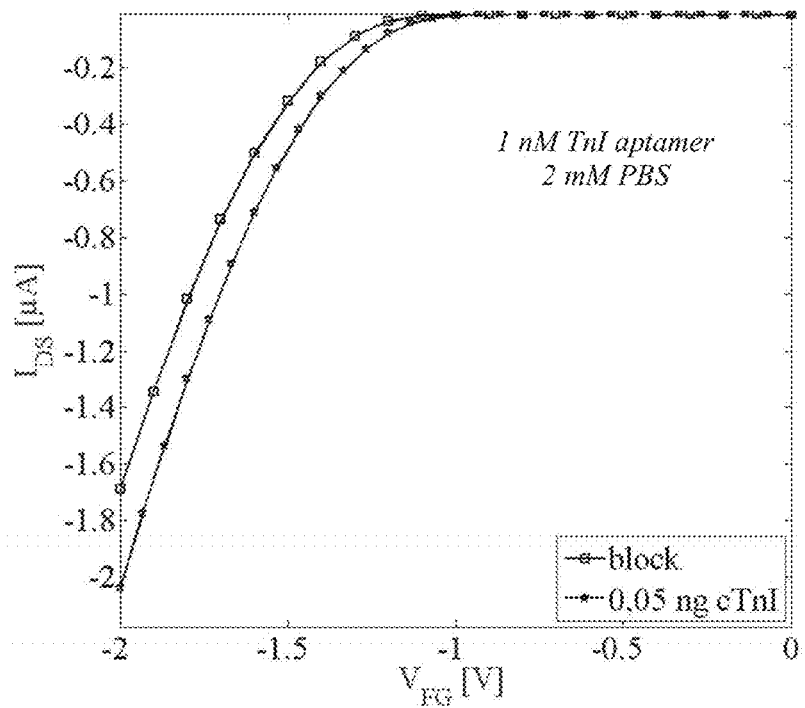
FIG. 34 shows the DC readout in detection of 0.05 ng/mL cTnI in (a) 2 mM phosphate buffer and (b) in 200 mM phosphate buffer.
Figure 34:
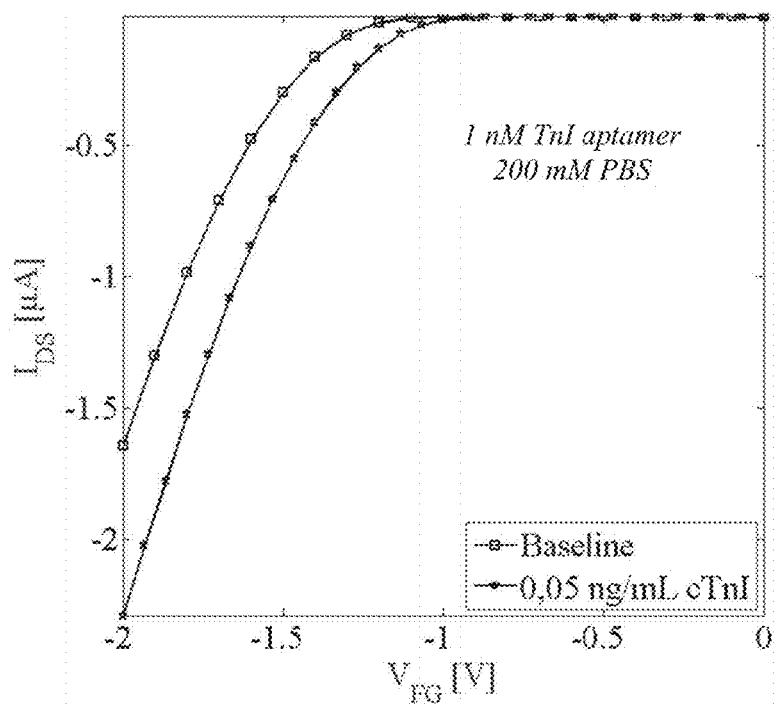
Figure 35:
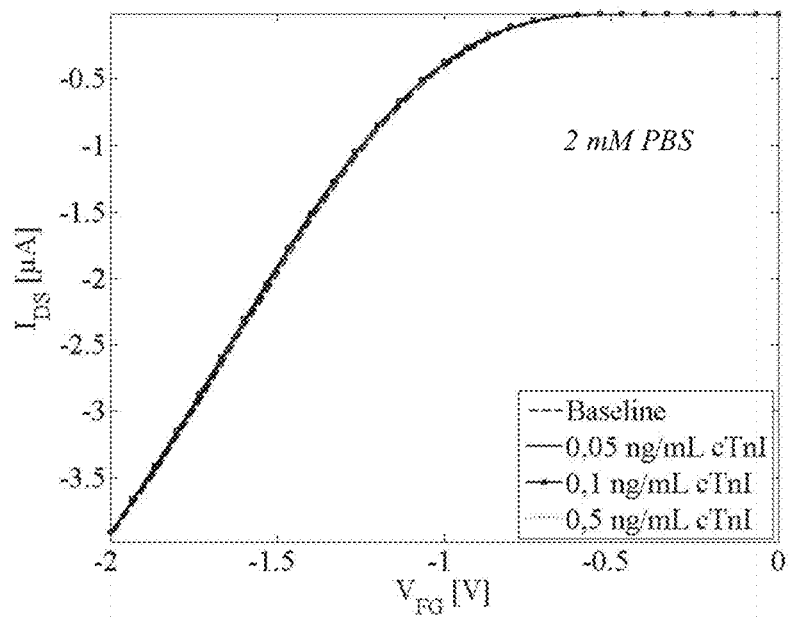
FIG. 35 shows the concentration-dependent DC measurements of the cTnI in (a) 2 mM phosphate buffer and (b) in 200 mM phosphate buffer.
Figure 35:
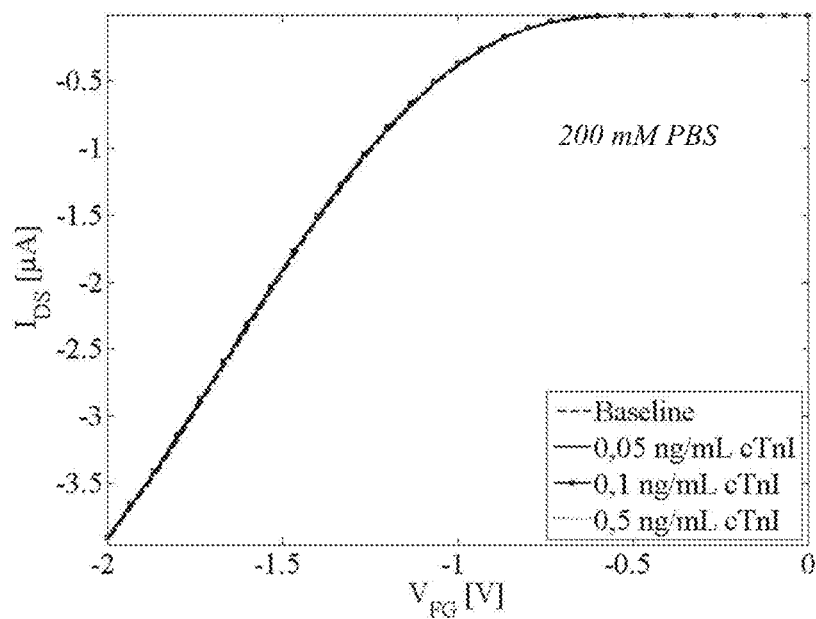

FIG. 32 shows the AC readout of 0.5 ng/mL cTnI in (a) 2 mM phosphate buffer and (b) 200 mM phosphate buffer, with clearly visible shift to higher values after the cTnI binding to the aptamer. FIG. 33 shows a control experiment with no aptamer immobilised on the surface of the sensor, and consequently, no voltage shift is observed. FIG. 34 shows the DC readout in detection of 0.05 ng/mL cTnI in (a) 2 mM phosphate buffer and (b) in 200 mM phosphate buffer, with clearly observable voltage shift to higher $V_{FG}$ values in both cases. FIG. 35 shows the concentration-dependent DC measurements of the cTnI in (a) 2 mM phosphate buffer and (b) in 200 mM phosphate buffer. There is almost no visible change in the voltage in both cases, which supports the above conclusion that it is not feasible to detect the troponin only by DC readout.

Figure 36:
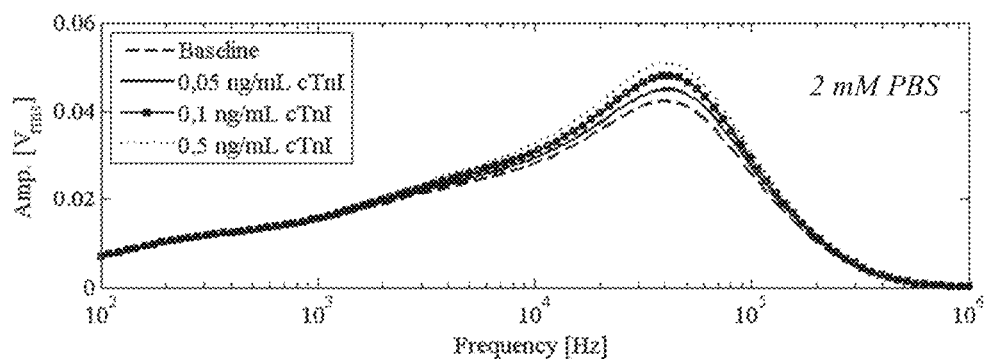
FIG. 36 shows the concentration-dependent measurements in the AC readout mode of the cTnI in (a) 2 mM phosphate buffer and (b) in 200 mM phosphate buffer.
Figure 36:
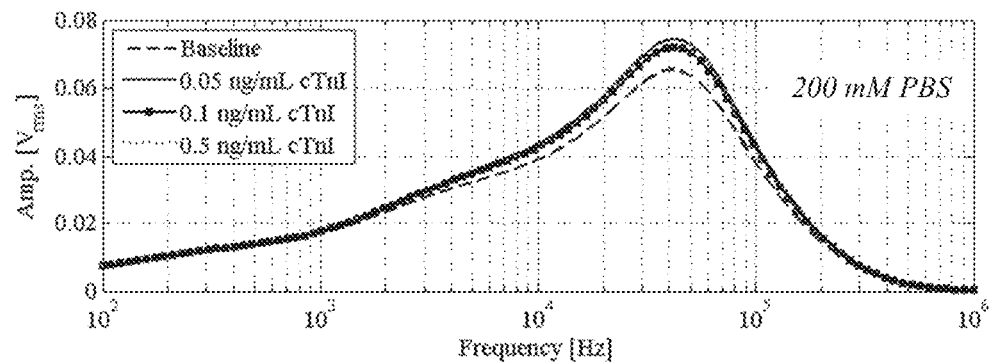

FIG. 36 shows the concentration-dependent measurements in the AC readout mode of the cTnI in (a) 2 mM phosphate buffer and (b) in 200 mM phosphate buffer, clearly supporting the idea that the sensor an embodiment can be used in the very low concentration measurements of the biomolecules (the troponin concentration in the assay was 0.05 ng/ml-0.5 ng/ml). Since the normal physiological concentration of the troponin is less than 0.15 ng/ml, the sensor of an embodiment could successfully detect it in blood serum as well.

In addition, it should be noted that the transfer characteristic is dependent on the charge of a protein. Since cTnI has a pI value of 5.4-9.87, it can be either positively or negatively charged in the buffer (pH 7-8). Therefore, the DC readout mode should be avoided in the troponin detection. On the other hand, the transfer function measurements (in AC mode) are very important in this case, because binding of the troponin to its selective aptamer causes a change in capacitance and impedance of the sensor. The specificity and affinity of the troponin aptamer also play an important role here. Thus, the troponin demonstrates an example for detection of a protein having wide or unknown range of pI. In such case, the multiparameter data analysis as described in an embodiment is essential.

Example 8: TRIAL Protein Assay

TNF-related apoptosis-inducing ligand (TRAIL) is a protein functioning as a ligand that induces the process of cell death or apoptosis. TRAIL is a cytokine that is produced and secreted by most normal tissue cells. The study shows that TRAIL was consistently up-regulated in viral infected patients. The interesting clinical range is 10-200 ng/ml and the isoelectric point is pI=7.01-7.2. Therefore, TRAIL is negatively charged in phosphate buffer at pH 8.0.

Procedure for immobilisation of the TRIAL aptamer onto the sensor's surface is similar to the immobilisation of the troponin aptamer. The surface was cleaned and activated with Piranha solution and then silanised with GPTES. The TRIAL aptamer was immobilised with two different concentrations: 1 nM and 100 nM, followed by blocking the sensor's surface with 1 mM ethanolamine to prevent unspecific binding of the protein during the experiments. Four different TRAIL protein concentrations were measured: 10 ng/mL, 50 ng/mL, 100 ng/mL and 200 ng/mL. Two control sensor chips were measured: one with no aptamer immobilised on the surface, but incubated with 200 mM phosphate buffer at 37° C. overnight, and one blank sensor chip incubated at 37° C. without buffer and measured only in buffer.

Figure 37:
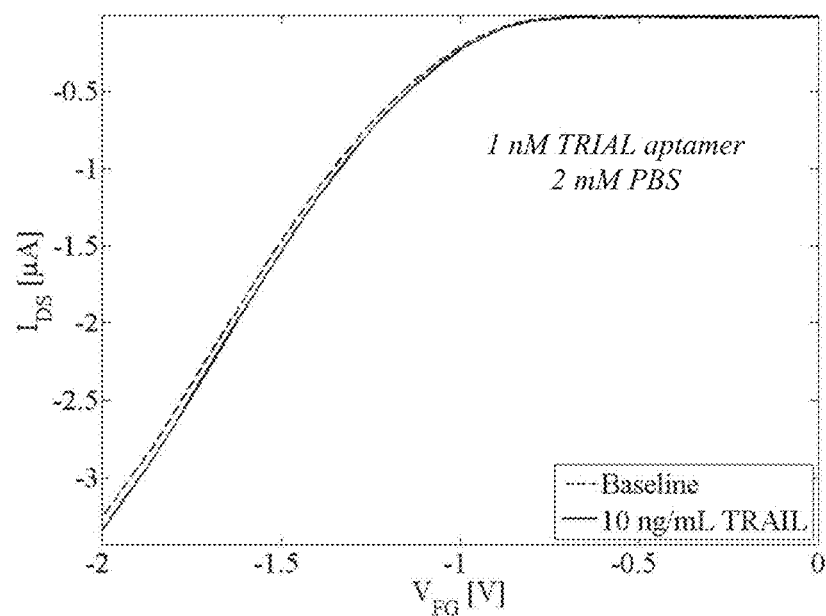
FIG. 37 shows the detection of 10 ng/mL TRAIL in (a) 2 mM and (b) 200 mM phosphate buffer with 1 nM TRIAL aptamer in a DC readout mode.
Figure 37:
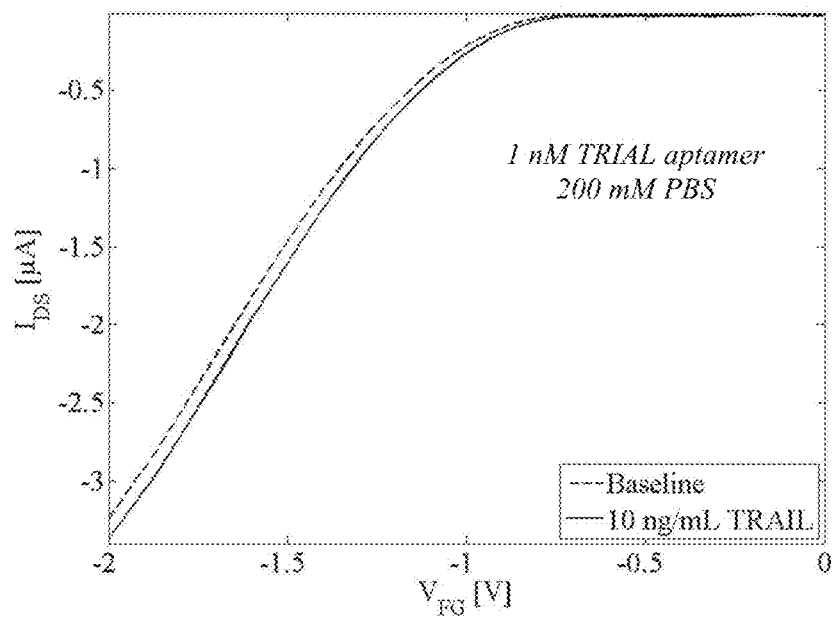
Figure 38:
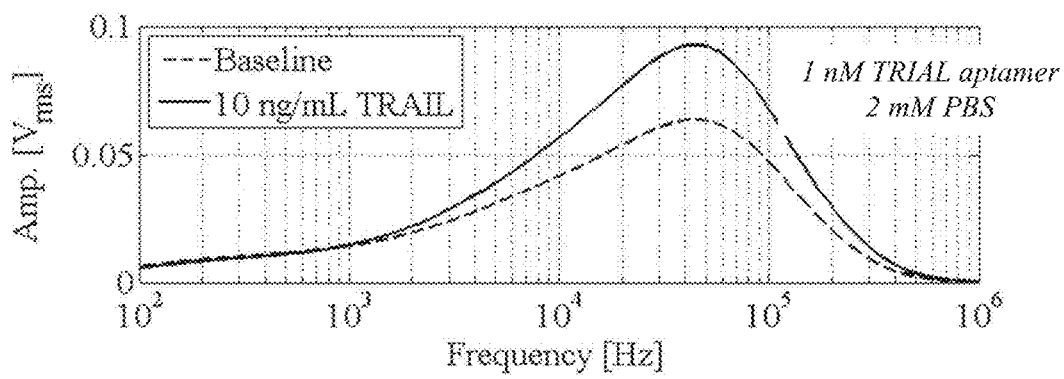
FIG. 38 shows the detection of the 10 ng/mL TRAIL in (a) 2 mM and (b) 200 mM phosphate buffer with 1 nM TRIAL aptamer in an AC readout mode.
Figure 38:
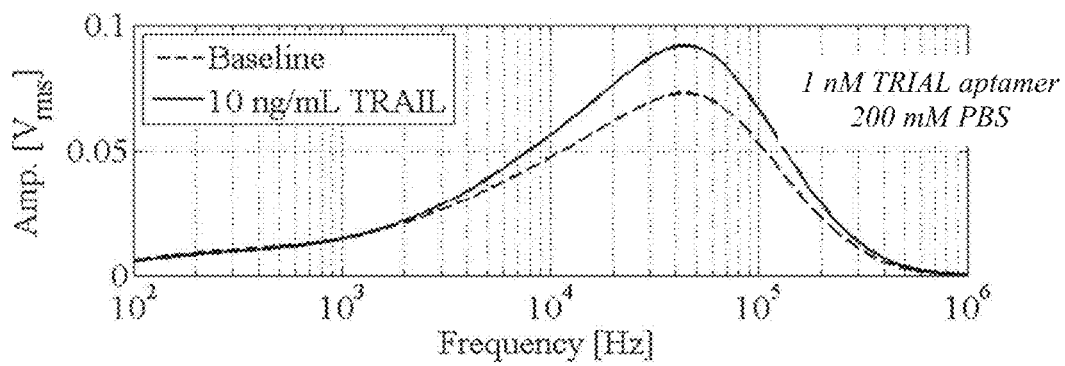
Figure 39:
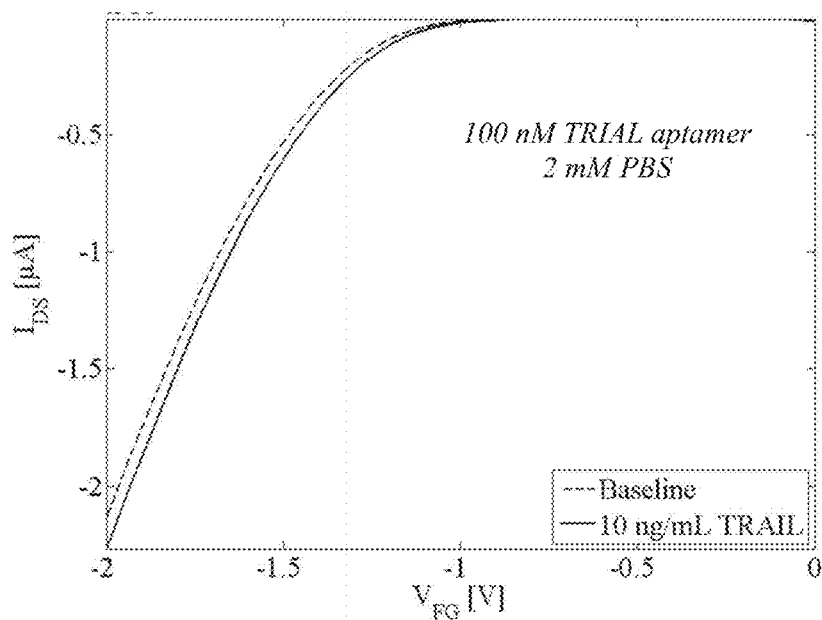
FIG. 39 shows the detection of 200 ng/mL TRAIL in (a) 2 mM and (b) 200 mM phosphate buffer with 100 nM TRIAL aptamer in a DC readout mode.
Figure 39:
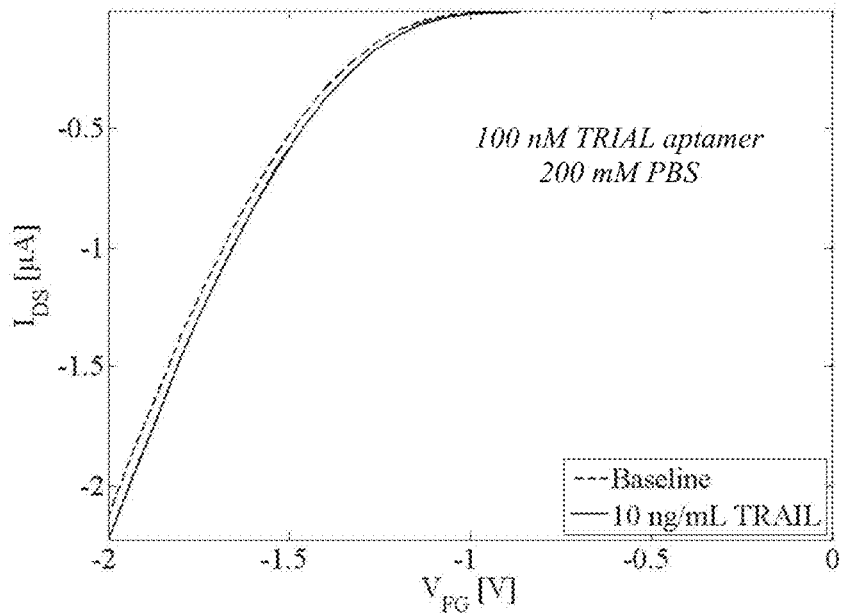
Figure 40:
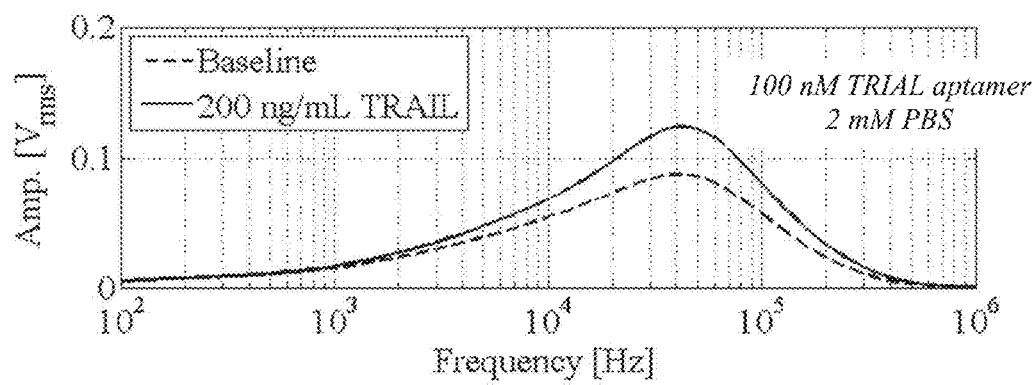
FIG. 40 shows the detection of the 200 ng/mL TRAIL in (a) 2 mM and (b) 200 mM phosphate buffer with 100 nM TRIAL aptamer in an AC readout mode.
Figure 40:
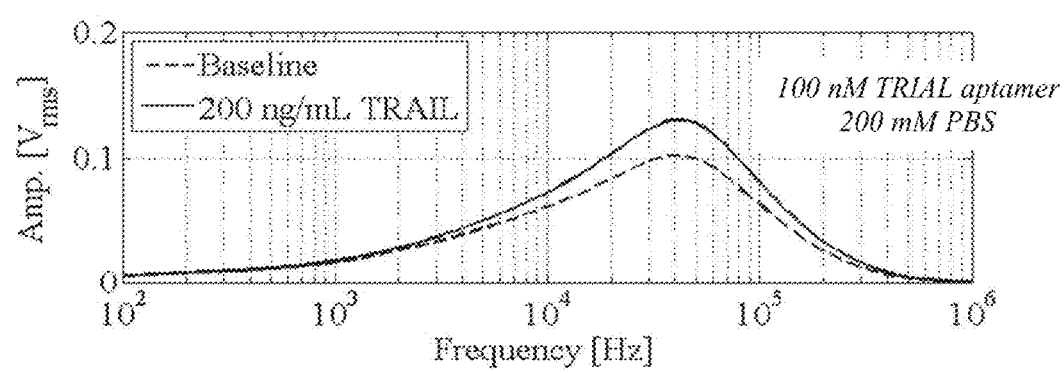

FIG. 37 shows the successful detection of 10 ng/mL TRAIL in (a) 2 mM and (b) 200 mM phosphate buffer with 1 nM TRIAL aptamer, while FIG. 38 shows the same successful detection of the 10 ng/mL TRAIL in an AC readout mode. Binding of 10 ng/mL TRAIL clearly results in an increase of the AC transfer function. The same successful results are shown in FIGS. 39 and 40, demonstrating the operation of the sensor the DC readout mode and in the AC readout mode, respectively.

In conclusion, the TRAIL protein was detected using the sensor of an embodiment in combined DC and AC readout modes, and in the concentration range of 10-200 ng/ml corresponding to the clinically important range of the TRAIL protein. Both transfer characteristic and transfer function measurements (in 2 mM and in 200 mM phosphate buffer) were successful.

The invention claimed is:

1. An electrical circuit element, defined as "pixel", comprising:
at least one silicon nanowire open for contact with a medium;
a metal electrode open for contact with said medium for feeding a high-frequency sinusoidal AC stimulation in impedance measurements and for sensing properties of said medium, wherein said metal electrode is a temperature sensor, or both a counter electrode and temperature sensor, simultaneously;
implanted source and drain electrodes connected to said silicon nanowire and leaving a gate area of said pixel and parts of said electrode open for contact with said medium;
electrical metal contacts for connecting said pixel to an electrical circuit; and
a reference electrode open for contact with said medium for creating a three-electrode-cell system and providing a constant gate potential in the circuit.

2. The pixel of claim 1, further comprising a backgate contact for the full electrostatic control of said pixel and for stabilising the electronic recording in electrolyte solutions.

3. The pixel of claim 1, wherein said silicon nanowire is low-doped p-type, low-doped n-type, drain n-doped and source p-doped, or drain p-doped and source n-doped.

4. The pixel of claim 1, wherein said metal electrode is a noble metal counter electrode.

5. The pixel of claim 4, wherein said noble metal is platinum, gold or copper.

6. The pixel of claim 1, wherein said reference electrode is an Ag/AgCl reference-cell electrode.

7. The pixel of claim 1, wherein said metal electrode and said reference electrode are not passivated and in direct contact with said medium.

8. The pixel of claim 1, wherein the surface of said silicon nanowire is coated with pH-sensitive oxide or nitride dielectric for use as a pH-reference element.

9. The pixel of claim 8, where said pH-sensitive oxide or nitride dielectric is made of $SiO_2$, $Al_2O_3$, $Ta_2O_5$, $HfO_2$, $TiO_2$, $ZrO_2$, TiN or $Si_3N_4$.

10. The pixel of claim 9, where said pH-sensitive oxide dielectric is made of $Al_2O_3$ or $Ta_2O_5$.

11. The pixel of claim 1, wherein the surface of said silicon nanowire is coated with either a metal- or a molecular-passivation layer for negating the pH-sensitivity of said surface and consequently using the sensor as a solution conductivity reference element for pure ionic strength sensing.

12. The pixel of claim 11, where said metal-passivation layer is made of Au, Pt, Al, Wo, or Cu.

13. The pixel of claim 1, further comprising a back gate at the bottom for tuning a threshold voltage.

14. The pixel of claim 1, wherein the surface of said silicon nanowires is functionalised with receptor (capture) molecules capable of binding to target (analyte) molecules.

15. A sensor chip comprising an array of pixels, each of claim 1, connected in a mixed analogue/digital amplifier circuit.

16. A diagnostic method for label-free detection of a target molecule (analyte) in a liquid or gas medium by monitoring changes in an electric current recorded by the sensor comprising the pixel of claim 1 or array thereof upon contacting with said medium.

17. The method of claim 16, wherein said method comprises affinity-based diagnostics of said target molecule by monitoring binding or unbinding interaction of said target molecule to a receptor molecule attached to said sensor surface or by monitoring the changes in the spatial molecular configuration of the bound target molecule and/or receptor molecule.

18. The method of claim 16, wherein said method comprises metabolic diagnostics of said target molecule by monitoring the formation of a product of said target molecule in a metabolic enzymatic reaction, or by observing an electron transfer from said target molecule to said sensor surface.

19. In a method for label-free detection of a target molecule (analyte) in a medium by monitoring changes in an electric current recorded by a sensor open for contact with said medium, the improvement comprises using the sensor comprising the pixel of claim 1 or array thereof.

20. A method for performing a DC readout with the sensor comprising the pixel of claim 1 or array thereof, said method comprising:
reading the raw data of a drain-source current ($I_{DS}$) and a gate-source voltage ($V_{GS}$) from said sensor before and after addition of an analyte solution, while a drain-source voltage ($V_{DS}$) is kept constant;
sweeping the $V_{DS}$ voltage with a reference electrode of said sensor and repeating the previous step for different $V_{DS}$ voltages to generate the sets of $I_{DS}$-$V_{GS}$ raw data, each set for one specific $V_{DS}$ voltage, and to plot the corresponding $I_{DS}$ vs $V_{GS}$ curves;
calculating a transconductance ($g_m$) by taking a first derivative of said $I_{DS}$-$V_{GS}$ curves at the corresponding $V_{DS}$ voltages and plotting the calculated $g_m$ vs $V_{GS}$ curves, each curve for one specific $V_{DS}$ voltage;
finding the maximum transconductance point $g_m$ (max) (the peak) in said $g_m$-$V_{GS}$ curves and extracting the $V_{GS}$ voltage corresponding to the $g_m$ (max) in these curves; and choosing the point on the $I_{DS}$-$V_{GS}$ curves generated in Step 1, said point corresponding to the $V_{GS}$ voltage obtained in Step 3, and taking a difference between said $V_G$ voltages of said sensor before and after addition of an analyte solution, thereby calculating a voltage shift ($\Delta V$).

21. A method for performing an AC readout with the sensor comprising the pixel of claim 1 or array thereof, said method comprising:
reading the raw data of a root-mean-square voltage (Vrms) from a lock-in amplifier of said sensor before and after addition of an analyte solution;
plotting said Vrms data vs a current frequency ($\omega$) of said sensor before and after addition of an analyte solution, thereby obtaining two Vrms-$\omega$ curves;
calculating the amplitude and frequency differences of a resonance peak between two said Vrms-$\omega$ curves;
calculating a cut-off slope of two said Vrms-w curves;
calculating the cut-off frequency corresponding to the frequency at the lowest amplitude of the resonance peak by:
processing the first polynomial fit to said cut-off slope;
finding an x-intercept, which is equal to said cut-off frequency, of the fitted curves for said sensor before and after addition of said analyte solution; and
taking a difference between the calculated cut-off frequencies of said sensor before and after addition of said analyte solution, thereby calculating a cut-off frequency shift.

22. A method for performing a triple readout comprising:
(I) performing a DC readout by:
reading the raw data of a drain-source current ($I_{DS}$) and a gate-source voltage ($V_{GS}$) from said sensor before and after addition of an analyte solution, while a drain-source voltage ($V_{DS}$) is kept constant;
sweeping the $V_{DS}$ voltage with a reference electrode of said sensor and repeating the previous step for different $V_{DS}$ voltages to generate the sets of $I_{DS}$-$V_{GS}$ raw data, each set for one specific $V_{DS}$ voltage, and to plot the corresponding $I_{DS}$ vs $V_{GS}$ curves;
calculating a transconductance ($g_m$) by taking a first derivative of said $I_{DS}$-$V_{GS}$ curves at the corresponding $V_{DS}$ voltages and plotting the calculated $g_m$ vs $V_{GS}$ curves, each curve for one specific $V_{DS}$ voltage;
finding the maximum transconductance point $g_m$ (max) (the peak) in said $g_m$-$V_{GS}$ curves and extracting the $V_{GS}$ voltage corresponding to the $g_m$ (max) in these curves; and
choosing the point on the $I_{DS}$-$V_{GS}$ curves generated in Step 1, said point corresponding to the $V_{GS}$ voltage obtained in Step 3, and taking a difference between said $V_G$ voltages of said sensor before and after addition of an analyte solution, thereby calculating a voltage shift ($\Delta V$);
(II) performing an AC readout by:
reading the raw data of a root-mean-square voltage (Vrms) from a lock-in amplifier of said sensor before and after addition of an analyte solution;
plotting said Vrms data vs a current frequency ($\omega$) of said sensor before and after addition of an analyte solution, thereby obtaining two Vrms-$\omega$ curves;
calculating the amplitude and frequency differences of a resonance peak between two said Vrms-$\omega$ curves;
calculating a cut-off slope of two said Vrms-w curves;
calculating the cut-off frequency corresponding to the frequency at the lowest amplitude of the resonance peak by:
processing the first polynomial fit to said cut-off slope;
finding an x-intercept, which is equal to said cut-off frequency, of the fitted curves for said sensor before and after addition of said analyte solution; and
taking a difference between the calculated cut-off frequencies of said sensor before and after addition of said analyte solution, thereby calculating a cut-off frequency shift; and
(III) performing temperature sensing,
wherein the DC readout, the AC readout and temperature sensing are performed with the sensor comprising the pixel of claim 1 or array thereof.

23. A microelectronic sensor comprising a disposable unit mounted on a chip substrate and a reader unit mounted on a flexible printed circuit board (PCB), wherein:
said disposable unit comprises:
an array of pixels, each of claim 1, arranged in rows and columns and open for contact with a medium,
a row decoder connected to said array for addressing said pixels arranged in rows; and
a column decoder connected to said array for addressing said pixels arranged in columns; and
said reader unit comprises:
a voltage source connected to an electric circuit for supplying electric power to the sensor;
an integrated or CMOS current amplifier connected to said array for amplification of an electric current obtained from said pixels;
an integrated waveform generator for generating frequency of a sinusoidal electric stimulation;
an analogue-to-digital converter with in-built digital input/output connected to said current amplifier for outputting the converted signal to a user interface; and
a connection module for wired connection of the sensor to said user interface, or a wireless connection module for wireless connection of the sensor to said user interface.

24. The sensor of claim 23, wherein said sensor further comprises a microfluidic chip or lateral flow strip for supplying an analyte solution to said pixels.

25. The sensor of claim 23, wherein said voltage source is a battery.

26. The sensor of claim 23, wherein said sensor is powered wirelessly via an RFID (Radio-Frequency Identification) tag.

27. A wearable-patch sensor comprising a disposable unit mounted on a chip substrate and a reader unit mounted on a flexible printed circuit board (PCB), wherein:
- said disposable unit comprises an array of pixels, each of claim 1, open for contact with a medium; and
- said reader unit comprises:
  - an ASIC (Application-Specific Integrated Circuit) chip customised for a particular use of the sensor;
  - a battery or power receiver connected to an electric circuit for supplying electric power to the sensor; and
  - a wireless connection module for wireless connection of the sensor to a user interface.

28. The sensor of claim 27, wherein said ASIC chip comprises an amplifier for amplification of an electric current obtained from said pixels, an additional voltage source for powering the sensor, a waveform function generator for generating frequency of a sinusoidal electric stimulation, and decoders.

* * * * *